(12) United States Patent
Cardinal-David et al.

(10) Patent No.: US 10,174,061 B2
(45) Date of Patent: *Jan. 8, 2019

(54) CARBIDOPA AND L-DOPA PRODRUGS AND METHODS OF USE

(71) Applicant: AbbVie Inc., North Chicago, IL (US)

(72) Inventors: Benoit Cardinal-David, Chicago, IL (US); Vincent S. Chan, Evanston, IL (US); Brian P. Enright, Gurnee, IL (US); Ye Huang, Gurnee, IL (US); Alexander D. Huters, Chicago, IL (US); Russell C. Klix, Buffalo Grove, IL (US); Scott W. Krabbe, Lindenhurst, IL (US); Philip R. Kym, Libertyville, IL (US); Yanbin Lao, Lake Bluff, IL (US); Xiaochun Lou, Long Grove, IL (US); Sean E. Mackey, Grayslake, IL (US); Mark A. Matulenko, Libertyville, IL (US); Peter T. Mayer, Libertyville, IL (US); Christopher P. Miller, Lake Forest, IL (US); James Stambuli, Buffalo Grove, IL (US); Eric A. Voight, Pleasant Prairie, WI (US); Zhi Wang, Libertyville, IL (US); Geoff G. Zhang, Vernon Hills, IL (US); Valentino J. Stella, Lawrence, KS (US)

(73) Assignee: ABBVIE INC., North Chicago, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/715,245

(22) Filed: Sep. 26, 2017

(65) Prior Publication Data
US 2018/0079762 A1    Mar. 22, 2018

Related U.S. Application Data

(63) Continuation of application No. 15/216,009, filed on Jul. 21, 2016, now abandoned, which is a continuation of application No. 14/919,418, filed on Oct. 21, 2015, now Pat. No. 9,446,059.

(60) Provisional application No. 62/066,771, filed on Oct. 21, 2014.

(51) Int. Cl.
| | | |
|---|---|---|
| C07F 9/09 | (2006.01) |
| A61K 31/661 | (2006.01) |
| C07F 9/06 | (2006.01) |
| A61K 31/6615 | (2006.01) |
| C07C 281/02 | (2006.01) |
| C07C 309/24 | (2006.01) |
| C07C 47/277 | (2006.01) |
| A61K 45/06 | (2006.01) |

(52) U.S. Cl.
CPC .......... *C07F 9/094* (2013.01); *A61K 31/661* (2013.01); *A61K 31/6615* (2013.01); *A61K 45/06* (2013.01); *C07C 47/277* (2013.01); *C07C 281/02* (2013.01); *C07C 309/24* (2013.01); *C07F 9/06* (2013.01); *C07B 2200/13* (2013.01)

(58) Field of Classification Search
CPC ...................................................... C07F 9/094
USPC ....................................................... 514/107
See application file for complete search history.

(56) References Cited

U.S. PATENT DOCUMENTS

| | | | |
|---|---|---|---|
| 3,132,171 A | 5/1964 | Herman |
| 4,616,484 A | 10/1986 | Pawelek |
| 5,073,547 A | 12/1991 | Casagrande et al. |
| 5,438,047 A | 8/1995 | Santangelo et al. |
| 5,635,213 A | 6/1997 | Nystrom et al. |
| 6,365,180 B1 | 4/2002 | Meyer et al. |
| 6,872,838 B2 | 3/2005 | Stella et al. |
| 8,048,926 B2 | 11/2011 | Atlas |
| 9,446,059 B2 | 9/2016 | Cardinal-David et al. |
| 2005/0282891 A1 | 12/2005 | Xiang et al. |
| 2012/0288446 A1 | 11/2012 | Garigapati et al. |
| 2013/0253056 A1 | 9/2013 | Nemas et al. |
| 2016/0022573 A1 | 1/2016 | Yacoby-Zeevi |

FOREIGN PATENT DOCUMENTS

| | | |
|---|---|---|
| EP | 0393781 A2 | 10/1990 |
| WO | WO 92/13868 A1 | 8/1992 |
| WO | WO 94/03461 A1 | 2/1994 |
| WO | WO 2008/076458 A1 | 2/1994 |
| WO | WO 2004/052841 A1 | 6/2004 |
| WO | WO 2009/143295 A1 | 11/2009 |
| WO | WO-2010/134074 A1 | 11/2010 |
| WO | WO-20111056240 A2 | 5/2011 |
| WO | WO-2012/079072 A2 | 6/2012 |

OTHER PUBLICATIONS

International Search Report dated Feb. 9, 2016 issued in PCT Patent Application No. PCT/US2015/056686.
Hideko Maeda et al. (2011), "Phosphonylation of L-Dopa with Sodium Diphosphonate in Aqueous Solution", *Phosphorus Research Bulletin*, vol. 25, 2011, pp. 56-60.
Safadi, M., et al. (1993), "Phosphoryloxymethyl Carbamates and Carbonates —Novel Water—Soluble Prodrugs for Amines and Hindered Alcohols", *Pharmaceutical Research*, 10(9): 1350-1355.
Pawelek, J., et al. (1986), "Increase in Melanin Formation and Promotion of Cytotoxicity in Cultured Menanoma Cells Caused by Phosphorylated Isomers of L-Dopa". *Cancer Res*, 46: 493-497.

(Continued)

*Primary Examiner* — Taofiq A Solola
(74) *Attorney, Agent, or Firm* — Sterne, Kessler, Goldstein & Fox P.L.L.C.

(57) ABSTRACT

The present disclosure relates to (a) carbidopa prodrugs, (b) pharmaceutical combinations and compositions comprising a carbidopa prodrug and/or an L-dopa prodrug, and (c) methods of treating Parkinson's disease and associated conditions comprising administering a carbidopa prodrug and an L-dopa prodrug to a subject with Parkinson's disease.

4 Claims, 22 Drawing Sheets

(56) References Cited

OTHER PUBLICATIONS

Kearney, A., et al. (1992), "The in vitro Enzymic Liabilities of Chemically Distinct Phosphomonoester Prodrugs", *Pharmaceutical Research*, 9(4): 497-503.
Dhareshwar, S., et al. (2008), Your Prodrug Releases Formaldehyde: Should You Be Concerned? No!, *Journal of Pharmaceutical Sciences*, 97(10): 4184-4193.
Zhu, Z., et al. (2000), "Phosphate Prodrugs of PD154075", *Bioorganic & Medicinal Chemistry Letters*, 10: 1121-1124.
Agin, P., et al. (1987), "Phosphorylated Mixed Isomers of L-Dopa increase Melanin Content in Skins of Skh-2 Pigmented Hairless Mice", *Pigment Cell Research*, 1: 137-142.
Glacomonl, P. (2001), "Sun Protection in Man", *Comprehensive Series In Photosciences*, 3: 642-648.
Written Opinion of the Intellectual Property Office of Singapore Patent Application No. 11201703170R, dated Feb. 26, 2018.
Co-pending Application, U.S. Appl. No. 15/491,642, inventors Cardinal-David et al., filed Apr. 19, 2017 (Not Published).

CARBIDOPA AND L-DOPA PRODRUGS AND METHODS OF USE

FIELD OF THE INVENTION

The present disclosure relates to (a) carbidopa prodrugs, (b) L-dopa prodrugs, (c) pharmaceutical combinations and compositions comprising a carbidopa prodrug and/or an L-dopa prodrug, and (d) methods of treating Parkinson's disease and associated conditions comprising administering a carbidopa prodrug and an L-dopa prodrug to a subject with Parkinson's disease.

BACKGROUND OF THE INVENTION

Parkinson's disease is a chronic and progressive neurodegenerative condition characterized by reduced levels in the brain of the neurotransmitter dopamine (i.e., 3,4-dihydroxyphenethylamine). Administration of L-dopa (i.e., L-3,4-dihydroxyphenylalanine) currently is the most effective therapy for treating a patient with Parkinson's disease. L-dopa, which unlike dopamine can cross the blood-brain barrier, is enzymatically converted in the brain to dopamine resulting in an increase in dopamine levels:

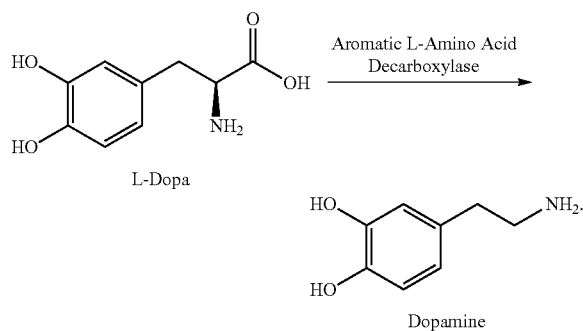

The conversion of L-dopa to dopamine is catalyzed by aromatic L-amino acid decarboxylase, a ubiquitous enzyme that promotes central as well as peripheral metabolism of L-dopa to dopamine. Due to the peripheral metabolism of L-dopa, a relatively large dose of L-dopa is required to achieve therapeutically effective dopamine levels in the brain. Administration of such large L-dopa doses results in elevated peripheral dopamine levels that can cause nausea in some patients. To overcome these problems, L-dopa generally is co-administered with a peripheral aromatic L-amino acid decarboxylase inhibitor such as carbidopa (i.e., (2S)-3-(3,4-dihydroxyphenyl)-2-hydrazino-2-methylpropanoic acid):

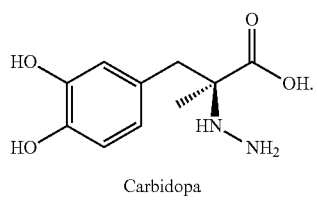

Co-administration of carbidopa with L-dopa inhibits the peripheral metabolism of L-dopa to dopamine, which significantly reduces the L-dopa dose required for a therapeutically effective response and reduces the associated side effects.

Even when L-dopa and carbidopa are co-administered, however, it is difficult to consistently maintain the desired dopamine levels in the brain due to the relatively short half-life of L-dopa in plasma. In addition, the tolerance of many patients to variability in dopamine levels in the brain decreases as the disease progresses. One approach that has been effective in reducing variability of dopamine levels is the continuous intestinal delivery of an adjustable dose of an L-dopa/carbidopa gel known by its commercial name, DuoDopa® in Europe and Duopa® in the United States. DuoDopa®/Duopa® is a suspension of L-dopa/carbidopa monohydrate (4:1 ratio of L-dopa to carbidopa monohydrate) in an aqueous gel (carboxymethyl cellulose sodium) having a viscosity that permits homogeneous distribution of micronized substance particles. The gel is delivered to the proximal small intestine through a jejunal tube inserted through a percutaneous endoscopic gastrostomy port. DuoDopa®/Duopa® is packaged in medication cassette reservoirs and continuously administered via a software-controlled ambulatory infusion pump. Although L-dopa and carbidopa have been co-administered to treat Parkinson's disease for several decades, a pharmacokinetically-consistent delivery system that does not require intestinal insertion is not commercially available.

A major challenge to the development of less invasive or otherwise improved modes of administering L-dopa and carbidopa has been the solubility of those compounds. They each have low aqueous solubility at the pH range required for infusion. Stable, more highly concentrated, and/or less viscous formulations comprising L-dopa and/or carbidopa (or compounds capable of in vivo bioconversion to L-dopa and/or carbidopa) are desirable. Such formulations can provide advantages over existing intestinal infusion therapy including: (a) decreasing the volume and improving the pumpability of the formulation to be delivered to the patient which also allows for a reduction of the size and weight of delivery device; (b) extending the shelf life of the formulation by reducing degradation and improving stability of the formulation; and/or (c) providing the patient with increased flexibility in managing their treatment by reducing or eliminating cold storage requirements for the formulation (e.g., longer times to handle the formulation outside of refrigerated storage). Such stable, more highly concentrated, and/or less viscous formulations also can be employed in less invasive modes of administration (e.g., subcutaneous infusion).

Accordingly, there is a continuing need for improved compositions and methods that can provide continuous and consistent dopamine levels in the brain to effectively treat movement disorders such as Parkinson's disease. The present disclosure provides such improved compositions and methods.

SUMMARY OF THE INVENTION

In one aspect, the present disclosure relates to a compound corresponding in structure to Formula (I):

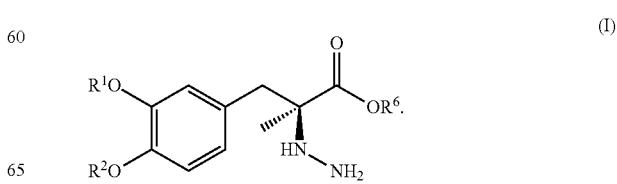

or a pharmaceutically acceptable salt thereof, wherein $R^1$ and $R^2$ are each independently selected from the group consisting of hydrogen, —P(O)(OH)$_2$, and —R$^5$—O—P(O)(OH)$_2$; $R^5$ is a $C_1$-$C_4$-alkyl; $R^6$ is hydrogen or a $C_1$-$C_4$-alkyl; and provided that at least one of $R^1$ and $R^2$ is —P(O)(OH)$_2$ or —R$^5$—O—P(O)(OH)$_2$.

In another aspect, the present disclosure relates to a compound corresponding in structure Formula (I):

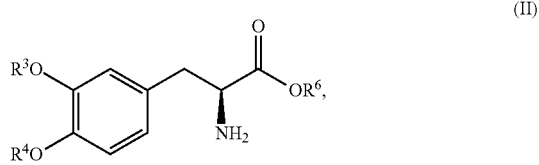

(II)

or a pharmaceutically acceptable salt thereof, wherein $R^3$ and $R^4$ are each independently selected from the group consisting of hydrogen, —P(O)(OH)$_2$, and —R$^5$—O—P(O)(OH)$_2$; $R^5$ is a $C_1$-$C_4$-alkyl; $R^6$ is hydrogen or a $C_1$-$C_4$-alkyl; and provided that at least one of $R^3$ and $R^4$ is —P(O)(OH)$_2$ or —R$^5$—O—P(O)(OH)$_2$.

In another aspect, the present disclosure relates to a pharmaceutical combination comprising a first compound corresponding in structure to Formula (I), or a pharmaceutically acceptable salt thereof, and a second compound corresponding in structure to Formula (II) or a pharmaceutically acceptable salt thereof.

In another aspect, the present disclosure relates to a pharmaceutical composition comprising a first compound corresponding in structure to Formula (I), or a pharmaceutically acceptable salt thereof, and a pharmaceutically acceptable carrier. In certain aspects, the pharmaceutical composition may further comprise a second compound corresponding in structure to Formula (II) or a pharmaceutically acceptable salt thereof.

In another aspect, the present disclosure relates to a method of treating Parkinson's disease or an associated condition in a patient comprising administering to the patient a therapeutically effective amount of a pharmaceutical combination comprising a first compound corresponding in structure to Formula (I), or a pharmaceutically acceptable salt thereof, and a second compound corresponding in structure to Formula (II), or a pharmaceutically acceptable salt thereof. In certain aspects, the method comprises administering the first compound corresponding in structure to Formula (I), or a pharmaceutically acceptable salt thereof, and the second compound corresponding in structure to Formula (II) in a single pharmaceutical composition or in separate pharmaceutical compositions.

Further benefits of the present disclosure will be apparent to one skilled in the art from reading this patent application. The embodiments of the disclosure described in the following paragraphs are intended to illustrate the invention and should not be deemed to narrow the scope of the invention.

DETAILED DESCRIPTION OF THE INVENTION

Figure 1:
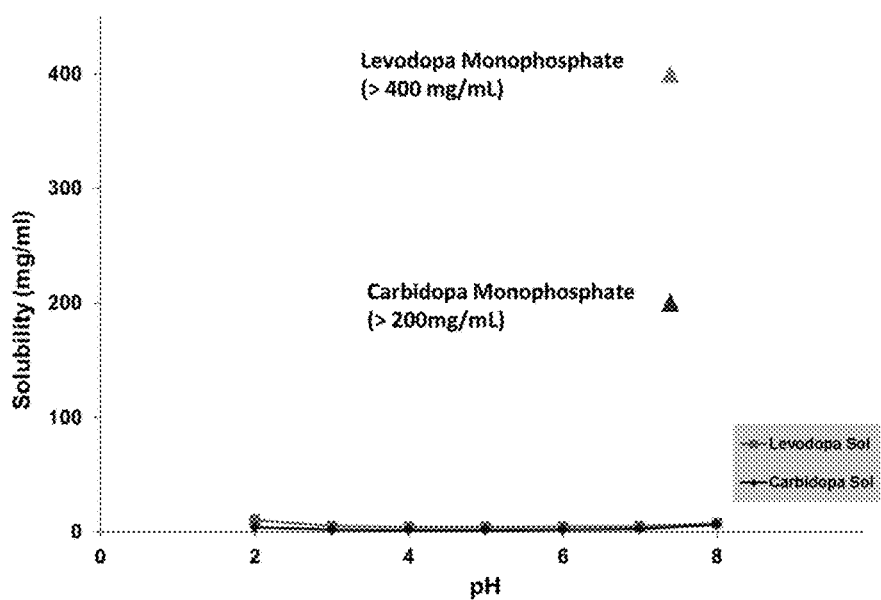
FIG. 1 is a graph of the solubility of L-dopa 4'-monophosphate and carbidopa 4'-monophosphate at a pH of 7.4 and the solubility of L-dopa and carbidopa.

This written description uses examples to disclose the invention, including the best mode, and also to enable any person skilled in the art to practice the invention, including making and using any of the disclosed carbidopa phosphate prodrugs or pharmaceutical compositions, and performing any of the disclosed methods or processes. The patentable scope of the invention is defined by the claims, and may include other examples that occur to those skilled in the art. Such other examples are intended to be within the scope of the claims if they have elements that do not differ from the literal language of the claims, or if they include equivalent elements.

I. DEFINITIONS

Section headings as used in this section and the entire disclosure are not intended to be limiting.

Where a numeric range is recited, each intervening number within the range is explicitly contemplated with the same degree of precision. For example, for the range 6 to 9, the numbers 7 and 8 are contemplated in addition to 6 and 9, and for the range 6.0 to 7.0, the numbers 6.0, 6.1, 6.2, 6.3, 6.4, 6.5, 6.6, 6.7, 6.8, 6.9 and 7.0 are explicitly contemplated. In the same manner, all recited ratios also include all sub-ratios falling within the broader ratio.

The singular forms "a," "an" and "the" include plural referents unless the context clearly dictates otherwise.

The term "and/or" as used in a phrase such as "A and/or B" herein is intended to include "A and B", "A or B", "A", and "B".

The term "about" generally refers to a range of numbers that one of skill in the art would consider equivalent to the recited value (i.e., having the same function or result). In many instances, the term "about" may include numbers that are rounded to the nearest significant figure.

Unless the context requires otherwise, the terms "comprise," "comprises," and "comprising" are used on the basis and clear understanding that they are to be interpreted inclusively, rather than exclusively, and that Applicant intends each of those words to be so interpreted in construing this patent, including the claims below.

The terms "improve" and "improving" have their plain and ordinary meaning to one skilled in the art of pharmaceutical or medical sciences and specifically include ameliorating the effects of Parkinson's disease, or decreasing or lessening a side effect of Parkinson's disease.

The term "patient" includes mammals and humans, particularly humans.

The term "pharmaceutically acceptable carrier" or "pharmaceutically acceptable excipient" refers to any and all solvents, dispersion media, preservatives, antioxidants, coatings, isotonic and absorption delaying agents, and the like, that are compatible with pharmaceutical administration.

The term "pharmaceutically acceptable salt" refers to a salt of a compound that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methyl-bicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; and (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, N-methylglucamine, dicyclohexylamine, and the like.

The terms "reduce" and "reducing" have their plain and ordinary meanings to one skilled in the art of pharmaceutical or medical sciences and specifically include diminishing or decreasing the number of occurrences, the duration, or the intensity, of a Parkinson's disease side effect, such as dyskinesias or hallucinations.

The term "therapeutically effective amount" means an amount of a compound that, when administered to a patient suffering from or susceptible to Parkinson's disease or an associated condition is sufficient, either alone or in combination with additional therapies, to effect treatment for Parkinson's disease or the associated condition. The "therapeutically effective amount" will vary depending, for example, on the compound, the condition treated and its severity, and the age and weight of the patient to be treated.

The terms "treat" and "treating" have their plain and ordinary meaning to one skilled in the art of pharmaceutical or medical sciences and specifically include improving the quality of life or reducing the symptoms or side effects of Parkinson's disease.

II. CARBIDOPA AND L-DOPA PRODRUGS

As previously noted, the inherently low aqueous solubility of L-dopa and carbidopa at physiologically acceptable pH for infusion presents a significant technical challenge to the development of improved pharmaceutical compositions and methods of treatment. Such challenges include, for example, difficulties in achieving appropriate dosing volume and formulation stability within the required pH limitations. These challenges are further complicated by the requirement that the pharmaceutical compositions and methods of treatment provide pharmacokinetically-appropriate and pharmacokinetically-consistent control of dopamine levels in the patient's brain.

Prior prodrug approaches have failed for a number of reasons due to these technical challenges (including insufficient chemical stability, insufficient solubility, in vivo bioconversion issues, and the like) and no L-dopa prodrugs or carbidopa prodrugs for infusion have been successfully commercialized. The prodrugs, pharmaceutical combinations and compositions, and methods of treatment of the present disclosure, however, have overcome these challenges. They can be used to treat patients suffering from Parkinson's disease and associated conditions and do not always require invasive surgery. In various embodiments of the present disclosure, the compositions comprise L-dopa and carbidopa prodrugs that convert to L-dopa and carbidopa in vivo which allows for delivery by continuous administration methods including intragastric, intramuscular, intravenous, and subcutaneous administration. These novel prodrugs, combinations, compositions, and methods of the present disclosure represent an advancement in the treatment of Parkinson's disease and other related conditions.

A. Carbidopa Prodrugs

In one embodiment, therefore, the present disclosure relates to a compound corresponding in structure to Formula (I):

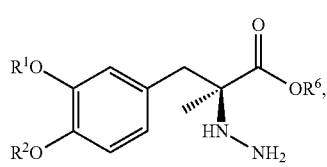

(I)

or a pharmaceutically acceptable salt thereof, wherein $R^1$ and $R^2$ are each independently selected from the group consisting of hydrogen, —P(O)(OH)$_2$, and —R$^5$—O—P(O)(OH)$_2$; $R^5$ is a C$_1$-C$_4$-alkyl; $R^6$ is hydrogen or a C$_1$-C$_4$-alkyl; and provided that at least one of $R^1$ and $R^2$ is —P(O)(OH)$_2$ or —R$^5$—O—P(O)(OH)$_2$. In one aspect, the compound corresponds in structure to Formula (I). In another aspect, the compound is a pharmaceutically acceptable salt of a compound corresponding in structure to Formula (I).

In another embodiment, the present disclosure relates to a compound corresponding in structure to Formula (I) or a pharmaceutically acceptable salt thereof, wherein $R^1$ and $R^2$ are each independently selected from the group consisting of hydrogen and —P(O)(OH)$_2$; $R^6$ is hydrogen or a C$_1$-C$_4$-alkyl; and provided that at least one of $R^1$ and $R^2$ is —P(O)(OH)$_2$. In one aspect, the compound corresponds in structure to Formula (I). In another aspect, the compound is a pharmaceutically acceptable salt of a compound corresponding in structure to Formula (I).

In another embodiment, the present disclosure relates to a compound corresponding in structure to Formula (I-a):

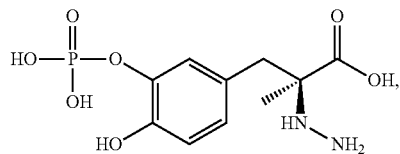

(I-a)

or a pharmaceutically acceptable salt thereof. In one aspect, the compound corresponds in structure to Formula (I-a). In another aspect, the compound is a pharmaceutically acceptable salt of a compound corresponding in structure to Formula (I-a).

In another embodiment, the present disclosure relates to a compound corresponding in structure to Formula (I-b):

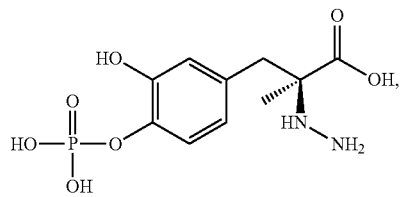

(I-b)

or a pharmaceutically acceptable salt thereof. In one aspect, the compound corresponds in structure to Formula (I-b). In another aspect, the compound is a pharmaceutically acceptable salt of a compound corresponding in structure to Formula (I-b).

In another embodiment, the present disclosure relates to a compound corresponding in structure to Formula (I-c):

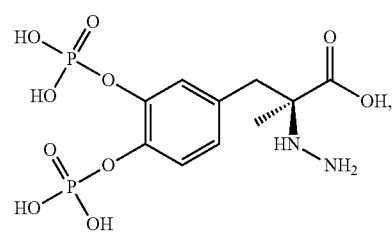

(I-c)

or a pharmaceutically acceptable salt thereof. In one aspect, the compound corresponds in structure to Formula (I-c). In another aspect, the compound is a pharmaceutically acceptable salt of a compound corresponding in structure to Formula (I-c).

In another embodiment, the present disclosure relates to a compound corresponding in structure to Formula (I) or a pharmaceutically acceptable salt thereof, wherein $R^1$ and $R^2$ are each independently selected from the group consisting of hydrogen and —R$^5$—O—P(O)(OH)$_2$; wherein $R^5$ is a C$_1$-C$_4$-alkyl; $R^6$ is hydrogen or a C$_1$-C$_4$-alkyl; and provided that at least one of $R^1$ and $R^2$ is —R$^5$—O—P(O)(OH)$_2$.

In another embodiment, the present disclosure relates to a compound corresponding in structure to Formula (I) or a pharmaceutically acceptable salt thereof, wherein $R^1$ and $R^2$ are each independently selected from the group consisting of hydrogen and —R$^5$—O—P(O)(OH)$_2$; wherein $R^5$ is methyl; $R^6$ is hydrogen or a C$_1$-C$_4$-alkyl; and provided that at least one of $R^1$ and $R^2$ is —R$^5$—O—P(O)(OH)$_2$.

In another embodiment, the present disclosure relates to a compound corresponding in structure to Formula (I) or a pharmaceutically acceptable salt thereof, wherein $R^1$ and $R^2$ are each independently selected from the group consisting of hydrogen and —R$^5$—O—P(O)(OH)$_2$; wherein $R^5$ is ethyl; $R^6$ is hydrogen or a C$_1$-C$_4$-alkyl; and provided that at least one of $R^1$ and $R^2$ is —R$^5$—O—P(O)(OH)$_2$.

In another embodiment, the present disclosure relates to a compound corresponding in structure to Formula (I) or a pharmaceutically acceptable salt thereof, wherein $R^1$ and $R^2$ are each independently selected from the group consisting of hydrogen and —R$^5$—O—P(O)(OH)$_2$; wherein $R^5$ is propyl; $R^6$ is hydrogen or a C$_1$-C$_4$-alkyl; and provided that at least one of $R^1$ and $R^2$ is —R$^5$—O—P(O)(OH)$_2$.

In another embodiment, the present disclosure relates to a compound corresponding in structure to Formula (I) or a pharmaceutically acceptable salt thereof, wherein $R^1$ and $R^2$ are each independently selected from the group consisting of hydrogen and —R$^5$—O—P(O)(OH)$_2$; wherein $R^5$ is butyl; $R^6$ is hydrogen or a C$_1$-C$_4$-alkyl; and provided that at least one of $R^1$ and $R^2$ is —R$^5$—O—P(O)(OH)$_2$.

In another embodiment, the present disclosure relates to a compound corresponding in structure to Formula (I) or a pharmaceutically acceptable salt thereof, wherein $R^1$ and $R^2$ are each independently selected from the group consisting of hydrogen, —P(O)(OH)$_2$, and —R$^5$—O—P(O)(OH)$_2$; $R^5$ is a C$_1$-C$_2$-alkyl; $R^6$ is hydrogen; and provided that at least one of $R^1$ and $R^2$ is —P(O)(OH)$_2$ or —R$^5$—O—P(O)(OH)$_2$.

In another embodiment, the present disclosure relates to a compound corresponding in structure to Formula (I) or a pharmaceutically acceptable salt thereof, wherein $R^1$ and $R^2$ are each independently hydrogen or $-R^5-O-P(O)(OH)_2$; $R^5$ is a $C_1$-$C_2$-alkyl; $R^6$ is hydrogen; and provided that one of $R^1$ and $R^2$ is $-R^5-O-P(O)(OH)_2$.

In another embodiment, the present disclosure relates to a compound corresponding in structure to Formula (I-d):

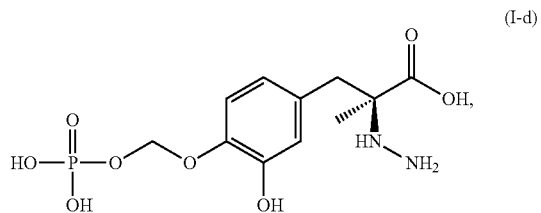 [SMILES: C[C@@](Cc1ccc(OCOP(=O)(O)O)c(O)c1)(NN)C(=O)O]

(I-d)

or a pharmaceutically acceptable salt thereof. In one aspect, the compound corresponds in structure to Formula (I-d). In another aspect, the compound is a pharmaceutically acceptable salt of a compound corresponding in structure to Formula (I-d).

In another embodiment, the present disclosure relates to a compound corresponding in structure to Formula (I-e):

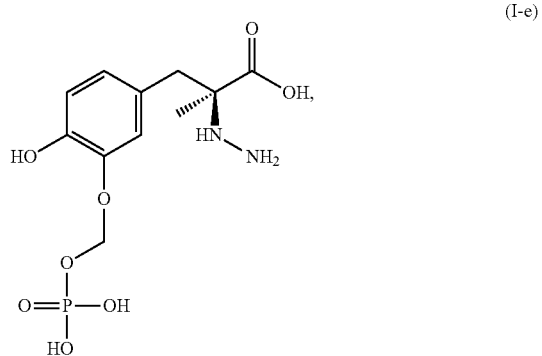 [SMILES: C[C@@](Cc1ccc(O)c(OCOP(=O)(O)O)c1)(NN)C(=O)O]

(I-e)

or a pharmaceutically acceptable salt thereof. In one aspect, the compound corresponds in structure to Formula (I-e). In another aspect, the compound is a pharmaceutically acceptable salt of a compound corresponding in structure to Formula (I-e).

In another embodiment, the present disclosure relates to a compound corresponding in structure to Formula (I) or a pharmaceutically acceptable salt thereof, wherein $R^1$ and $R^2$ are each independently selected from the group consisting of hydrogen and $-P(O)(OH)_2$; $R^6$ is hydrogen or a $C_1$-$C_4$-alkyl; and provided that at least one of $R^1$ and $R^2$ is $-P(O)(OH)_2$.

In another embodiment, the present disclosure relates to a compound corresponding in structure to Formula (I) or a pharmaceutically acceptable salt thereof, wherein $R^1$ and $R^2$ are each independently selected from the group consisting of hydrogen and $-P(O)(OH)_2$; $R^6$ is methyl; and provided that at least one of $R^1$ and $R^2$ is $-P(O)(OH)_2$.

In another embodiment, the present disclosure relates to a compound corresponding in structure to Formula (I) or a pharmaceutically acceptable salt thereof, wherein $R^1$ and $R^2$ are each independently selected from the group consisting of hydrogen and $-P(O)(OH)_2$; $R^6$ is ethyl; and provided that at least one of $R^1$ and $R^2$ is $-P(O)(OH)_2$.

In another embodiment, the present disclosure relates to a compound corresponding in structure to Formula (I) or a pharmaceutically acceptable salt thereof, wherein $R^1$ and $R^2$ are each independently selected from the group consisting of hydrogen and $-P(O)(OH)_2$; $R^6$ is propyl; and provided that at least one of $R^1$ and $R^2$ is $-P(O)(OH)_2$.

In another embodiment, the present disclosure relates to a compound corresponding in structure to Formula (I) or a pharmaceutically acceptable salt thereof, wherein $R^1$ and $R^2$ are each independently selected from the group consisting of hydrogen and $-P(O)(OH)_2$; $R^6$ is butyl; and provided that at least one of $R^1$ and $R^2$ is $-P(O)(OH)_2$.

In another embodiment, the present disclosure relates to a compound corresponding in structure to Formula (I) or a pharmaceutically acceptable salt thereof, wherein $R^1$ and $R^2$ are each independently hydrogen, $-P(O)(OH)_2$ or $-R^5-O-P(O)(OH)_2$; $R^5$ is a $C_1$-$C_2$-alkyl; $R^6$ is a $C_1$-$C_2$-alkyl; and provided that one of $R^1$ and $R^2$ is $-P(O)(OH)_2$ or $-R^5-O-P(O)(OH)_2$.

In another embodiment, the present disclosure relates to a compound corresponding in structure to Formula (I-f):

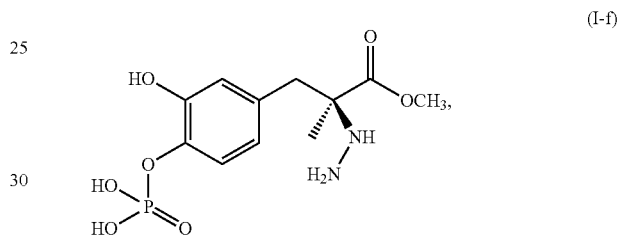

(I-f)

or a pharmaceutically acceptable salt thereof. In one aspect, the compound corresponds in structure to Formula (I-f). In another aspect, the compound is a pharmaceutically acceptable salt of a compound corresponding in structure to Formula (I-f).

B. L-Dopa Prodrugs

In another embodiment, the present disclosure relates to a compound corresponding in structure Formula (II):

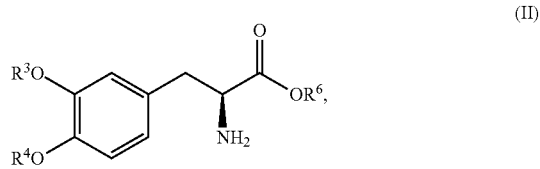

(II)

or a pharmaceutically acceptable salt thereof, wherein $R^3$ and $R^4$ are each independently selected from the group consisting of hydrogen, $-P(O)(OH)_2$, and $-R^5-O-P(O)(OH)_2$; $R^5$ is a $C_1$-$C_4$-alkyl; $R^6$ is hydrogen or a $C_1$-$C_4$-alkyl; and provided that at least one of $R^3$ and $R^4$ is $-P(O)(OH)_2$ or $-R^5-O-P(O)(OH)_2$. In one aspect, the compound corresponds in structure to Formula (II). In another aspect, the compound is a pharmaceutically acceptable salt of a compound corresponding in structure to Formula (II).

In another embodiment, the present disclosure relates to a compound corresponding in structure Formula (II) or a pharmaceutically acceptable salt thereof, wherein $R^3$ and $R^4$ are each independently selected from the group consisting of hydrogen and $-P(O)(OH)_2$; $R^6$ is hydrogen or a $C_1$-$C_4$-alkyl; and provided that at least one of $R^3$ and $R^4$ is $-P(O)(OH)_2$. In one aspect, the compound corresponds in structure to Formula (II). In another aspect, the compound is a pharmaceutically acceptable salt of a compound corresponding in structure to Formula (II).

In another embodiment, the present disclosure relates to a compound corresponding in structure to Formula (I-a):

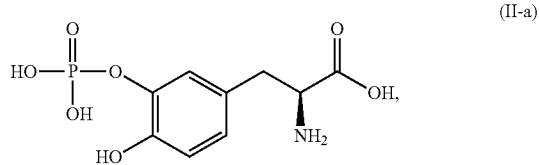 [SMILES: N[C@@H](Cc1ccc(O)c(OP(=O)(O)O)c1)C(=O)O]

(II-a)

or a pharmaceutically acceptable salt thereof. In one aspect, the compound corresponds in structure to Formula (II-a). In another aspect, the compound is a pharmaceutically acceptable salt of a compound corresponding in structure to Formula (II-a).

In another embodiment, the present disclosure relates to a compound corresponding in structure to Formula (II-b):

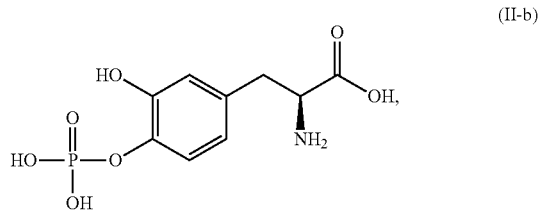 [SMILES: N[C@@H](Cc1ccc(OP(=O)(O)O)c(O)c1)C(=O)O]

(II-b)

or a pharmaceutically acceptable salt thereof. In one aspect, the compound corresponds in structure to Formula (II-b). In another aspect, the compound is a pharmaceutically acceptable salt of a compound corresponding in structure to Formula (II-b).

In another embodiment, the present disclosure relates to a compound corresponding in structure to Formula (II-c):

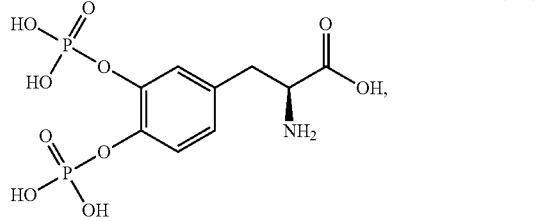

(II-c)

or a pharmaceutically acceptable salt thereof. In one aspect, the compound corresponds in structure to Formula (II-c). In another aspect, the compound is a pharmaceutically acceptable salt of a compound corresponding in structure to Formula (II-c).

In another embodiment, the present disclosure relates to a compound corresponding in structure to Formula (II) or a pharmaceutically acceptable salt thereof, wherein $R^3$ and $R^4$ are each independently selected from the group consisting of hydrogen and —$R^5$—O—P(O)(OH)$_2$; wherein $R^5$ is a $C_1$-$C_4$-alkyl; $R^6$ is hydrogen or a $C_1$-$C_4$-alkyl; and provided that at least one of $R^3$ and $R^4$ is —$R^5$—O—P(O)(OH)$_2$.

In another embodiment, the present disclosure relates to a compound corresponding in structure to Formula (II), wherein $R^3$ and $R^4$ are each independently selected from the group consisting of hydrogen and —$R^5$—O—P(O)(OH)$_2$; wherein $R^5$ is methyl; $R^6$ is hydrogen or a $C_1$-$C_4$-alkyl; and provided that at least one of $R^3$ and $R^4$ is —$R^5$—O—P(O)(OH)$_2$.

In another embodiment, the present disclosure relates to a compound corresponding in structure to Formula (II), wherein $R^3$ and $R^4$ are each independently selected from the group consisting of hydrogen and —$R^5$—O—P(O)(OH)$_2$; wherein $R^5$ is ethyl; $R^6$ is hydrogen or a $C_1$-$C_4$-alkyl; and provided that at least one of $R^3$ and $R^4$ is —$R^5$—O—P(O)(OH)$_2$.

In another embodiment, the present disclosure relates to a compound corresponding in structure to Formula (II), wherein $R^3$ and $R^4$ are each independently selected from the group consisting of hydrogen and —$R^5$—O—P(O)(OH)$_2$; wherein $R^5$ is propyl; $R^6$ is hydrogen or a $C_1$-$C_4$-alkyl; and provided that at least one of $R^3$ and $R^4$ is —$R^5$—O—P(O)(OH)$_2$.

In another embodiment, the present disclosure relates to a compound corresponding in structure to Formula (II), wherein $R^3$ and $R^4$ are each independently selected from the group consisting of hydrogen and —$R^5$—O—P(O)(OH)$_2$; wherein $R^5$ is butyl; $R^6$ is hydrogen or a $C_1$-$C_4$-alkyl; and provided that at least one of $R^3$ and $R^4$ is —$R^5$—O—P(O)(OH)$_2$.

In another embodiment, the present disclosure relates to a compound corresponding in structure to Formula (II-d):

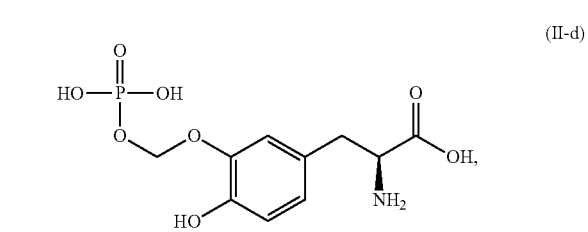 [SMILES: N[C@@H](Cc1ccc(O)c(OCOP(=O)(O)O)c1)C(=O)O]

(II-d)

or a pharmaceutically acceptable salt thereof. In one aspect, the compound corresponds in structure to Formula (II-d). In another aspect, the compound is a pharmaceutically acceptable salt of a compound corresponding in structure to Formula (II-d).

In another embodiment, the present disclosure relates to a compound corresponding in structure to Formula (II-e):

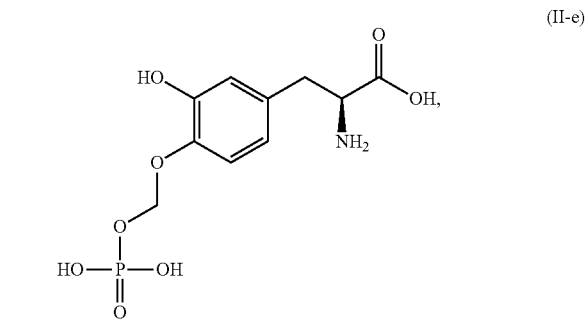 [SMILES: N[C@@H](Cc1ccc(OCOP(=O)(O)O)c(O)c1)C(=O)O]

(II-e)

or a pharmaceutically acceptable salt thereof. In one aspect, the compound corresponds in structure to Formula (II-e). In another aspect, the compound is a pharmaceutically acceptable salt of a compound corresponding in structure to Formula (II-e).

In another embodiment, the present disclosure relates to a compound corresponding in structure to Formula (II) or a pharmaceutically acceptable salt thereof, wherein $R^3$ and $R^4$ are each independently selected from the group consisting of hydrogen and —P(O)(OH)$_2$; $R^6$ is hydrogen or a $C_1$-$C_4$-alkyl; and provided that at least one of $R^3$ and $R^4$ is —P(O)(OH)$_2$.

In another embodiment, the present disclosure relates to a compound corresponding in structure to Formula (II) or a pharmaceutically acceptable salt thereof, wherein $R^3$ and $R^4$ are each independently selected from the group consisting of hydrogen and —P(O)(OH)$_2$; $R^6$ is methyl; and provided that at least one of $R^3$ and $R^4$ is —P(O)(OH)$_2$.

In another embodiment, the present disclosure relates to a compound corresponding in structure to Formula (II) or a pharmaceutically acceptable salt thereof, wherein $R^3$ and $R^4$ are each independently selected from the group consisting of hydrogen and —P(O)(OH)$_2$; $R^6$ is ethyl; and provided that at least one of $R^3$ and $R^4$ is —P(O)(OH)$_2$.

In another embodiment, the present disclosure relates to a compound corresponding in structure to Formula (II) or a pharmaceutically acceptable salt thereof, wherein $R^3$ and $R^4$ are each independently selected from the group consisting of hydrogen and —P(O)(OH)$_2$; $R^6$ is propyl; and provided that at least one of $R^3$ and $R^4$ is —P(O)(OH)$_2$.

In another embodiment, the present disclosure relates to a compound corresponding in structure to Formula (II) or a pharmaceutically acceptable salt thereof, wherein $R^3$ and $R^4$ are each independently selected from the group consisting of hydrogen and —P(O)(OH)$_2$; $R^6$ is butyl; and provided that at least one of $R^3$ and $R^4$ is —P(O)(OH)$_2$.

In another embodiment, the present disclosure relates to a compound corresponding in structure to Formula (II) or a pharmaceutically acceptable salt thereof, wherein $R^3$ is hydrogen; $R^4$ is —P(O)(OH)$_2$; and $R^6$ is methyl.

III. INTERMEDIATES

New synthesis routes disclosed herein for making L-dopa phosphates and carbidopa phosphates have led to the following new intermediate compounds:

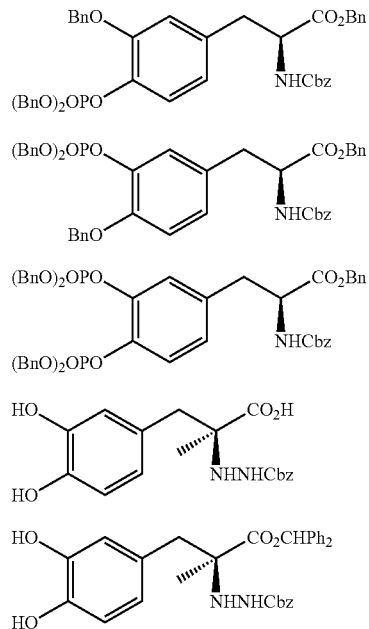
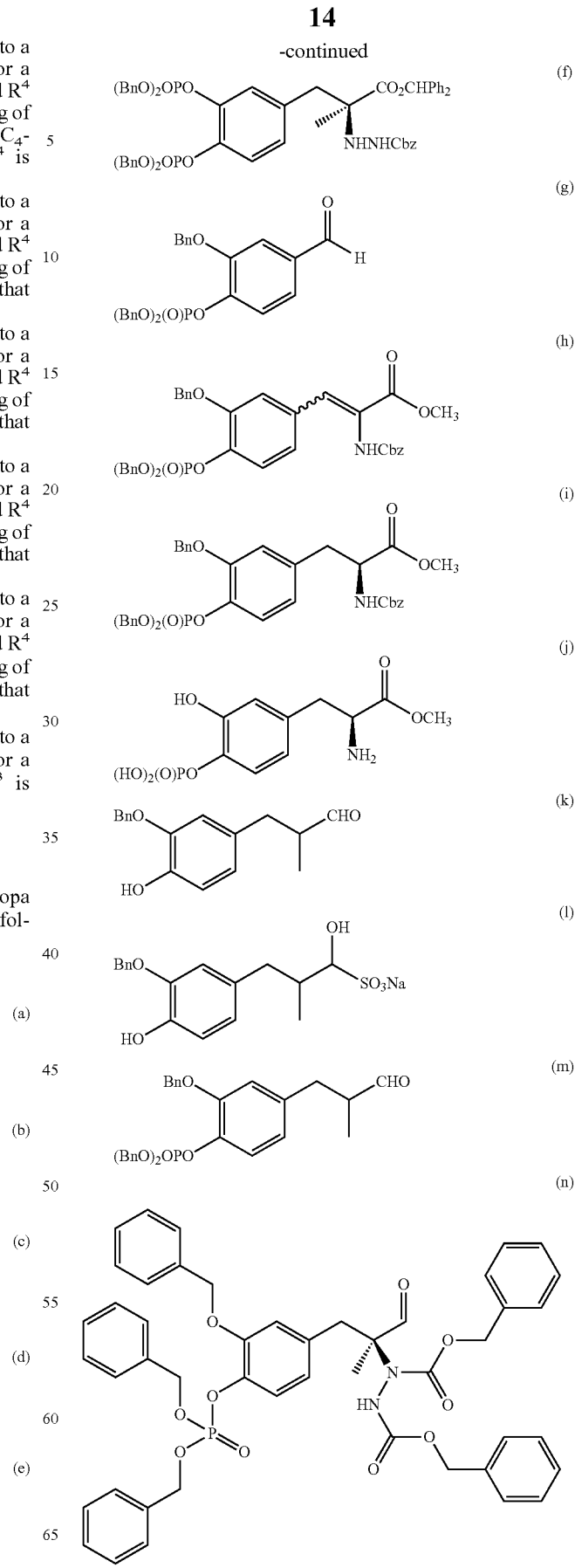

(o)
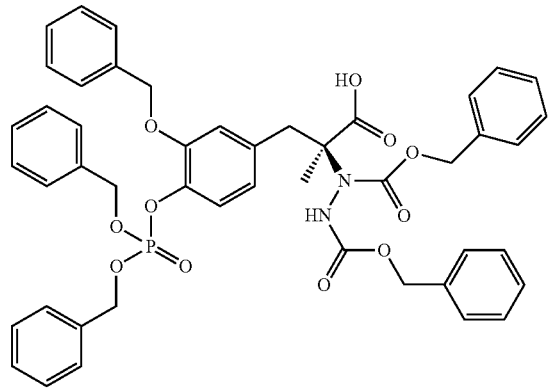

(s)
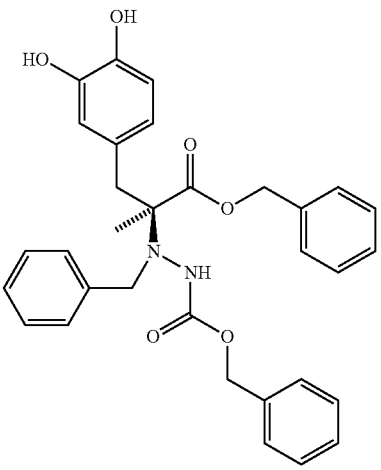

(p)
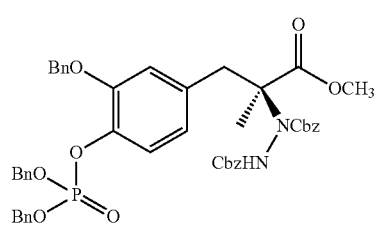

(t)
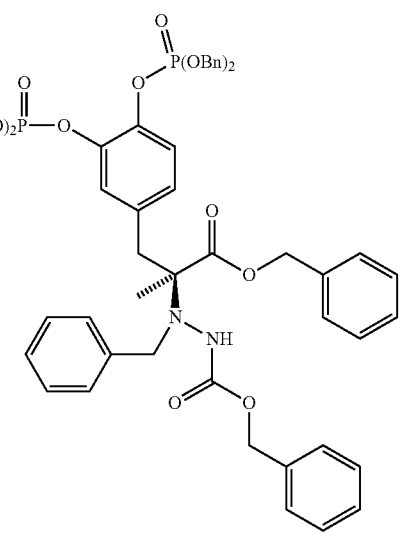

(q)
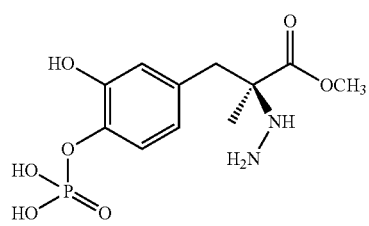

(u)
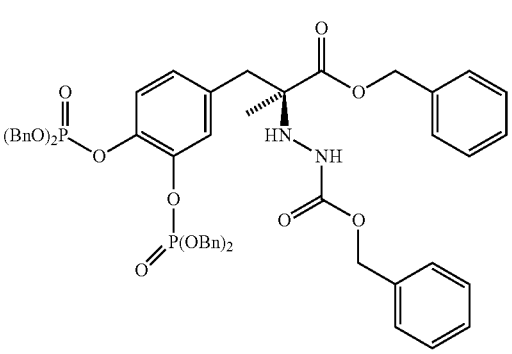

(r)
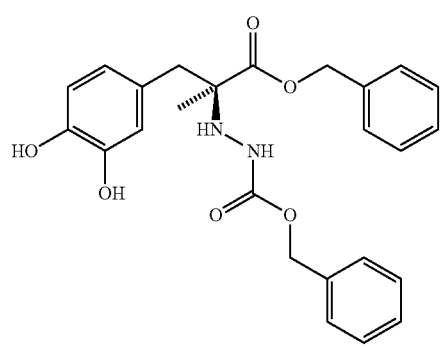

As used herein, "Bn" refers to a benzyl group and "Cbz" refers to a carboxybenzyl group.

IV. PHARMACEUTICAL COMBINATIONS/COMPOSITIONS

The present disclosure also relates to pharmaceutical combinations and compositions comprising a carbidopa prodrug and/or an L-dopa prodrug.

In some embodiments, the pharmaceutical compositions comprise a carbidopa prodrug. In other embodiments, the pharmaceutical compositions comprise an L-dopa prodrug.

In still other embodiments, the pharmaceutical compositions comprise both a carbidopa prodrug and an L-dopa prodrug.

The carbidopa and L-dopa prodrugs disclosed herein (and their pharmaceutically acceptable salts) can be formulated in the same pharmaceutical composition or can be present in separate pharmaceutical compositions. For example, a pharmaceutical combination disclosed herein can comprise a carbidopa prodrug in a first pharmaceutical composition and an L-dopa prodrug in a separate, second pharmaceutical composition. Alternatively, the pharmaceutical combination can comprise a carbidopa prodrug and L-dopa prodrug in the same pharmaceutical composition.

A. First Compound and Second Compound

In one embodiment, the pharmaceutical composition comprises a first compound corresponding in structure to Formula (I):

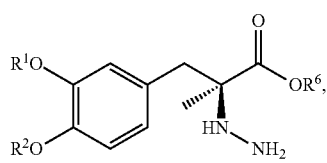

(I)

or a pharmaceutically acceptable salt thereof, and a pharmaceutically acceptable carrier; wherein $R^1$ and $R^2$ are each independently selected from the group consisting of hydrogen, —P(O)(OH)$_2$, and —$R^5$—O—P(O)(OH)$_2$; $R^5$ is a $C_1$-$C_4$-alkyl; $R^6$ is hydrogen or a $C_1$-$C_4$-alkyl; and provided that at least one of $R^1$ and $R^2$ is —P(O)(OH)$_2$ or —$R^5$—O—P(O)(OH)$_2$. In one aspect, the composition comprises a first compound corresponding in structure to Formula (I). In another aspect, the composition comprises a pharmaceutically acceptable salt of the first compound corresponding in structure to Formula (I).

In another embodiment, the pharmaceutical composition comprises a first compound corresponding in structure to Formula (I-a) or a pharmaceutically acceptable salt thereof, and a pharmaceutically acceptable carrier. In one aspect, the composition comprises a first compound corresponding in structure to Formula (I-a). In another aspect, the composition comprises a pharmaceutically acceptable salt of the first compound corresponding in structure to Formula (I-a).

In another embodiment, the pharmaceutical composition comprises a first compound corresponding in structure to Formula (I-b) or a pharmaceutically acceptable salt thereof, and a pharmaceutically acceptable carrier. In one aspect, the composition comprises a first compound corresponding in structure to Formula (I-b). In another aspect, the composition comprises a pharmaceutically acceptable salt of the first compound corresponding in structure to Formula (I-b).

In another embodiment, the pharmaceutical composition comprises a first compound corresponding in structure to Formula (I-c) or a pharmaceutically acceptable salt thereof, and a pharmaceutically acceptable carrier. In one aspect, the composition comprises a first compound corresponding in structure to Formula (I-c). In another aspect, the composition comprises a pharmaceutically acceptable salt of the first compound corresponding in structure to Formula (I-c).

In another embodiment, the pharmaceutical composition comprises a first compound corresponding in structure to Formula (I-d) or a pharmaceutically acceptable salt thereof, and a pharmaceutically acceptable carrier. In one aspect, the composition comprises a first compound corresponding in structure to Formula (I-d). In another aspect, the composition comprises a pharmaceutically acceptable salt of the first compound corresponding in structure to Formula (I-d).

In another embodiment, the pharmaceutical composition comprises a first compound corresponding in structure to Formula (I-e) or a pharmaceutically acceptable salt thereof, and a pharmaceutically acceptable carrier. In one aspect, the composition comprises a first compound corresponding in structure to Formula (I-e). In another aspect, the composition comprises a pharmaceutically acceptable salt of the first compound corresponding in structure to Formula (I-e).

In another embodiment, the pharmaceutical composition comprises a first compound corresponding in structure to Formula (I-f) or a pharmaceutically acceptable salt thereof, and a pharmaceutically acceptable carrier. In one aspect, the composition comprises a first compound corresponding in structure to Formula (I-f). In another aspect, the composition comprises a pharmaceutically acceptable salt of the first compound corresponding in structure to Formula (I-f).

In one embodiment, the pharmaceutical composition comprises a second compound corresponding in structure to Formula (II):

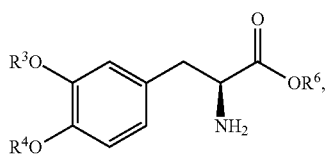

(II)

or a pharmaceutically acceptable salt thereof, wherein $R^3$ and $R^4$ are each independently selected from the group consisting of hydrogen, —P(O)(OH)$_2$, and —$R^5$—O—P(O)(OH)$_2$; $R^5$ is a $C_1$-$C_4$-alkyl; $R^6$ is hydrogen or a $C_1$-$C_4$-alkyl; and provided that at least one of $R^3$ and $R^4$ is —P(O)(OH)$_2$ or —$R^5$—O—P(O)(OH)$_2$. In one aspect, the composition comprises a second compound corresponding in structure to Formula (II). In another aspect, the composition comprises a pharmaceutically acceptable salt of the first compound corresponding in structure to Formula (II).

In another embodiment, the pharmaceutical composition comprises a second compound corresponding in structure to Formula (II-a) or a pharmaceutically acceptable salt thereof, and a pharmaceutically acceptable carrier. In one aspect, the composition comprises a second compound corresponding in structure to Formula (II-a). In another aspect, the composition comprises a pharmaceutically acceptable salt of the second compound corresponding in structure to Formula (II-a).

In another embodiment, the pharmaceutical composition comprises a second compound corresponding in structure to Formula (II-b) or a pharmaceutically acceptable salt thereof, and a pharmaceutically acceptable carrier. In one aspect, the composition comprises a second compound corresponding in structure to Formula (II-b). In another aspect, the composition comprises a pharmaceutically acceptable salt of the second compound corresponding in structure to Formula (II-b).

In another embodiment, the pharmaceutical composition comprises a second compound corresponding in structure to Formula (II-c) or a pharmaceutically acceptable salt thereof, and a pharmaceutically acceptable carrier. In one aspect, the composition comprises a second compound corresponding in structure to Formula (II-c). In another aspect, the composition comprises a pharmaceutically acceptable salt of the second compound corresponding in structure to Formula (II-c).

In another embodiment, the pharmaceutical composition comprises a second compound corresponding in structure to Formula (II-d) or a pharmaceutically acceptable salt thereof, and a pharmaceutically acceptable carrier. In one aspect, the composition comprises a second compound corresponding in structure to Formula (II-d). In another aspect, the composition comprises a pharmaceutically acceptable salt of the second compound corresponding in structure to Formula (II-d).

In another embodiment, the pharmaceutical composition comprises a second compound corresponding in structure to Formula (II-e) or a pharmaceutically acceptable salt thereof, and a pharmaceutically acceptable carrier. In one aspect, the composition comprises a second compound corresponding in structure to Formula (II-e). In another aspect, the composition comprises a pharmaceutically acceptable salt of the second compound corresponding in structure to Formula (II-e).

In another embodiment, the pharmaceutical composition comprises a first compound, a second compound, and a pharmaceutically acceptable carrier, wherein:

the first compound corresponds in structure to Formula (I):

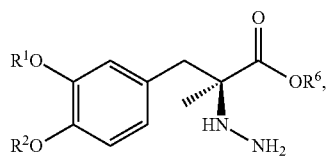

or a pharmaceutically acceptable salt thereof, wherein $R^1$ and $R^2$ are each independently selected from the group consisting of hydrogen, —P(O)(OH)$_2$, and —R$^5$—O—P(O)(OH)$_2$; R$^5$ is a C$_1$-C$_4$-alkyl; R$^6$ is hydrogen or a C$_1$-C$_4$-alkyl; and provided that at least one of $R^1$ and $R^2$ is —P(O)(OH)$_2$ or —R$^5$—O—P(O)(OH)$_2$; and the second compound corresponds in structure to Formula (II):

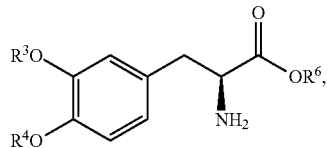

or a pharmaceutically acceptable salt thereof, wherein $R^3$ and $R^4$ are each independently selected from the group consisting of hydrogen, —P(O)(OH)$_2$, and —R$^5$—O—P(O)(OH)$_2$; R$^5$ is a C$_1$-C$_4$-alkyl; R$^6$ is hydrogen or a C$_1$-C$_4$-alkyl; and provided that at least one of $R^3$ and $R^4$ is —P(O)(OH)$_2$ or —R$^5$—O—P(O)(OH)$_2$.

The composition may independently comprise the first compound and the second compound as either the free form of the compound or a pharmaceutically acceptable salt of the compound. In one aspect, the composition comprises the free form of the first compound. In another aspect, the composition comprises a pharmaceutically acceptable salt of the first compound. In another aspect, the composition comprises the free form of the second compound. In another aspect, the composition comprises a pharmaceutically acceptable salt of the second compound. In another aspect, the composition comprises the free form of the first compound and the free form of the second compound. In another aspect, the composition comprises a pharmaceutically acceptable salt of the first compound and a pharmaceutically acceptable salt of the second compound.

In another embodiment, the pharmaceutical composition comprises a first compound, a second compound, and a pharmaceutically acceptable carrier, wherein:

the first compound corresponds in structure to Formula (I-a) or a pharmaceutically acceptable salt thereof; and the second compound corresponds in structure to Formula (II):

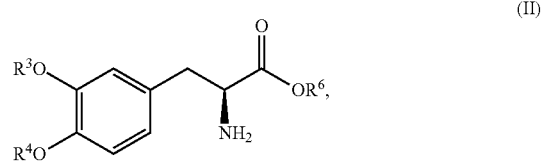

or a pharmaceutically acceptable salt thereof, wherein $R^3$ and $R^4$ are each independently selected from the group consisting of hydrogen, —P(O)(OH)$_2$, and —R$^5$—O—P(O)(OH)$_2$; R$^5$ is a C$_1$-C$_4$-alkyl; R$^6$ is hydrogen or a C$_1$-C$_4$-alkyl; and provided that at least one of $R^3$ and $R^4$ is —P(O)(OH)$_2$ or —R$^5$—O—P(O)(OH)$_2$.

In another embodiment, the pharmaceutical composition comprises a first compound, a second compound, and a pharmaceutically acceptable carrier, wherein:

the first compound corresponds in structure to Formula (I-b) or a pharmaceutically acceptable salt thereof; and the second compound corresponds in structure to Formula (II):

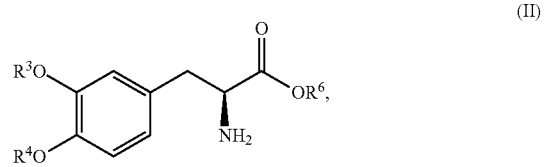

or a pharmaceutically acceptable salt thereof, wherein $R^3$ and $R^4$ are each independently selected from the group consisting of hydrogen, —P(O)(OH)$_2$, and —R$^5$—O—P(O)(OH)$_2$; R$^5$ is a C$_1$-C$_4$-alkyl; R$^6$ is hydrogen or a C$_1$-C$_4$-alkyl; and provided that at least one of $R^3$ and $R^4$ is —P(O)(OH)$_2$ or —R$^5$—O—P(O)(OH)$_2$.

In another embodiment, the pharmaceutical composition comprises a first compound, a second compound, and a pharmaceutically acceptable carrier, wherein:

the first compound corresponds in structure to Formula (I-c) or a pharmaceutically acceptable salt thereof; and the second compound corresponds in structure to Formula (II):

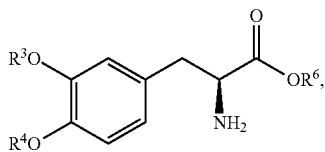

(II)

or a pharmaceutically acceptable salt thereof, wherein $R^3$ and $R^4$ are each independently selected from the group consisting of hydrogen, —P(O)(OH)$_2$, and —R$^5$—O—P(O)(OH)$_2$; $R^5$ is a $C_1$-$C_4$-alkyl; $R^6$ is hydrogen or a $C_1$-$C_4$-alkyl; and provided that at least one of $R^3$ and $R^4$ is —P(O)(OH)$_2$ or —R—O—P(O)(OH)$_2$.

In another embodiment, the pharmaceutical composition comprises a first compound, a second compound, and a pharmaceutically acceptable carrier, wherein:

the first compound corresponds in structure to Formula (I-d) or a pharmaceutically acceptable salt thereof; and the second compound corresponds in structure to Formula (II):

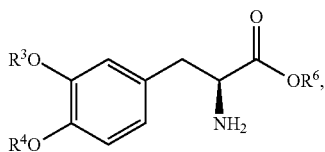

(II)

or a pharmaceutically acceptable salt thereof, wherein $R^3$ and $R^4$ are each independently selected from the group consisting of hydrogen, —P(O)(OH)$_2$, and —R$^5$—O—P(O)(OH)$_2$; $R^5$ is a $C_1$-$C_4$-alkyl; $R^6$ is hydrogen or a $C_1$-$C_4$-alkyl; and provided that at least one of $R^3$ and $R^4$ is —P(O)(OH)$_2$ or —R$^5$—O—P(O)(OH)$_2$.

In another embodiment, the pharmaceutical composition comprises a first compound, a second compound, and a pharmaceutically acceptable carrier, wherein:

the first compound corresponds in structure to Formula (I-e) or a pharmaceutically acceptable salt thereof; and the second compound corresponds in structure to Formula (II):

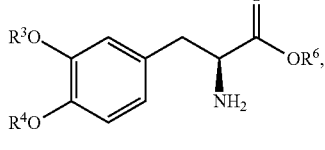

(II)

or a pharmaceutically acceptable salt thereof, wherein $R^3$ and $R^4$ are each independently selected from the group consisting of hydrogen, —P(O)(OH)$_2$, and —R$^5$—O—P(O)(OH)$_2$; $R^5$ is a $C_1$-$C_4$-alkyl; $R^6$ is hydrogen or a $C_1$-$C_4$-alkyl; and provided that at least one of $R^3$ and $R^4$ is —P(O)(OH)$_2$ or —R$^5$—O—P(O)(OH)$_2$.

In another embodiment, the pharmaceutical composition comprises a first compound, a second compound, and a pharmaceutically acceptable carrier, wherein:

the first compound corresponds in structure to Formula (I-f) or a pharmaceutically acceptable salt thereof; and the second compound corresponds in structure to Formula (II):

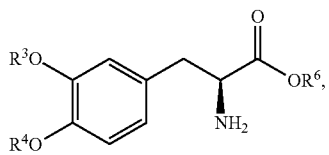

(II)

or a pharmaceutically acceptable salt thereof, wherein $R^3$ and $R^4$ are each independently selected from the group consisting of hydrogen, —P(O)(OH)$_2$, and —R$^5$—O—P(O)(OH)$_2$; $R^5$ is a $C_1$-$C_4$-alkyl; $R^6$ is hydrogen or a $C_1$-$C_4$-alkyl; and provided that at least one of $R^3$ and $R^4$ is —P(O)(OH)$_2$ or —R$^5$—O—P(O)(OH)$_2$.

In another embodiment, the pharmaceutical composition comprises a first compound, a second compound, and a pharmaceutically acceptable carrier, wherein:

the first compound corresponds in structure to Formula (I):

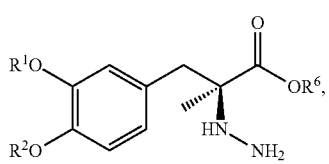

(I)

or a pharmaceutically acceptable salt thereof, wherein $R^1$ and $R^2$ are each independently selected from the group consisting of hydrogen, —P(O)(OH)$_2$, and —R$^5$—O—P(O)(OH)$_2$; $R^5$ is a $C_1$-$C_4$-alkyl; $R^6$ is hydrogen or a $C_1$-$C_4$-alkyl; and provided that at least one of $R^1$ and $R^2$ is —P(O)(OH)$_2$ or —R$^5$—O—P(O)(OH)$_2$; and the second compound corresponds in structure to Formula (II-a) or a pharmaceutically acceptable salt thereof.

In another embodiment, the pharmaceutical composition comprises a first compound, a second compound, and a pharmaceutically acceptable carrier, wherein:

the first compound corresponds in structure to Formula (I):

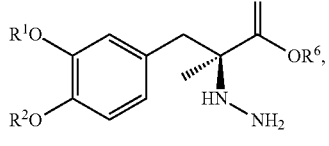

(I)

or a pharmaceutically acceptable salt thereof, wherein $R^1$ and $R^2$ are each independently selected from the group consisting of hydrogen, —P(O)(OH)$_2$, and —R$^5$—O—P(O)(OH)$_2$; $R^5$ is a $C_1$-$C_4$-alkyl; $R^6$ is hydrogen or a $C_1$-$C_4$-alkyl; and provided that at least one of $R^1$ and $R^2$ is —P(O)(OH)$_2$ or —R$^5$—O—P(O)(OH)$_2$; and the second compound corresponds in structure to Formula (II-b) or a pharmaceutically acceptable salt thereof.

In another embodiment, the pharmaceutical composition comprises a first compound, a second compound, and a pharmaceutically acceptable carrier, wherein:

the first compound corresponds in structure to Formula (I):

(I)

or a pharmaceutically acceptable salt thereof, wherein $R^1$ and $R^2$ are each independently selected from the group consisting of hydrogen, —P(O)(OH)$_2$, and —$R^5$—O—P(O)(OH)$_2$; $R^5$ is a $C_1$-$C_4$-alkyl; $R^6$ is hydrogen or a $C_1$-$C_4$-alkyl; and provided that at least one of $R^1$ and $R^2$ is —P(O)(OH)$_2$ or —$R^5$—O—P(O)(OH)$_2$; and the second compound corresponds in structure to Formula (II-c) or a pharmaceutically acceptable salt thereof.

In another embodiment, the pharmaceutical composition comprises a first compound, a second compound, and a pharmaceutically acceptable carrier, wherein:

the first compound corresponds in structure to Formula (I):

(I)

or a pharmaceutically acceptable salt thereof, wherein $R^1$ and $R^2$ are each independently selected from the group consisting of hydrogen, —P(O)(OH)$_2$, and —$R^5$—O—P(O)(OH)$_2$; $R^5$ is a $C_1$-$C_4$-alkyl; $R^6$ is hydrogen or a $C_1$-$C_4$-alkyl; and provided that at least one of $R^1$ and $R^2$ is —P(O)(OH)$_2$ or —$R^5$—O—P(O)(OH)$_2$; and the second compound corresponds in structure to Formula (II-d) or a pharmaceutically acceptable salt thereof.

In another embodiment, the pharmaceutical composition comprises a first compound, a second compound, and a pharmaceutically acceptable carrier, wherein:

the first compound corresponds in structure to Formula (I):

(I)

or a pharmaceutically acceptable salt thereof, wherein $R^1$ and $R^2$ are each independently selected from the group consisting of hydrogen, —P(O)(OH)$_2$, and —$R^5$—O—P(O)(OH)$_2$; $R^5$ is a $C_1$-$C_4$-alkyl; $R^6$ is hydrogen or a $C_1$-$C_4$-alkyl; and provided that at least one of $R^1$ and $R^2$ is —P(O)(OH)$_2$ or —$R^5$—O—P(O)(OH)$_2$; and the second compound corresponds in structure to Formula (II-e) or a pharmaceutically acceptable salt thereof.

In another embodiment, the pharmaceutical composition comprises a first compound, a second compound, and a pharmaceutically acceptable carrier, wherein:

the first compound corresponds in structure to Formula (I-a): or a pharmaceutically acceptable salt thereof; and the second compound corresponds in structure to Formula (II-a) or a pharmaceutically acceptable salt thereof.

In another embodiment, the pharmaceutical composition comprises a first compound, a second compound, and a pharmaceutically acceptable carrier, wherein:

the first compound corresponds in structure to Formula (I-b) or a pharmaceutically acceptable salt thereof; and the second compound corresponds in structure to Formula (II-a) or a pharmaceutically acceptable salt thereof.

In another embodiment, the pharmaceutical composition comprises a first compound, a second compound, and a pharmaceutically acceptable carrier, wherein:

the first compound corresponds in structure to Formula (I-c) or a pharmaceutically acceptable salt thereof; and the second compound corresponds in structure to Formula (II-a) or a pharmaceutically acceptable salt thereof.

In another embodiment, the pharmaceutical composition comprises a first compound, a second compound, and a pharmaceutically acceptable carrier, wherein:

the first compound corresponds in structure to Formula (I-d) or a pharmaceutically acceptable salt thereof; and the second compound corresponds in structure to Formula (II-a) or a pharmaceutically acceptable salt thereof.

In another embodiment, the pharmaceutical composition comprises a first compound, a second compound, and a pharmaceutically acceptable carrier, wherein:

the first compound corresponds in structure to Formula (I-e) or a pharmaceutically acceptable salt thereof; and the second compound corresponds in structure to Formula (II-a) or a pharmaceutically acceptable salt thereof.

In another embodiment, the pharmaceutical composition comprises a first compound, a second compound, and a pharmaceutically acceptable carrier, wherein:

the first compound corresponds in structure to Formula (I-f) or a pharmaceutically acceptable salt thereof; and the second compound corresponds in structure to Formula (II-a) or a pharmaceutically acceptable salt thereof.

In another embodiment, the pharmaceutical composition comprises a first compound, a second compound, and a pharmaceutically acceptable carrier, wherein:

the first compound corresponds in structure to Formula (I-a) or a pharmaceutically acceptable salt thereof; and the second compound corresponds in structure to Formula (II-b) or a pharmaceutically acceptable salt thereof.

In another embodiment, the pharmaceutical composition comprises a first compound, a second compound, and a pharmaceutically acceptable carrier, wherein:

the first compound corresponds in structure to Formula (I-b) or a pharmaceutically acceptable salt thereof; and the second compound corresponds in structure to Formula (II-b) or a pharmaceutically acceptable salt thereof.

In another embodiment, the pharmaceutical composition comprises a first compound, a second compound, and a pharmaceutically acceptable carrier, wherein:

the first compound corresponds in structure to Formula (I-c) or a pharmaceutically acceptable salt thereof; and the second compound corresponds in structure to Formula (II-b) or a pharmaceutically acceptable salt thereof.

In another embodiment, the pharmaceutical composition comprises a first compound, a second compound, and a pharmaceutically acceptable carrier, wherein:

the first compound corresponds in structure to Formula (I-d) or a pharmaceutically acceptable salt thereof; and the second compound corresponds in structure to Formula (II-b) or a pharmaceutically acceptable salt thereof.

In another embodiment, the pharmaceutical composition comprises a first compound, a second compound, and a pharmaceutically acceptable carrier, wherein:

the first compound corresponds in structure to Formula (I-e) or a pharmaceutically acceptable salt thereof; and the second compound corresponds in structure to Formula (II-b) or a pharmaceutically acceptable salt thereof.

In another embodiment, the pharmaceutical composition comprises a first compound, a second compound, and a pharmaceutically acceptable carrier, wherein:

the first compound corresponds in structure to Formula (I-f) or a pharmaceutically acceptable salt thereof; and the second compound corresponds in structure to Formula (II-b) or a pharmaceutically acceptable salt thereof.

In another embodiment, the pharmaceutical composition comprises a first compound, a second compound, and a pharmaceutically acceptable carrier, wherein:

the first compound corresponds in structure to Formula (I-a) or a pharmaceutically acceptable salt thereof; and the second compound corresponds in structure to Formula (II-c) or a pharmaceutically acceptable salt thereof.

In another embodiment, the pharmaceutical composition comprises a first compound, a second compound, and a pharmaceutically acceptable carrier, wherein:

the first compound corresponds in structure to Formula (I-b) or a pharmaceutically acceptable salt thereof; and the second compound corresponds in structure to Formula (II-c) or a pharmaceutically acceptable salt thereof.

In another embodiment, the pharmaceutical composition comprises a first compound, a second compound, and a pharmaceutically acceptable carrier, wherein:

the first compound corresponds in structure to Formula (I-c) or a pharmaceutically acceptable salt thereof; and the second compound corresponds in structure to Formula (II-c) or a pharmaceutically acceptable salt thereof.

In another embodiment, the pharmaceutical composition comprises a first compound, a second compound, and a pharmaceutically acceptable carrier, wherein:

the first compound corresponds in structure to Formula (I-d) or a pharmaceutically acceptable salt thereof; and the second compound corresponds in structure to Formula (II-c) or a pharmaceutically acceptable salt thereof.

In another embodiment, the pharmaceutical composition comprises a first compound, a second compound, and a pharmaceutically acceptable carrier, wherein:

the first compound corresponds in structure to Formula (I-e) or a pharmaceutically acceptable salt thereof; and the second compound corresponds in structure to Formula (II-c) or a pharmaceutically acceptable salt thereof.

In another embodiment, the pharmaceutical composition comprises a first compound, a second compound, and a pharmaceutically acceptable carrier, wherein:

the first compound corresponds in structure to Formula (I-f) or a pharmaceutically acceptable salt thereof; and the second compound corresponds in structure to Formula (II-c) or a pharmaceutically acceptable salt thereof.

In another embodiment, the pharmaceutical composition comprises a first compound, a second compound, and a pharmaceutically acceptable carrier, wherein:

the first compound corresponds in structure to Formula (I-a) or a pharmaceutically acceptable salt thereof; and the second compound corresponds in structure to Formula (II-d) or a pharmaceutically acceptable salt thereof.

In another embodiment, the pharmaceutical composition comprises a first compound, a second compound, and a pharmaceutically acceptable carrier, wherein:

the first compound corresponds in structure to Formula (I-b) or a pharmaceutically acceptable salt thereof; and the second compound corresponds in structure to Formula (II-d) or a pharmaceutically acceptable salt thereof.

In another embodiment, the pharmaceutical composition comprises a first compound, a second compound, and a pharmaceutically acceptable carrier, wherein:

the first compound corresponds in structure to Formula (I-c) or a pharmaceutically acceptable salt thereof; and the second compound corresponds in structure to Formula (II-d) or a pharmaceutically acceptable salt thereof.

In another embodiment, the pharmaceutical composition comprises a first compound, a second compound, and a pharmaceutically acceptable carrier, wherein:

the first compound corresponds in structure to Formula (I-d) or a pharmaceutically acceptable salt thereof; and the second compound corresponds in structure to Formula (II-d) or a pharmaceutically acceptable salt thereof.

In another embodiment, the pharmaceutical composition comprises a first compound, a second compound, and a pharmaceutically acceptable carrier, wherein:

the first compound corresponds in structure to Formula (I-e) or a pharmaceutically acceptable salt thereof; and the second compound corresponds in structure to Formula (II-d) or a pharmaceutically acceptable salt thereof.

In another embodiment, the pharmaceutical composition comprises a first compound, a second compound, and a pharmaceutically acceptable carrier, wherein:

the first compound corresponds in structure to Formula (I-f) or a pharmaceutically acceptable salt thereof; and the second compound corresponds in structure to Formula (II-d) or a pharmaceutically acceptable salt thereof.

In another embodiment, the pharmaceutical composition comprises a first compound, a second compound, and a pharmaceutically acceptable carrier, wherein:

the first compound corresponds in structure to Formula (I-a) or a pharmaceutically acceptable salt thereof; and the second compound corresponds in structure to Formula (II-e) or a pharmaceutically acceptable salt thereof.

In another embodiment, the pharmaceutical composition comprises a first compound, a second compound, and a pharmaceutically acceptable carrier, wherein:

the first compound corresponds in structure to Formula (I-b) or a pharmaceutically acceptable salt thereof; and the second compound corresponds in structure to Formula (II-e) or a pharmaceutically acceptable salt thereof.

In another embodiment, the pharmaceutical composition comprises a first compound, a second compound, and a pharmaceutically acceptable carrier, wherein:

the first compound corresponds in structure to Formula (I-c) or a pharmaceutically acceptable salt thereof; and the second compound corresponds in structure to Formula (II-e) or a pharmaceutically acceptable salt thereof.

In another embodiment, the pharmaceutical composition comprises a first compound, a second compound, and a pharmaceutically acceptable carrier, wherein:

the first compound corresponds in structure to Formula (I-d) or a pharmaceutically acceptable salt thereof; and the second compound corresponds in structure to Formula (II-e) or a pharmaceutically acceptable salt thereof.

In another embodiment, the pharmaceutical composition comprises a first compound, a second compound, and a pharmaceutically acceptable carrier, wherein:

the first compound corresponds in structure to Formula (I-e) or a pharmaceutically acceptable salt thereof; and the second compound corresponds in structure to Formula (II-e) or a pharmaceutically acceptable salt thereof.

In another embodiment, the pharmaceutical composition comprises a first compound, a second compound, and a pharmaceutically acceptable carrier, wherein: the first compound corresponds in structure to Formula (I-f) or a pharmaceutically acceptable salt thereof; and the second compound corresponds in structure to Formula (II-e) or a pharmaceutically acceptable salt thereof.

The pharmaceutical compositions of the present disclosure comprising both the first compound and the second compound generally will comprise the first compound and the second compound at a weight ratio from about 1:1 to about 1:50. In one aspect, the weight ratio is from about 1:2 to about 1:15. In another aspect, the weight ratio is from about 1:4 to about 1:10. In another aspect, the weight ratio is about 1:4. In another aspect, the weight ratio is about 1:7.5. In another aspect, the weight ratio is about 1:10.

B. Additional Excipients

The pharmaceutical compositions of the present disclosure optionally comprise one or more additional pharmaceutically acceptable excipients. The term "excipient" refers to any substance, not itself a therapeutic agent, used as a carrier or vehicle for delivery of a therapeutic agent to a subject or added to a pharmaceutical composition to improve its handling or storage properties or to permit or facilitate formation of a unit dose of the composition.

Excipients include, for example, antioxidants, agents to adjust the pH and osmolarity, preservatives, thickening agents, colorants, buffering agents, bacteriostats, and stabilizers. A given excipient, if present, generally will be present in an amount of about 0.001% to about 95%, about 0.01% to about 80%, about 0.02% to about 25%, or about 0.3% to about 10%, by weight.

In one embodiment, the pharmaceutical compositions optionally comprise an antioxidant. Suitable antioxidants for use in the pharmaceutical compositions include, for example, butylated hydroxytoluene, butylated hydroxyanisole, potassium metabisulfite, and the like.

In one embodiment, the pharmaceutical compositions optionally comprise a buffering agent. Buffering agents include agents that reduce pH changes. Suitable classes of buffering agents for use in various embodiments of the present invention comprise a salt of a Group IA metal including, for example, a bicarbonate salt of a Group IA metal, a carbonate salt of a Group IA metal, an alkaline or alkali earth metal buffering agent, an aluminum buffering agent, a calcium buffering agent, a sodium buffering agent, or a magnesium buffering agent. Suitable buffering agents further include carbonates, phosphates, bicarbonates, citrates, borates, acetates, phthalates, tartrates, succinates of any of the foregoing, for example, sodium or potassium phosphate, citrate, borate, acetate, bicarbonate and carbonate.

C. Dosage Forms

Solid Composition

In one embodiment, the pharmaceutical composition is a solid composition.

In another embodiment, the pharmaceutical composition is a solid composition that is suitable for oral administration. The first and second compound may be present as independent, separate solid dosage forms or combined in the same solid dosage form. Suitable solid dosage forms include capsules, tablets, pills, powders and granules. In such solid dosage forms, the first and/or second compound may be mixed with at least one inert, pharmaceutically acceptable excipient or carrier, such as sodium citrate or dicalcium phosphate and/or a) fillers or extenders such as starches, lactose, sucrose, glucose, mannitol and silicic acid; b) binders such as carboxymethylcellulose, alginates, gelatin, polyvinylpyrrolidone, sucrose and acacia; c) humectants such as glycerol; d) disintegrating agents such as agar-agar, calcium carbonate, potato or tapioca starch, alginic acid, certain silicates and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay and i) lubricants such as talc, calcium stearate, magnesium stearate, solid polyethylene glycols, sodium lauryl sulfate and mixtures thereof. In the case of capsules, tablets and pills, the dosage form may also comprise buffering agents.

Solid compositions of a similar type may also be employed as fillers in soft and hard-filled gelatin capsules using such carriers as lactose or milk sugar as well as high molecular weight polyethylene glycols and the like.

The solid dosage forms of tablets, dragees, capsules, pills and granules can be prepared with coatings and shells such as enteric coatings and other coatings well-known in the pharmaceutical formulating art. They may optionally contain opacifying agents and may also be of a composition such that they release the active ingredient(s) only, or preferentially, in a certain part of the intestinal tract, optionally, in a delayed manner. Examples of embedding compositions which can be used include polymeric substances and waxes.

The first and/or second compounds can also be in microencapsulated form (separately or together), if appropriate, with one or more of the above-mentioned carriers.

Liquid Composition

In one embodiment, the pharmaceutical composition is a liquid composition. In one aspect, the composition comprises water and is suitable for infusion.

In another embodiment, the pharmaceutical composition is a liquid composition that is suitable for intragastric, intestinal (e.g., intraduodenum, intrajejunum), intranasal, subcutaneous, intramuscular or intravenous administration. In one aspect, the composition is suitable for intragastric administration. In another aspect, the composition is suitable for subcutaneous administration. In another aspect, the composition is suitable for intramuscular administration. In another aspect, the composition is suitable for intravenous administration. In another aspect, the composition is suitable for intestinal administration. In another aspect, the composition is suitable for intraduodenum administration. In another aspect, the composition is suitable for intrajejunum administration. In another aspect, the composition is suitable for intranasal administration.

In another embodiment, the pharmaceutical composition is an aqueous pharmaceutical composition having an L-dopa prodrug concentration of at least about 5 mg/mL. In one aspect, the L-dopa prodrug concentration is at least about 10 mg/mL. In another aspect, the L-dopa prodrug concentration is at least about 20 mg/mL. In another aspect, the L-dopa prodrug concentration is at least about 30 mg/mL. In another aspect, the L-dopa prodrug concentration is at least about 50 mg/mL. In another aspect, the L-dopa prodrug concentration is at least about 100 mg/mL. In another aspect, the L-dopa prodrug concentration is at least about 150 mg/mL. In another aspect, the L-dopa prodrug concentration is at least about 200 mg/mL. In another aspect, the L-dopa prodrug concentration is at least about 250 mg/mL. In another aspect, the L-dopa prodrug concentration is at least about 300 mg/mL. In another aspect, the L-dopa prodrug concentration is at least about 350 mg/mL. In another aspect, the L-dopa prodrug concentration is at least about 400 mg/mL. In particular, the above L-dopa prodrug concentrations may be L-dopa phosphate prodrug concentrations, more particularly L-dopa 3'-monophosphate prodrug, L-dopa 4'-monophosphate prodrug and/or L-dopa 3',4'-diphosphate prodrug concentrations.

In another embodiment, the pharmaceutical composition is an aqueous pharmaceutical composition having a carbidopa prodrug concentration of at least about 5 mg/mL. In one aspect, the carbidopa prodrug concentration is at least about 10 mg/mL. In another aspect, the carbidopa prodrug concentration is at least about 20 mg/mL. In another aspect, the carbidopa prodrug concentration is at least about 30 mg/mL. In another aspect, the carbidopa prodrug concentration is at least about 50 mg/mL. In another aspect, the carbidopa prodrug concentration is at least about 100 mg/mL. In another aspect, the carbidopa prodrug concentration is at least about 150 mg/mL. In another aspect, the carbidopa prodrug concentration is at least about 200 mg/mL. In particular, the above carbidopa prodrug concentrations may be carbidopa phosphate prodrug concentrations, more particularly carbidopa 3'-monophosphate prodrug, carbidopa 4'-monophosphate prodrug and/or carbidopa 3',4'-diphosphate prodrug concentrations.

D. pH Level

In one embodiment, the pharmaceutical compositions may have a pH of $\geq$~2.0, $\geq$~2.5, $\geq$~3.0, $\geq$~3.5, $\geq$~4.0, $\geq$~4.5, $\geq$~5.0, $\geq$~5.5, $\geq$~6.0, $\geq$~6.2, $\geq$~6.4, $\geq$~6.5, $\geq$~6.6, $\geq$~6.8, $\geq$~7.0, $\geq$~7.1, $\geq$~7.2, $\geq$~7.3, $\geq$~7.4, $\geq$~7.5, $\geq$~7.6, $\geq$~7.7, $\geq$~7.8, $\geq$~7.9, $\geq$~8.0, $\geq$~8.2, $\geq$~8.4, $\geq$~8.6, $\geq$~8.8, or $\geq$~9.0. Particularly, the pH is $\geq$~7.4. Ranges expressly disclosed include combinations of any of the above-enumerated values, e.g., ~2.0 to ~7.5, ~6.0 to ~9.0, ~6.4 to ~7.7, ~7.0 to ~7.9, ~7.3 to ~8.2, etc. In one aspect the pH is from about 2 to about 8. In one aspect, the pH is from about 2.0 to about 7.5. In another aspect, the pH is from about 3.0 to about 7.5. In another aspect, the pH is from about 4.0 to about 7.5. In another aspect, the pH is from about 5.0 to about 7.5. In another aspect, the pH is from about 6.0 to about 7.5.

E. Stability

In another embodiment, the first compound (e.g., the phosphate prodrugs) and the second compound (e.g., the phosphate prodrugs) in the pharmaceutical compositions advantageously may remain stable in liquid compositions (e.g., aqueous solutions) at the above-described pHs for $\geq$~24 hours, $\geq$~36 hours, $\geq$~48 hours, $\geq$~60 hours, $\geq$~72 hours, $\geq$~84 hours, $\geq$~96 hours, $\geq$~108 hours, $\geq$~120 hours, $\geq$~132 hours, $\geq$~136 hours, $\geq$~144 hours, $\geq$156 hours, $\geq$~168 hours, or $\geq$~180 hours. Particularly, the pharmaceutical compositions may remain stable in aqueous solutions for $\geq$~24 hours at a pH of ~6 to ~8. Ranges expressly disclosed include combinations of any of the above-enumerated values, e.g., ~24 hours to ~180 hours, ~24 hours to ~168 hours, ~36 hours to ~72 hours, etc. Such increased stability is important for liquid compositions of the pharmaceutical compositions because typically the liquid compositions are stored prior to administration (e.g., intragastric, subcutaneous, intrajejunum, intranasal, intramuscular and/or intravenous), and thus, the first compound and the second compound must remain stable and not degrade significantly during the course of storage.

F. Solubility

In another embodiment, the first compound (e.g., the phosphate prodrugs) and the second compound (e.g., the phosphate prodrugs) in the pharmaceutical compositions unexpectedly have increased solubility in liquid compositions (e.g., aqueous solutions). For example, the first compound and/or the second compound may have a solubility at a pH of about ~5 to ~8, or more particularly at about a neutral pH of about 6.9 to about 7.5, of $\geq$~90 mg/mL, $\geq$~100 mg/mL, $\geq$~110 mg/mL, $\geq$~120 mg/mL, $\geq$~130 mg/mL, $\geq$~140 mg/mL, $\geq$~150 mg/mL, $\geq$~160 mg/mL, $\geq$~170 mg/mL, $\geq$~180 mg/mL, $\geq$~190 mg/mL, $\geq$~200 mg/mL, $\geq$~210 mg/mL, $\geq$~220 mg/mL, $\geq$~230 mg/mL, $\geq$~240 mg/mL, $\geq$~250 mg/mL, $\geq$~260 mg/mL, $\geq$~270 mg/mL, $\geq$~280 mg/mL, $\geq$~290 mg/mL, $\geq$~300 mg/mL, $\geq$~310 mg/mL, $\geq$~320 mg/mL, $\geq$~330 mg/mL, $\geq$~340 mg/mL, $\geq$~350 mg/mL, $\geq$~360 mg/mL, $\geq$~370 mg/mL, $\geq$~380 mg/mL, $\geq$~390 mg/mL, $\geq$~400 mg/mL, $\geq$~410 mg/mL, $\geq$~420 mg/mL, $\geq$~430 mg/mL, $\geq$~440 mg/mL, $\geq$~450 mg/mL, $\geq$~460 mg/mL, $\geq$~470 mg/mL, $\geq$~480 mg/mL, $\geq$~490 mg/mL, or $\geq$~500 mg/mL. Ranges expressly disclosed include combinations of any of the above-enumerated values, e.g., ~90 mg/mL to ~500 mg/mL, ~100 mg/mL to ~300 mg/mL, ~200 mg/mL to ~500 mg/mL, etc. In particular, the first compound has a solubility at a neutral pH, for example of about 7.4, of $\geq$~160 mg/mL, particularly $\geq$~200 mg/mL. In particular, the second compound has a solubility at a neutral pH, for example about 7.4, of $\geq$~370 mg/mL, particularly $\geq$~400 mg/mL. This increased solubility allows for higher concentrations of the first compound and/or second compound in the pharmaceutical composition, which leads to more effective and higher systemic levels of the first compound and/or second compound once administered to a patient.

G. Hydrazine Release

The first compound (e.g., the phosphate prodrugs) and/or second compound (e.g., the phosphate prodrugs) may release amounts of hydrazine, which is a carcinogen. Thus, it is important to reduce the release of hydrazine from the pharmaceutical compositions. It has been unexpectedly found that the pharmaceutical compositions described herein at a pH of ~5 to ~8 (e.g., 7.4) release hydrazine in amounts of $\leq$~60 ppm/hr, $\leq$~55 ppm/hr, $\leq$~50 ppm/hr, $\leq$~45 ppm/hr, $\leq$~40 ppm/hr, $\leq$~35 ppm/hr, $\leq$~30 ppm/hr, $\leq$~25 ppm/hr, $\leq$~20 ppm/hr, $\leq$~15 ppm/hr, $\leq$~10 ppm/hr, $\leq$~5 ppm/hr, $\leq$~4 ppm/hr, $\leq$~3 ppm/hr, $\leq$~2 ppm/hr, $\leq$~1 ppm/hr, or $\leq$~0.5 ppm/hr. Ranges expressly disclosed include combinations of any of the above-enumerated values, e.g., ~0.5 to ~60 ppm/hr, ~1 ppm/hr to ~40 ppm/hr, ~1 ppm/hr to ~10 ppm/hr, 2 ppm/hr to ~4 ppm/hr, etc. Particularly, the pharmaceutical compositions release less than ~1 ppm/hr of hydrazine.

H. Ready-to-Use

In still other embodiments, the present disclosure relates to a ready-to-use vial or cartridge or container or enclosure suitable for liquid pharmaceutical dosage formulation containment. Such containment may serve the function of holding a liquid formulation containing one or more carbidopa prodrugs and/or one or more L-dopa prodrugs. The vials can also serve as storage for powder forms of the carbidopa prodrug(s) and/or L-dopa prodrug(s) such that the vial can be in a ready to use format wherein reconstitution with an aqueous vehicle results in a ready to withdraw or load injection to the patient.

I. Pharmaceutical Combinations

As mentioned above, a pharmaceutical combination comprising the first compound and the second compound is also disclosed herein. The first compound or pharmaceutically acceptable salt thereof, and the second compound or pharmaceutically acceptable salt thereof can both be present in one pharmaceutical composition or can be present in separate pharmaceutical compositions. If separate they can be co-administered as more fully discussed herein.

Thus, in one embodiment a pharmaceutical combination comprising a first compound corresponding in structure to Formula (I):

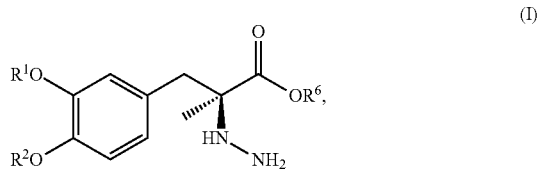

or a pharmaceutically acceptable salt thereof, wherein $R^1$ and $R^2$ are each independently selected from the group consisting of hydrogen, —P(O)(OH)$_2$, and —R$^5$—O—P(O)(OH)$_2$; $R^5$ is a $C_1$-$C_4$-alkyl; $R^6$ is hydrogen or a $C_1$-$C_4$-alkyl; and provided that at least one of $R^1$ and $R^2$ is —P(O)(OH)$_2$ or —R$^5$—O—P(O)(OH)$_2$; and a second compound corresponding in structure Formula (II):

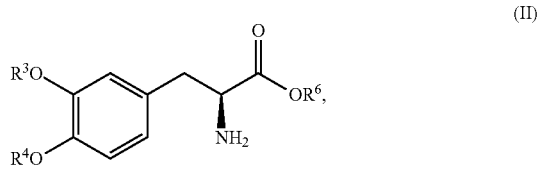

or a pharmaceutically acceptable salt thereof, wherein $R^3$ and $R^4$ are each independently selected from the group consisting of hydrogen, —P(O)(OH)$_2$, and —R$^5$—O—P(O)(OH)$_2$; $R^5$ is a $C_1$-$C_4$-alkyl; $R^6$ is hydrogen or a $C_1$-$C_4$-alkyl; and provided that at least one of $R^3$ and $R^4$ is —P(O)(OH)$_2$ or —R$^5$—O—P(O)(OH)$_2$ is provided herein.

V. METHODS OF TREATMENT

The present disclosure further relates to methods of treating Parkinson's disease and associated conditions comprising administering an effective amount of a carbidopa prodrug and an L-dopa prodrug to a patient.

In some embodiments, the methods of treating Parkinson's disease and associated conditions include providing a rescue therapy for treatment of Parkinson's disease and associated conditions. The term "rescue therapy" as used herein is any acute and intermittent therapy that may be used to treat the sudden re-immergence of motor symptoms (e.g. sudden "off" episode or "end-of-dose wearing off" and unpredictable "on/off" episodes). Patients with disabling motor complications can cycle between "off" time, which is defined as periods of poor mobility, slowness, and stiffness, and "on" time, which is defined as periods of good motor system control without troublesome dyskinesia.

In some embodiments, the carbidopa phosphate prodrug and the L-dopa prodrug are administered to the patient in the form of a pharmaceutical composition comprising both prodrugs. In other embodiments, the carbidopa prodrug and the L-dopa prodrug are separately administered to the patient.

A. First Compound and Second Compound and Combinations Thereof

In one embodiment, the present disclosure relates to a method of treating a condition in a subject (e.g. patient) in need of such treatment, wherein the method comprises administering to the patient a pharmaceutical combination comprising a first compound and a second compound, wherein:

the first compound corresponds in structure to Formula (I):

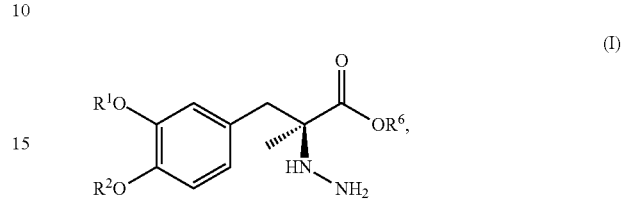

or a pharmaceutically acceptable salt thereof, wherein $R^1$ and $R^2$ are each independently selected from the group consisting of hydrogen, —P(O)(OH)$_2$, and —R$^5$—O—P(O)(OH)$_2$; $R^5$ is a $C_1$-$C_4$-alkyl; $R^6$ is hydrogen or a $C_1$-$C_4$-alkyl; and provided that at least one of $R^1$ and $R^2$ is —P(O)(OH)$_2$ or —R$^5$—O—P(O)(OH)$_2$;

the second compound corresponds in structure to Formula (II):

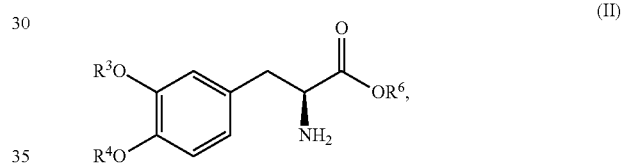

or a pharmaceutically acceptable salt thereof, wherein $R^3$ and $R^4$ are each independently selected from the group consisting of hydrogen, —P(O)(OH)$_2$, and —R$^5$—O—P(O)(OH)$_2$; wherein $R^5$ is a $C_1$-$C_4$-alkyl; $R^6$ is hydrogen or a $C_1$-$C_4$-alkyl; and provided that at least one of $R^3$ and $R^4$ is —P(O)(OH)$_2$ or —R$^5$—O—P(O)(OH)$_2$.

In one embodiment, the first compound and the second compound are administered in amounts that together provide a therapeutically effect for the subject (e.g. patient).

In one embodiment, the first compound corresponds in structure to Formula (I-a), and the second compound corresponds in structure to Formula (II-a).

In another embodiment, the first compound corresponds in structure to Formula (I-b), and the second compound corresponds in structure to Formula (II-a).

In another embodiment, the first compound corresponds in structure to Formula (I-c), and the second compound corresponds in structure to Formula (II-a).

In another embodiment, the first compound corresponds in structure to Formula (I-d), and the second compound corresponds in structure to Formula (II-a).

In another embodiment, the first compound corresponds in structure to Formula (I-e), and the second compound corresponds in structure to Formula (II-a).

In another embodiment, the first compound corresponds in structure to Formula (I-f), and the second compound corresponds in structure to Formula (II-a).

In another embodiment, the first compound corresponds in structure to Formula (I-a), and the second compound corresponds in structure to Formula (II-b).

In another embodiment, the first compound corresponds in structure to Formula (I-b), and the second compound corresponds in structure to Formula (II-b).

In another embodiment, the first compound corresponds in structure to Formula (I-c), and the second compound corresponds in structure to Formula (II-b).

In another embodiment, the first compound corresponds in structure to Formula (I-d), and the second compound corresponds in structure to Formula (II-b).

In another embodiment, the first compound corresponds in structure to Formula (I-e), and the second compound corresponds in structure to Formula (II-b).

In another embodiment, the first compound corresponds in structure to Formula (I-f), and the second compound corresponds in structure to Formula (II-b).

In another embodiment, the first compound corresponds in structure to Formula (I-a), and the second compound corresponds in structure to Formula (II-c).

In another embodiment, the first compound corresponds in structure to Formula (I-b), and the second compound corresponds in structure to Formula (II-c).

In another embodiment, the first compound corresponds in structure to Formula (I-c), and the second compound corresponds in structure to Formula (II-c).

In another embodiment, the first compound corresponds in structure to Formula (I-d), and the second compound corresponds in structure to Formula (II-c).

In another embodiment, the first compound corresponds in structure to Formula (I-e), and the second compound corresponds in structure to Formula (II-c).

In another embodiment, the first compound corresponds in structure to Formula (I-f), and the second compound corresponds in structure to Formula (II-c).

In another embodiment, the first compound corresponds in structure to Formula (I-a), and the second compound corresponds in structure to Formula (II-d).

In another embodiment, the first compound corresponds in structure to Formula (I-b), and the second compound corresponds in structure to Formula (II-d).

In another embodiment, the first compound corresponds in structure to Formula (I-c), and the second compound corresponds in structure to Formula (II-d).

In another embodiment, the first compound corresponds in structure to Formula (I-d), and the second compound corresponds in structure to Formula (II-d).

In another embodiment, the first compound corresponds in structure to Formula (I-e), and the second compound corresponds in structure to Formula (II-d).

In another embodiment, the first compound corresponds in structure to Formula (I-f), and the second compound corresponds in structure to Formula (II-d).

In another embodiment, the first compound corresponds in structure to Formula (I-a), and the second compound corresponds in structure to Formula (II-e).

In another embodiment, the first compound corresponds in structure to Formula (I-b), and the second compound corresponds in structure to Formula (II-e).

In another embodiment, the first compound corresponds in structure to Formula (I-c), and the second compound corresponds in structure to Formula (II-e).

In another embodiment, the first compound corresponds in structure to Formula (I-d), and the second compound corresponds in structure to Formula (II-e).

In another embodiment, the first compound corresponds in structure to Formula (I-e), and the second compound corresponds in structure to Formula (II-e).

In another embodiment, the first compound corresponds in structure to Formula (I-f), and the second compound corresponds in structure to Formula (II-e).

B. Conditions Treated

In one embodiment, the condition treated by administering the first compound and the second compound is Parkinson's disease.

In another embodiment, the condition treated by administering the first compound and the second compound is sleep disturbance in a patient with Parkinson's disease (i.e., a method of reducing sleep disturbance in a patient with Parkinson's disease).

In another embodiment, the condition treated by administering the first compound and the second compound is impaired motor performance in a patient with Parkinson's disease (i.e., a method of improving motor performance in a patient with Parkinson's disease).

In another embodiment, the condition treated by administering the first compound and the second compound is nighttime disability in a patient with Parkinson's disease (i.e., a method of reducing nighttime disabilities in a patient with Parkinson's disease).

In another embodiment, the first compound and the second compound are administered to treat motor fluctuations in a patient with Parkinson's disease.

In another embodiment, the first compound and the second compound are administered to treat dyskinesia in a patient with Parkinson's disease.

In another embodiment, the first compound and the second compound are administered to delay the onset of motor fluctuations in a patient with Parkinson's disease.

In another embodiment, the first compound and the second compound are administered to delay the onset of dyskinesia in a patient with Parkinson's disease.

C. Administering a Pharmaceutical Composition

In one embodiment, the present disclosure relates to a method of treating a condition in need of treatment, wherein the method comprises administering to a subject (e.g. patient) a therapeutically effective amount of a pharmaceutical composition of the present disclosure.

In one embodiment, the composition administered comprises a first compound corresponding in structure to Formula (I-a), and a second compound corresponding in structure to Formula (II-a).

In another embodiment, the composition administered comprises a first compound corresponding in structure to Formula (I-b), and a second compound corresponding in structure to Formula (II-a).

In another embodiment, the composition administered comprises a first compound corresponding in structure to Formula (I-c), and a second compound corresponding in structure to Formula (II-a).

In another embodiment, the composition administered comprises a first compound corresponding in structure to Formula (I-d), and a second compound corresponding in structure to Formula (II-a).

In another embodiment, the composition administered comprises a first compound corresponding in structure to Formula (I-e), and a second compound corresponding in structure to Formula (II-a).

In another embodiment, the composition administered comprises a first compound corresponding in structure to Formula (I-f), and a second compound corresponding in structure to Formula (II-a).

In another embodiment, the composition administered comprises a first compound corresponding in structure to Formula (I-a), and a second compound corresponding in structure to Formula (II-b).

In another embodiment, the composition administered comprises a first compound corresponding in structure to Formula (I-b), and a second compound corresponding in structure to Formula (II-b).

In another embodiment, the composition administered comprises a first compound corresponding in structure to Formula (I-c), and a second compound corresponding in structure to Formula (II-b).

In another embodiment, the composition administered comprises a first compound corresponding in structure to Formula (I-d), and a second compound corresponding in structure to Formula (II-b).

In another embodiment, the composition administered comprises a first compound corresponding in structure to Formula (I-e), and a second compound corresponding in structure to Formula (II-b).

In another embodiment, the composition administered comprises a first compound corresponding in structure to Formula (I-f), and a second compound corresponding in structure to Formula (II-b).

In another embodiment, the composition administered comprises a first compound corresponding in structure to Formula (I-a), and a second compound corresponding in structure to Formula (II-c).

In another embodiment, the composition administered comprises a first compound corresponding in structure to Formula (I-b), and a second compound corresponding in structure to Formula (II-c).

In another embodiment, the composition administered comprises a first compound corresponding in structure to Formula (I-c), and a second compound corresponding in structure to Formula (II-c).

In another embodiment, the composition administered comprises a first compound corresponding in structure to Formula (I-d), and a second compound corresponding in structure to Formula (II-c).

In another embodiment, the composition administered comprises a first compound corresponding in structure to Formula (I-e), and a second compound corresponding in structure to Formula (II-c).

In another embodiment, the composition administered comprises a first compound corresponding in structure to Formula (I-f), and a second compound corresponding in structure to Formula (II-c).

In another embodiment, the composition administered comprises a first compound corresponding in structure to Formula (I-a), and a second compound corresponding in structure to Formula (II-d).

In another embodiment, the composition administered comprises a first compound corresponding in structure to Formula (I-b), and a second compound corresponding in structure to Formula (II-d).

In another embodiment, the composition administered comprises a first compound corresponding in structure to Formula (I-c), and a second compound corresponding in structure to Formula (II-d).

In another embodiment, the composition administered comprises a first compound corresponding in structure to Formula (I-d), and a second compound corresponding in structure to Formula (II-d).

In another embodiment, the composition administered comprises a first compound corresponding in structure to Formula (I-e), and a second compound corresponding in structure to Formula (II-d).

In another embodiment, the composition administered comprises a first compound corresponding in structure to Formula (I-f), and a second compound corresponding in structure to Formula (II-d).

In another embodiment, the composition administered comprises a first compound corresponding in structure to Formula (I-a), and a second compound corresponding in structure to Formula (II-e).

In another embodiment, the composition administered comprises a first compound corresponding in structure to Formula (I-b), and a second compound corresponding in structure to Formula (II-e).

In another embodiment, the composition administered comprises a first compound corresponding in structure to Formula (I-c), and a second compound corresponding in structure to Formula (II-e).

In another embodiment, the composition administered comprises a first compound corresponding in structure to Formula (I-d), and a second compound corresponding in structure to Formula (II-e).

In another embodiment, the composition administered comprises a first compound corresponding in structure to Formula (I-e), and a second compound corresponding in structure to Formula (II-e).

In another embodiment, the composition administered comprises a first compound corresponding in structure to Formula (I-f), and a second compound corresponding in structure to Formula (II-e).

D. Conditions Treated

In one embodiment, the condition treated by administering the pharmaceutical composition is Parkinson's disease.

In another embodiment, the condition treated by administering the pharmaceutical composition is sleep disturbance in a patient with Parkinson's disease (i.e., a method of reducing sleep disturbance in a patient with Parkinson's disease).

In another embodiment, the condition treated by administering the pharmaceutical composition is impaired motor performance in a patient with Parkinson's disease (i.e., a method of improving motor performance in a patient with Parkinson's disease).

In another embodiment, the pharmaceutical composition is administered to treat motor fluctuations in a patient with Parkinson's disease.

In another embodiment, the pharmaceutical composition is administered to treat dyskinesia in a patient with Parkinson's disease.

In another embodiment, the pharmaceutical composition is administered to delay the onset of motor fluctuations in a patient with Parkinson's disease.

In another embodiment, the pharmaceutical composition is administered to delay the onset of dyskinesia in a patient with Parkinson's disease.

In another embodiment, the condition treated by administering the pharmaceutical composition is nighttime disability in a patient with Parkinson's disease (i.e., a method of reducing nighttime disabilities in a patient with Parkinson's disease).

E. Weight Ratios and Administration Routes

In general, the weight ratio of the first compound (e.g., the phosphate prodrugs) and the second compound (e.g., the phosphate prodrugs) administered to the patient (either separately or together in a single pharmaceutical composition) is from about 1:1 to about 1:50. In one aspect, the weight ratio is from about 1:2 to about 1:15. In another aspect, the weight ratio is from about 1:4 to about 1:10. In another aspect, the weight ratio is about 1:4. In another aspect, the weight ratio is about 1:7.5. In another aspect, the weight ratio is about 1:10.

In one embodiment, the first compound (e.g., the phosphate prodrugs) and the second compound (e.g., the phosphate prodrugs) are administered to the patient in the form of a solid composition (or solid compositions). In one aspect, the composition is suitable for oral administration.

In one embodiment, the first compound (e.g., the phosphate prodrugs) and the second compound (e.g., the phosphate prodrugs) are administered to the patient in the form of a liquid composition (or liquid compositions). In one aspect, the composition comprises water and is suitable for infusion.

In another embodiment, the first compound (e.g., the phosphate prodrugs) and the second compound (e.g., the phosphate prodrugs) are administered to the patient as a liquid composition (either separately or in the same pharmaceutical composition) that is suitable for intragastric, subcutaneous, intranasal, intramuscular or intravenous administration. In one aspect, the liquid composition(s) is suitable for intragastric administration. In another aspect, the liquid composition(s) is suitable for subcutaneous administration. In another aspect, the liquid composition(s) is suitable for intramuscular administration. In another aspect, the liquid composition(s) is suitable for intravenous administration. In another aspect, the liquid composition(s) is suitable for intranasal administration.

In another embodiment, the first compound (e.g., the phosphate prodrugs) and the second compound (e.g., the phosphate prodrugs) are administered via intestinal administration (e.g., intrajejunum, intraduodenum) (either separately or in the same pharmaceutical composition). They can be administered (or "infused") directly into the intestine, e.g., duodenum or the jejunum by a permanent tube inserted via percutaneous endoscopic gastrostomy, for example, with an outer transabdominal tube and an inner intestinal tube. In one aspect, the first compound (e.g., the phosphate prodrugs) and the second compound (e.g., the phosphate prodrugs) are administered via a tube inserted by radiological gastrojejunostomy. In another aspect, the first compound (e.g., the phosphate prodrugs) and the second compound (e.g., the phosphate prodrugs) are administered via a temporary nasoduodenal tube that is inserted into the patient initially to determine if the patient responds favorably to the treatment method before the permanent tube is inserted.

In some embodiments where the first compound (e.g., the phosphate prodrugs) and the second compound (e.g., the phosphate prodrugs) are administered via intestinal administration, administration can be carried out using a portable pump, such as the pump sold under the trade name, CADD-Legacy Duodopa® Pump®. Specifically, a cassette, pouch, or vial comprising the first compound (e.g., the phosphate prodrugs) and the second compound (e.g., the phosphate prodrugs) can be attached to the pump to create the delivery system. The delivery system is then connected to the nasoduodenal tube, the transabdominal port, the duodenal tube, or the jejunum tube for intestinal administration.

In one embodiment, the method comprises administering the first compound (e.g., the phosphate prodrugs) and the second compound (e.g., the phosphate prodrugs) (either together or separately) to the patient substantially continuously over a period of at least about 12 hours. In additional aspects, the first compound (e.g., the phosphate prodrugs) and the second compound (e.g., the phosphate prodrugs) are administered substantially continuously over a period of at least about 16 hours, at least about 24 hours, about 2 days, about 3 days, about 4 days, about 5 days, about 6 days, about one week, or longer. In particular, the first compound (e.g., the phosphate prodrugs) and the second compound (e.g., the phosphate prodrugs) may be subcutaneously administered substantially continuously over a period of at least about 16 hours.

F. Dosing and Plasma Concentrations

In one embodiment, the dosing of the first compound (e.g., the phosphate prodrugs) and the second compound (e.g., the phosphate prodrugs) administered to the patient is adjusted to optimize the clinical response achieved by a subject (e.g. patient), which means maximizing the functional ON-time during the day by minimizing the number and duration of OFF-time episodes (i.e., bradykinesia) and minimizing ON-time with disabling dyskinesia.

In one embodiment, the daily dose of the L-dopa prodrug (i.e., the second compound) administered to the patient according to methods of the present disclosure may be, for example, about 20 to about 1000000 mg, about 20 to about 100000 mg, about 20 to about 10000 mg, about 20 to about 5000 mg, about 20 mg to about 4000 mg, about 20 mg to about 3000 mg, about 20 mg to about 2000 mg, or about 20 mg to about 1000 mg per day. In particular, L-dopa phosphate prodrug, more particularly L-dopa 3'-monophosphate prodrug, L-dopa 4'-monophosphate prodrug and/or L-dopa 3',4'-diphosphate prodrug are administered in the above daily doses.

In one embodiment, the daily dose of the carbidopa prodrug (i.e., the first compound) administered to the patient according to methods of the present disclosure may be, for example, 0 mg to about 2500 mg, 0 mg to about 1250 mg, 0 mg to about 1000 mg, 0 mg to about 750 mg, 0 mg to about 625 mg, 0 mg to about 500 mg, 0 mg to about 375 mg, 0 mg to about 250 mg, or 5 mg to about 125 mg per day. In particular, carbidopa phosphate prodrug, more particularly carbidopa 3'-monophosphate prodrug, carbidopa 4'-monophosphate prodrug and/or carbidopa 3',4'-diphosphate prodrug are administered in the above daily doses.

In some embodiments, an amount of the first compound and an amount of the second compound are administered such that in combination they are sufficient to achieve an L-dopa plasma level in the patient of at least about 100 ng/mL. In one aspect, the L-dopa plasma level is at least about 200 ng/mL. In another aspect, the L-dopa plasma level is at least about 300 ng/mL. In another aspect, the L-dopa plasma level is at least about 400 ng/mL. In another aspect, the L-dopa plasma level is at least about 500 ng/mL. In another aspect, the L-dopa plasma level is at least about 600 ng/mL. In another aspect, the L-dopa plasma level is at least about 700 ng/mL. In another aspect, the L-dopa plasma level is at least about 800 ng/mL. In another aspect, the L-dopa plasma level is at least about 900 ng/mL. In another aspect, the L-dopa plasma level is at least about 1,000 ng/mL. In another aspect, the L-dopa plasma level is at least about 1,500 ng/mL. In another aspect, the L-dopa plasma level is at least about 2,000 ng/mL. In another aspect, the L-dopa plasma level is at least about 3,000 ng/mL. In another aspect, the L-dopa plasma level is at least about 4,000 ng/mL. In another aspect, the L-dopa plasma level is at least about 5,000 ng/mL. In another aspect, the L-dopa plasma level is at least about 6,000 ng/mL. In another aspect, the L-dopa plasma level is at least about 7,000 ng/mL. In another aspect, the L-dopa plasma level is at least about 8,000 ng/mL. In another aspect, the L-dopa plasma level is at least about 9,000 ng/mL. In particular, the first compound may be carbidopa phosphate prodrug, more particularly carbidopa 3'-monophosphate prodrug, carbidopa 4'-monophosphate prodrug and/or carbidopa 3',4'-diphosphate prodrug. In particular, the second compound may be L-dopa phosphate prodrug, more particularly L-dopa 3'-monophosphate prodrug, L-dopa 4'-monophosphate prodrug and/or L-dopa 3',4'-diphosphate prodrug.

In some embodiments, an amount of the first compound and an amount of the second compound are administered such that in combination they are sufficient to achieve an L-dopa plasma level from about 10 ng/mL to about 9,000 ng/mL. In one aspect, the L-dopa plasma level is from about 10 ng/mL to about 8,000 ng/mL In another aspect, the L-dopa plasma level is from about 25 ng/mL to about 6,000 ng/mL. In another aspect, the L-dopa plasma level is from about 50 ng/mL to about 4,000 ng/mL. In another aspect, the L-dopa plasma level is from about 100 ng/mL to about 2,000 ng/mL. In another aspect, the L-dopa plasma level is from about 25 ng/mL to about 1,200 ng/mL. In another aspect, the L-dopa plasma level is from about 10 ng/mL to about 500 ng/mL. In another aspect, the L-dopa plasma level is from about 25 ng/mL to about 500 ng/mL. In particular, the first compound may be carbidopa phosphate prodrug, more particularly carbidopa 3'-monophosphate prodrug, carbidopa 4'-monophosphate prodrug and/or carbidopa 3',4'-diphosphate prodrug. In particular, the second compound may be L-dopa phosphate prodrug, more particularly L-dopa 3'-monophosphate prodrug, L-dopa 4'-monophosphate prodrug and/or L-dopa 3',4'-diphosphate prodrug.

In some embodiments, the above-described L-dopa concentration ranges can be maintained for at least about a 1 hour interval, a 2 hour interval, a 3 hour interval, a 4 hour interval, a 5 hour interval, a 6 hour interval, a 7 hour interval, an 8 hour interval, a 9 hour interval, a 10 hour interval, an 11 hour interval, a 12 hour interval, a 13 hour interval, a 14 hour interval, a 15 hour interval, a 16 hour interval, a 17 hour interval, an 18 hour interval, a 19 hour interval, a 20 hour interval, a 21 hour interval, a 22 hour interval, a 23 hour interval, or a 24 hour interval.

G. Blood Plasma Levels of L-Dopa Phosphate Prodrug and Carbidopa Phosphate Prodrug.

It has been discovered that in some embodiments, following administration of the first compound and the second compound, an unexpected concentration of the second compound, i.e., an L-dopa phosphate prodrug, remains in the blood plasma and does not convert to L-dopa. Additionally, there may be an unexpected concentration of the first compound, i.e., a carbidopa phosphate prodrug, which remains in the blood plasma and does not convert to carbidopa. Surprisingly, the L-dopa phosphate prodrug and/or the carbidopa phosphate prodrug may remain in blood plasma during full duration of continuous infusion of the first compound and/or second compound.

Therefore in some embodiments, administration of the first and second compound results in an L-dopa phosphate prodrug plasma level from about 0 ng/mL to about 3600 ng/mL, about 1 ng/mL to about 3600 ng/mL, or about 10 ng/mL to about 3600 ng/mL. In one aspect, the L-dopa phosphate prodrug plasma level is from about 10 ng/mL to about 3200 ng/mL. In another aspect, the L-dopa phosphate prodrug plasma level is from about 25 ng/mL to about 2800 ng/mL. In another aspect, the L-dopa phosphate prodrug plasma level is from about 50 ng/mL to about 2400 ng/mL. In another aspect, the L-dopa phosphate prodrug plasma level is from about 10 ng/mL to about 2000 ng/mL. In another aspect, the L-dopa phosphate prodrug plasma level is from about 25 ng/mL to about 1600 ng/mL. In another aspect, the L-dopa phosphate prodrug plasma level is from about 25 ng/mL to about 1200 ng/mL. In another aspect, the L-dopa phosphate prodrug plasma level is from about 10 ng/mL to about 800 ng/mL. In another aspect, the L-dopa phosphate prodrug plasma level is from about 10 ng/mL to about 400 ng/mL. In another aspect, the L-dopa phosphate prodrug plasma level is from about 10 ng/mL to about 200 ng/mL. In another aspect, the L-dopa phosphate prodrug plasma level is from about 10 ng/mL to about 100 ng/mL.

In some embodiments, administration of the first and second compound results in an carbidopa phosphate prodrug plasma level from about 0 ng/mL to about 600 ng/mL, about 1 ng/mL to about 600 ng/mL or about 10 ng/mL to 600 ng/mL. In one aspect, the carbidopa phosphate prodrug plasma level is from about 10 ng/mL to about 500 ng/mL. In another aspect, the carbidopa phosphate prodrug plasma level is from about 10 ng/mL to about 400 ng/mL. In another aspect, the carbidopa phosphate prodrug plasma level is from about 10 ng/mL to about 300 ng/mL. In another aspect, the carbidopa phosphate prodrug plasma level is from about 10 ng/mL to about 200 ng/mL. In another aspect, the carbidopa phosphate prodrug plasma level is from about 10 ng/mL to about 100 ng/mL. In another aspect, the carbidopa phosphate prodrug plasma level is from about 25 ng/mL to about 600 ng/mL. In another aspect, the carbidopa phosphate prodrug plasma level is from about 25 ng/mL to about 500 ng/mL. In another aspect, the carbidopa phosphate prodrug plasma level is from about 25 ng/mL to about 400 ng/mL. In another aspect, the carbidopa phosphate prodrug plasma level is from about 25 ng/mL to about 300 ng/mL. In another aspect, the carbidopa phosphate prodrug plasma level is from about 25 ng/mL to about 200 ng/mL. In another aspect, the carbidopa phosphate prodrug plasma level is from about 25 ng/mL to about 100 ng/mL.

L-dopa phosphate prodrug concentration ranges and/or carbidopa phosphate prodrug plasma concentration ranges can be maintained for at least about a 1 hour interval, a 2 hour interval, a 3 hour interval, a 4 hour interval, a 5 hour interval, a 6 hour interval, a 7 hour interval, an 8 hour interval, a 9 hour interval, a 10 hour interval, an 11 hour interval, a 12 hour interval, a 13 hour interval, a 14 hour interval, a 15 hour interval, a 16 hour interval, a 17 hour interval, an 18 hour interval, a 19 hour interval, a 20 hour interval, a 21 hour interval, a 22 hour interval, a 23 hour interval, or a 24 hour interval. Further, the L-dopa phosphate prodrug concentration ranges and/or carbidopa phosphate prodrug concentration ranges may be maintained at the aforementioned intervals day-after-day, e.g., 2 days, 3 days, 4 days, 5 days, 6 days, 7 days, etc. Without being bound by theory, this may aid continuous administration of the first and second compound (either together or separately).

In some embodiments, an amount of the first compound and an amount of the second compound are administered such that they are sufficient to maintain a carbidopa plasma level less than about 2500 ng/mL. In one aspect, the carbidopa plasma level is less than about 2000 ng/mL. In another aspect, the carbidopa plasma level is less than about 1500 ng/mL. In another aspect, the carbidopa plasma level is less than about 1000 ng/mL. In another aspect, the carbidopa plasma level is less than about 500 ng/mL. In another aspect, the carbidopa plasma level is less than about 250 ng/mL. In another aspect, the carbidopa plasma level is less than about 100 ng/mL. In another aspect, the carbidopa plasma level is less than about 50 ng/mL. In another aspect, the carbidopa plasma level is less than about 25 ng/mL.

In some embodiments, the above-described carbidopa plasma concentration ranges are maintained for at least about: a 1 hour interval, a 2 hour interval, a 3 hour interval, a 4 hour interval, a 5 hour interval, a 6 hour interval, a 7 hour interval, an 8 hour interval, a 9 hour interval, a 10 hour interval, an 11 hour interval, a 12 hour interval, a 13 hour interval, a 14 hour interval, a 15 hour interval, a 16 hour interval, a 17 hour interval, an 18 hour interval, a 19 hour interval, a 20 hour interval, a 21 hour interval, a 22 hour interval, a 23 hour interval, or a 24 hour interval.

H. Phosphorous Load

In some embodiments, an amount of the first compound and an amount of the second compound can be administered to a subject and achieve a phosphorus intake of less than about 2000 mg/day, or less than about 2500 mg/day or less than about 3000 mg/day. The value 3000 mg/day is the accepted tolerable upper intake level. See DRI Dietary Reference Intakes for Calcium, Phosphorus, Vitamin D and Fluoride at www.nap.edu/ctalog/5776. In further embodiments, administration of therapeutic concentrations of the first and the second compound to a subject results in a total phosphorus load of about 350 mg/day to about 550 mg/day, or about 400 mg/day to about 500 mg/day, or about 400 mg/day to about 450 mg/day, or approximately 427 mg/day. The average dietary phosphorus intake in the U.S. population is approximately 1500 mg/day. See Ervin R. B., et al. 2004. Dietary intake of selected minerals for the United States population: 1999-2000. *Adv Data*. April 27; (341):1-5. Thus, the total phosphorus exposure from administration of the first and the second compound can be about 1850 mg/day to about 2000 mg/day, or about 1900 mg/day to about 1950 mg/day or about 1927 mg/day, which is significantly less than the accepted tolerable upper intake level of 3000 mg/day.

VI. CO-ADMINISTRATION AND/OR ADD-ON THERAPY

The methods of treatment of the present disclosure optionally can further comprise administration of one or more therapeutic agents for the treatment of Parkinson's disease (e.g. an anti-Parkinson's agent) in addition to the L-dopa prodrug and the carbidopa prodrug. In one embodiment, the additional therapeutic agent(s) is selected from the group consisting of decarboxylase inhibitors other than carbidopa (e.g., benserazide), catechol-0-methyl transferase ("COMT") inhibitors (e.g., entacapone and tolcapone), and monoamine oxidase A ("MAO-A") or monoamine oxidase B ("MAO-B") inhibitors (e.g., moclobemide, rasagiline, selegiline, and safinamide). In one aspect, the additional therapeutic agent(s) is selected from the group consisting of decarboxylase inhibitors other than carbidopa. In another aspect, the additional therapeutic agent(s) is selected from the group consisting of COMT inhibitors, such as entacapone. In another aspect, the additional therapeutic agent(s) is selected from the group consisting of MAO-A inhibitors. In another aspect, the additional therapeutic agent(s) is selected from the group consisting of MAO-B inhibitors.

The additional therapeutic agents and the first and second compound can be administered together or separately; and substantially simultaneously or subsequent to each other. Additionally, the additional therapeutic agents and the first and second compound can be in separate dosage forms which can be the same or different. For example, entacapone can be used adjunctively and can be orally delivered, and the first and the second compound discussed herein can be subcutaneously administered (separately or together in the same pharmaceutical composition). Further, the therapeutic agents and the first and the second compound can optionally be co-packaged, for example in a single container or in a plurality of containers within a single outer package, or co-presented in separate packaging ("common presentation").

In a similar manner, the pharmaceutical compositions of the present disclosure optionally can further comprise one or more additional therapeutic agents for the treatment of Parkinson's disease as described above.

VII. KITS

The present disclosure also relates to kits comprising one or more pharmaceutical dosage forms comprising a carbidopa phosphate prodrug; kits comprising one or more pharmaceutical dosage forms comprising a an L-dopa phosphate prodrug; and kits comprising one or more pharmaceutical dosage forms comprising both a carbidopa phosphate prodrug and an L-dopa phosphate prodrug. The kit optionally can comprise one or more additional therapeutic agents and/or instructions, for example, instructions for using the kit to treat a patient having Parkinson's disease and an associated condition.

In one embodiment, the kit comprises a first pharmaceutical dosage form, wherein the first pharmaceutical dosage form comprises a first compound corresponding in structure to Formula (I), or a pharmaceutically acceptable salt thereof. In one aspect, the kit comprises a second pharmaceutical dosage form comprising a second compound corresponding in structure to Formula (II), or a pharmaceutically acceptable salt thereof. In another aspect, the first pharmaceutical dosage form further comprises a second compound corresponding in structure to Formula (II), or a pharmaceutically acceptable salt thereof. In another aspect, the first pharmaceutical dosage form and, where applicable, the second pharmaceutical dosage form are liquid pharmaceutical dosage forms.

As dopamine is an achiral compound, the various embodiments discussed above potentially could be adapted for use with a D-dopa phosphate prodrug or a racemate of D-dopa phosphate prodrug and L-dopa phosphate prodrug in place of the L-dopa phosphate prodrug.

VIII. L-DOPA AND CARBIDOPA PRODRUG POLYMORPHS

Particular crystalline forms of the L-dopa prodrugs and carbidopa prodrugs described above also have been identified and are described herein. More particularly, such crystalline forms are L-dopa 4'-monophosphate anhydrate (i), L-dopa 4'-monophosphate anhydrate (ii), L-dopa 3'-monophosphate, L-dopa 3',4'-diphosphate trihydrate, carbidopa 4'-monophosphate trihydrate, carbidopa 4'-monophosphate dihydrate, carbidopa 4'-monophosphate dehydrate, carbidopa 3'-monophosphate (i), carbidopa 3'-monophosphate (ii), and carbidopa 3',4'-diphosphate sodium salt.

A. L-Dopa Prodrug Polymorphs

Figure 13:
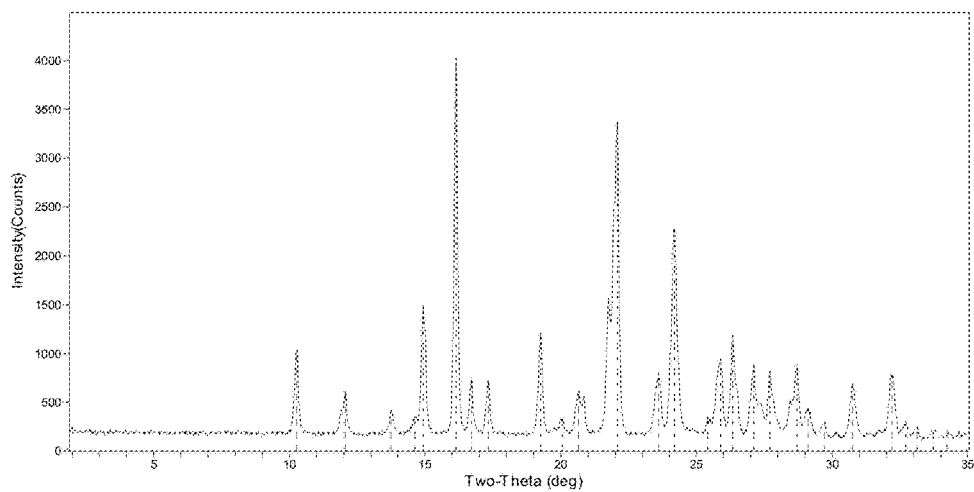
FIG. 13 is a powder X-ray diffraction pattern of L-dopa 4'-monophosphate anhydrate (i).

L-dopa 4'-monophosphate anhydrate (i) crystalline solid can be identified by characteristic peaks in its powder X-ray diffraction pattern (FIG. 13). One with skill in the art of analytical chemistry would be able to readily identify L-dopa 4'-monophosphate anhydrate (i) solid by as few as one characteristic peak in its powder X-ray diffraction pattern. Therefore, in one or more embodiments, a crystalline L-dopa 4'-monophosphate anhydrate (i) is provided demonstrating at least 1, at least 2, at least 3, at least 4, at least 5, at least 6, at least 7, at least 8, at least 9, at least 10, at least 11, at least 12, at least 13, at least 14 or 15 characteristic peaks in a powder X-ray diffraction pattern at values of two theta of 10.261±0.20, 12.053±0.20, 13.759±0.20, 14.932±0.20, 16.147±0.20, 16.718±0.20, 17.34±0.20, 19.254±0.20, 20.654±0.20, 22.078±0.20, 23.599±0.20, 24.198±0.20, 25.898±0.20, 26.338±0.20, and 27.117±0.20. Crystallographic unit cell parameters of L-dopa 4'-monophosphate anhydrate (i) also were obtained and were determined as: a is 7.0508 Å, b is 10.6253 Å, c is 14.7588 Å, to afford a cell volume of 1105.68 Å$^3$, wherein a, b, and c are each a representative length of the crystal lattice.

Figure 14:
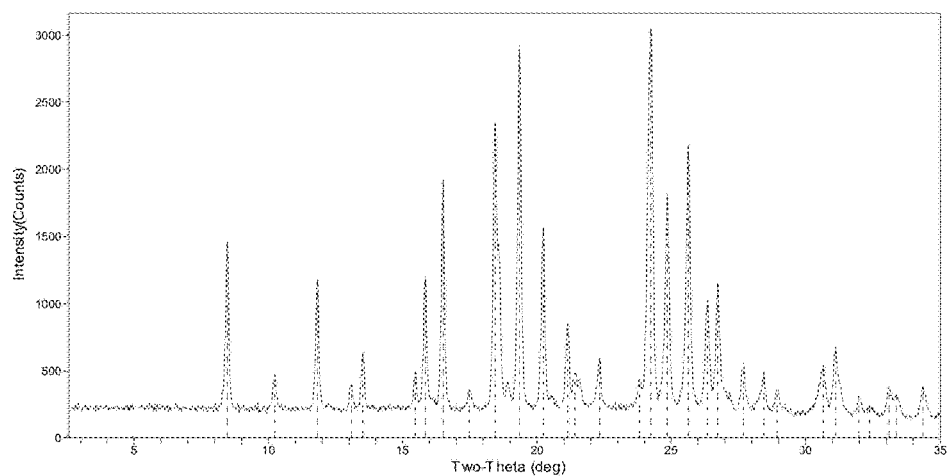
FIG. 14 is a powder X-ray diffraction pattern of L-dopa 4'-monophosphate anhydrate (ii).

L-dopa 4'-monophosphate anhydrate (ii) crystalline solid can be identified by characteristic peaks in its powder X-ray diffraction pattern (FIG. 14). One with skill in the art of analytical chemistry would be able to readily identify L-dopa 4'-monophosphate anhydrate (ii) solid by as few as one characteristic peak in its powder X-ray diffraction pattern. Therefore, in one or more embodiments, a crystalline L-dopa 4'-monophosphate anhydrate (ii) is provided demonstrating at least 1, at least 2, at least 3, at least 4, at least 5, at least 6, at least 7, at least 8, at least 9, at least 10, at least 11, at least 12, at least 13, at least 14 or 15 characteristic peaks in a powder X-ray diffraction pattern at values of two theta of 8.468±0.20, 10.234±0.20, 11.821±0.20, 13.084±0.20, 13.503±0.20, 15.48±0.20, 15.848±0.20, 16.513±0.20, 18.447±0.20, 19.346±0.20, 20.239±0.20, 21.139±0.20, 24.221±0.20, 24.865±0.20, 25.647±0.20.

Figure 15:
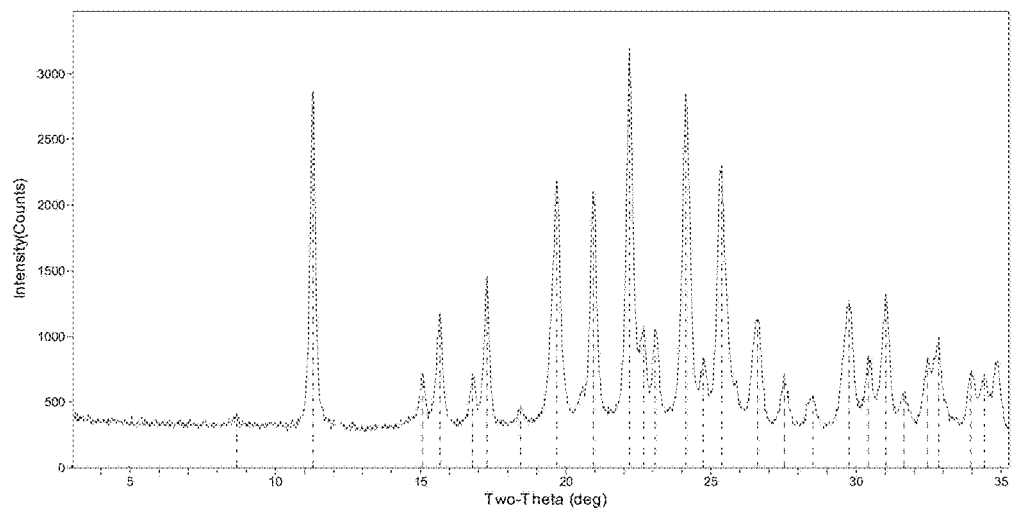
FIG. 15 is a powder X-ray diffraction pattern of L-dopa 3'-monophosphate.

L-dopa 3'-monophosphate crystalline solid can be identified by characteristic peaks in its powder X-ray diffraction pattern (FIG. 15). One with skill in the art of analytical chemistry would be able to readily identify L-dopa 3'-monophosphate solid by as few as one characteristic peak in its powder X-ray diffraction pattern. Therefore, in one or more embodiments, a crystalline L-dopa 3'-monophosphate is provided demonstrating at least 1, at least 2, at least 3, at least 4, at least 5, at least 6, at least 7, at least 8, at least 9, at least 10, at least 11, at least 12, at least 13, at least 14 or 15 characteristic peaks in a powder X-ray diffraction pattern at values of two theta of 8.662±0.20, 11.286±0.20, 15.079±0.20, 15.678±0.20, 16.786±0.20, 17.288±0.20, 18.438±0.20, 19.682±0.20, 20.946±0.20, 22.188±0.20, 22.671±0.20, 23.088±0.20, 24.144±0.20, 24.744±0.20, and 25.383±0.20.

Figure 16:
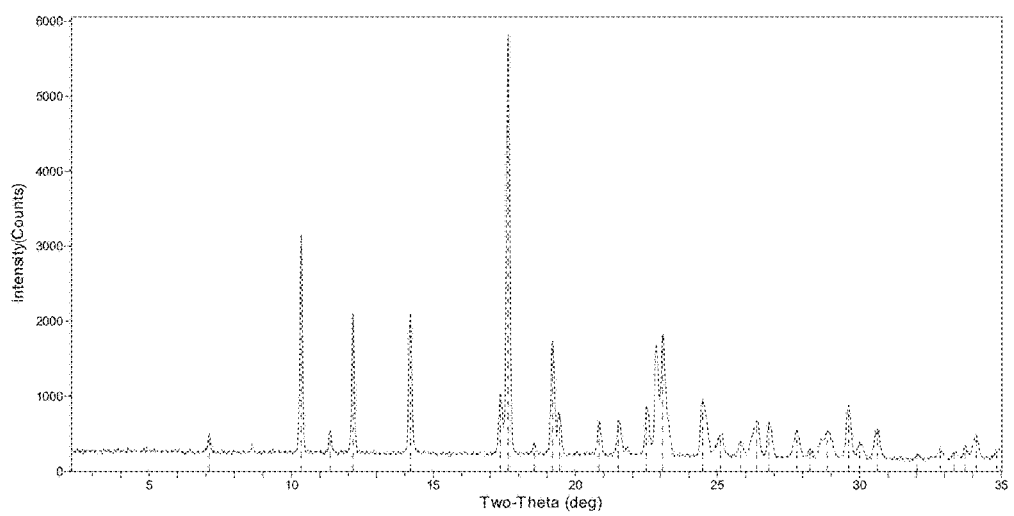
FIG. 16 is a powder X-ray diffraction pattern of L-dopa 3',4'-diphosphate trihydrate.

L-dopa 3',4'-diphosphate trihydrate crystalline solid can be identified by characteristic peaks in its powder X-ray diffraction pattern (FIG. 16). One with skill in the art of analytical chemistry would be able to readily identify L-dopa 3',4'-diphosphate trihydrate solid by as few as one characteristic peak in its powder X-ray diffraction pattern. Therefore, in one or more embodiments, a crystalline L-dopa 3',4'-diphosphate trihydrate is provided demonstrating at least 1, at least 2, at least 3, at least 4, at least 5, at least 6, at least 7, at least 8, at least 9, at least 10, at least 11, at least 12, at least 13, at least 14 or 15 characteristic peaks in a powder X-ray diffraction pattern at values of two theta of 7.118±0.20, 10.342±0.20, 11.355±0.20, 12.161±0.20, 14.201±0.20, 17.36±0.20, 17.632±0.20, 19.196±0.20, 19.444±0.20, 20.83±0.20, 21.504±0.20, 22.491±0.20, 23.085±0.20, 24.487±0.20, and 25.11±0.20.

B. Carbidopa Prodrug Polymorphs

Figure 17:
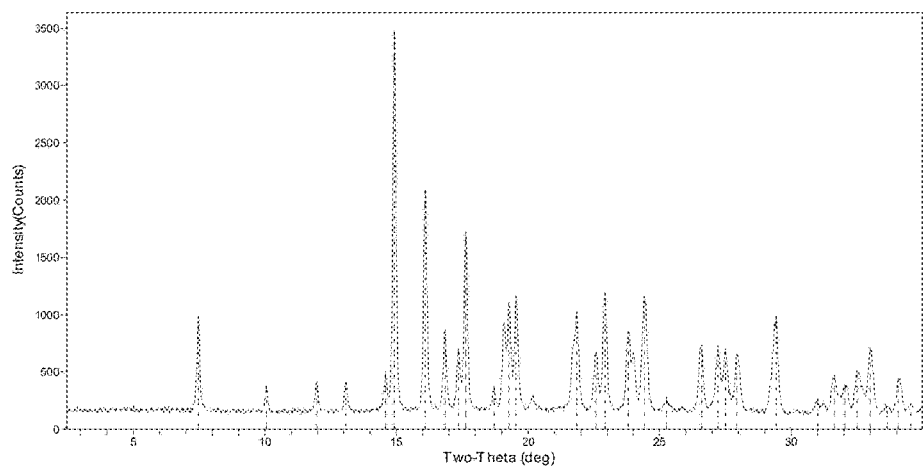
FIG. 17 is a powder X-ray diffraction pattern of carbidopa 4'-monophosphate trihydrate.

Carbidopa 4'-monophosphate trihydrate crystalline solid can be identified by characteristic peaks in its powder X-ray diffraction pattern (FIG. 17). One with skill in the art of analytical chemistry would be able to readily identify carbidopa 4'-monophosphate trihydrate solid by as few as one characteristic peak in its powder X-ray diffraction pattern. Therefore, in one or more embodiments, a crystalline carbidopa 4'-monophosphate trihydrate is provided demonstrating at least 1, at least 2, at least 3, at least 4, at least 5, at least 6, at least 7, at least 8, at least 9, at least 10, at least 11, at least 12, at least 13, at least 14 or 15 characteristic peaks in a powder X-ray diffraction pattern at values of two theta of 7.484±0.20, 10.05±0.20, 11.971±0.20, 13.085±0.20, 14.923±0.20, 16.095±0.20, 16.85±0.20, 17.359±0.20, 17.635±0.20, 19.269±0.20, 19.544±0.20, 21.842±0.20, 22.578±0.20, 22.921±0.20, and 23.822±0.20. Crystallographic unit cell parameters of carbidopa 4'-monophosphate trihydrate also were obtained and were determined as: a is 7.0226 Å, b is 9.4565 Å, c is 23.615 Å, to afford a cell volume of 1568.25 Å$^3$, wherein a, b, and c are each a representative length of the crystal lattice.

Figure 18:
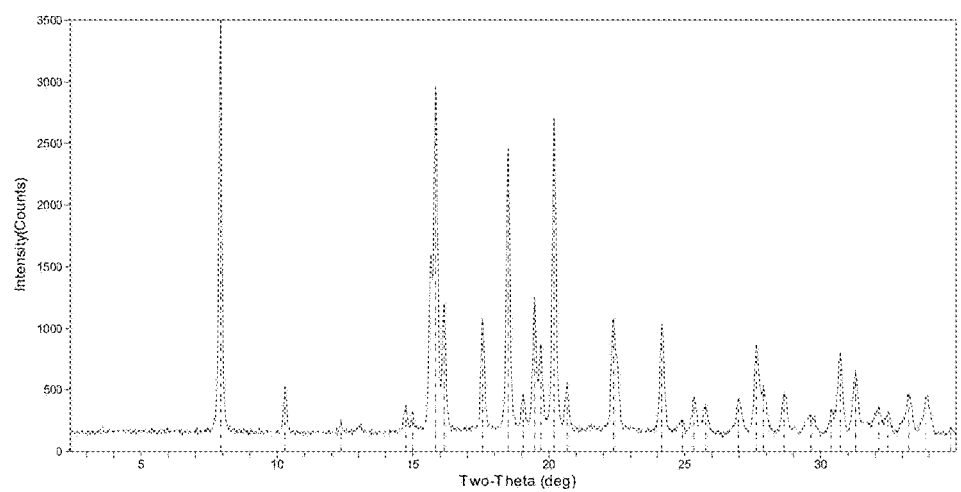
FIG. 18 is a powder X-ray diffraction pattern of carbidopa 4'-monophosphate dihydrate.

Carbidopa 4'-monophosphate dihydrate crystalline solid can be identified by characteristic peaks in its powder X-ray diffraction pattern (FIG. 18). One with skill in the art of analytical chemistry would be able to readily identify carbidopa 4'-monophosphate dihydrate solid by as few as one characteristic peak in its powder X-ray diffraction pattern. Therefore, in one or more embodiments, a crystalline carbidopa 4'-monophosphate dihydrate is provided demonstrating at least 1, at least 2, at least 3, at least 4, at least 5, at least 6, at least 7, at least 8, at least 9, at least 10, at least 11, at least 12, at least 13, at least 14 or 15 characteristic peaks in a powder X-ray diffraction pattern at values of two theta of 7.925±0.20, 10.28±0.20, 12.344±0.20, 15.002±0.20, 15.841±0.20, 16.158±0.20, 17.565±0.20, 18.506±0.20, 19.058±0.20, 19.473±0.20, 19.702±0.20, 20.188±0.20, 20.668±0.20, 22.37±0.20, and 24.167±0.20.

Figure 19:
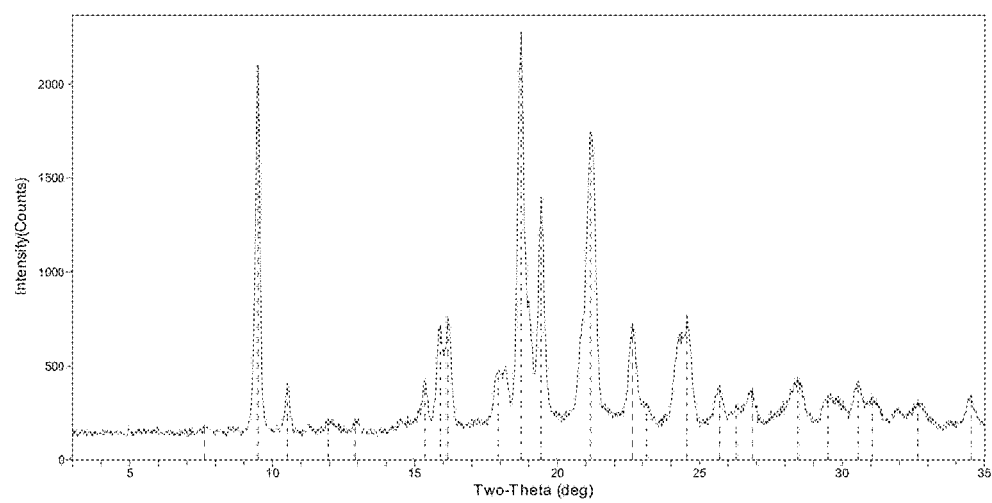
FIG. 19 is a powder X-ray diffraction pattern of carbidopa 4'-monophosphate dehydrate.

Carbidopa 4'-monophosphate dehydrate crystalline solid can be identified by characteristic peaks in its powder X-ray diffraction pattern (FIG. 19). One with skill in the art of analytical chemistry would be able to readily identify carbidopa 4'-monophosphate dehydrate solid by as few as one characteristic peak in its powder X-ray diffraction pattern. Therefore, in one or more embodiments, a crystalline carbidopa 4'-monophosphate dehydrate is provided demonstrating at least 1, at least 2, at least 3, at least 4, at least 5, at least 6, at least 7, at least 8, at least 9, or at least 10 characteristic peaks in a powder X-ray diffraction pattern at values of two theta of 9.492±0.20, 10.528±0.20, 15.356±0.20, 15.907±0.20, 16.165±0.20, 17.933±0.20, 18.737±0.20, 19.429±0.20, 21.176±0.20, and 22.626±0.20.

Figure 20:
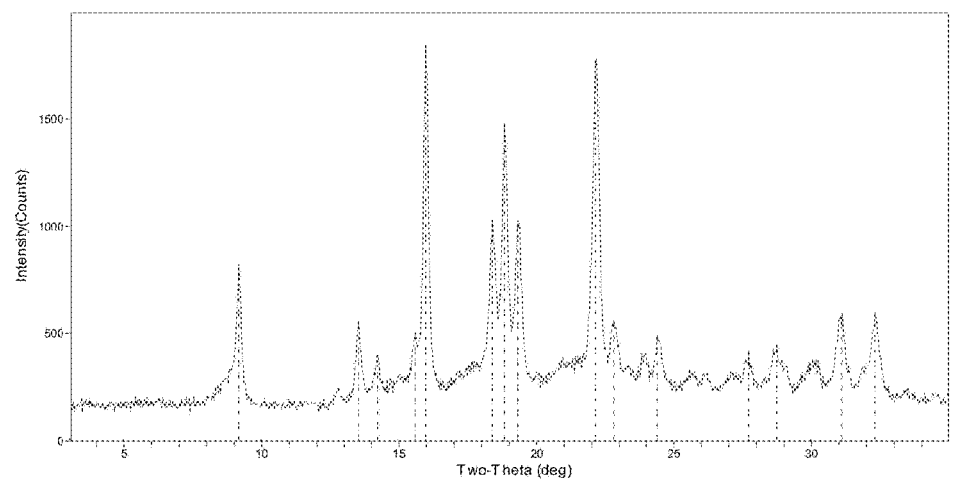
FIG. 20 is a powder X-ray diffraction pattern of carbidopa 3'-monophosphate (i).

Carbidopa 3'-monophosphate (i) crystalline solid can be identified by characteristic peaks in its powder X-ray diffraction pattern (FIG. 20). One with skill in the art of analytical chemistry would be able to readily identify carbidopa 3'-monophosphate (i) solid by as few as one characteristic peak in its powder X-ray diffraction pattern. Therefore, in one or more embodiments, a crystalline carbidopa 3'-monophosphate (i) is provided demonstrating at least 1, at least 2, at least 3, at least 4, at least 5, at least 6, at least 7, at least 8, at least 9, or at least 10 characteristic peaks in a powder X-ray diffraction pattern at values of two theta of 9.171±0.20, 13.539±0.20, 14.23±0.20, 15.589±0.20, 15.979±0.20, 18.394±0.20, 18.832±0.20, 19.315±0.20, 22.143±0.20, and 22.81±0.20.

Figure 21:
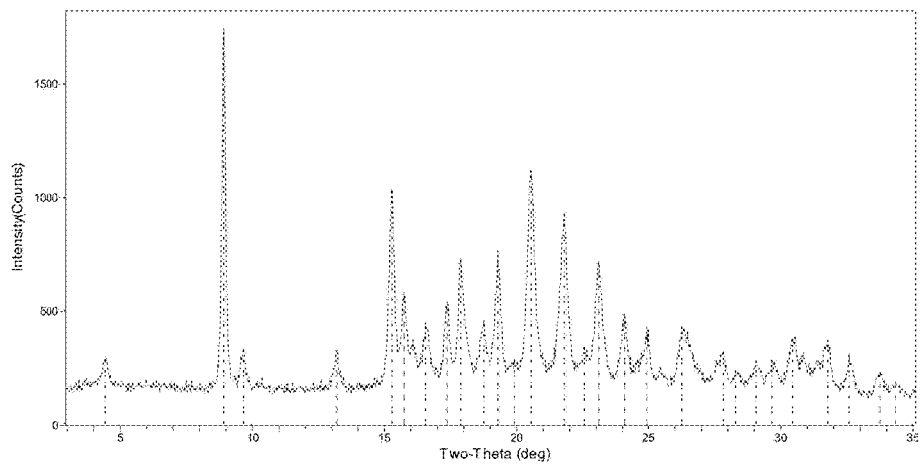
FIG. 21 is a powder X-ray diffraction pattern of carbidopa 3'-monophosphate (ii).

Carbidopa 3'-monophosphate (ii) crystalline solid can be identified by characteristic peaks in its powder X-ray diffraction pattern (FIG. 21). One with skill in the art of analytical chemistry would be able to readily identify carbidopa 3'-monophosphate (ii) solid by as few as one characteristic peak in its powder X-ray diffraction pattern. Therefore, in one or more embodiments, a crystalline carbidopa 3'-monophosphate (ii) is provided demonstrating at least 1, at least 2, at least 3, at least 4, at least 5, at least 6, at least 7, at least 8, at least 9, or at least 10 characteristic peaks in a powder X-ray diffraction pattern at values of two theta of 4.433±0.20, 8.917±0.20, 9.654±0.20, 13.192±0.20, 15.288±0.20, 15.747±0.20, 17.886±0.20, 19.291±0.20, 20.554±0.20, and 21.797.

Figure 22:
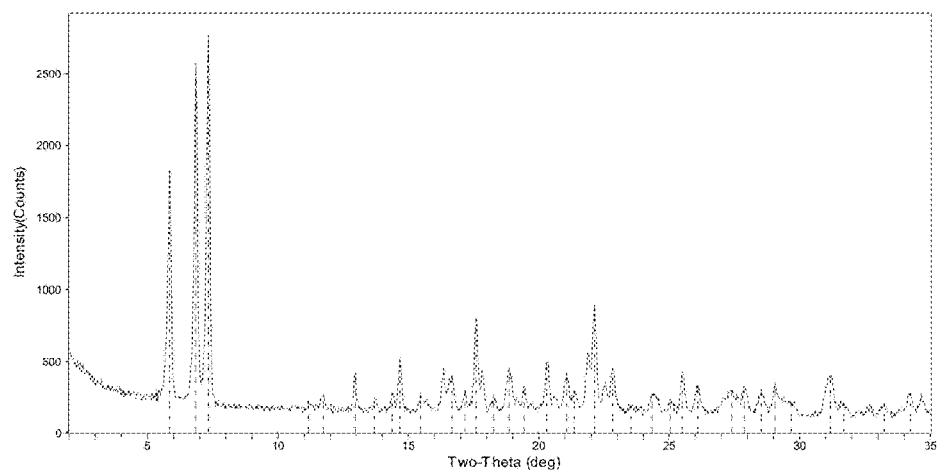
FIG. 22 is a powder X-ray diffraction pattern of carbidopa 3',4'-diphosphate sodium salt.

Carbidopa 3',4'-diphosphate sodium salt crystalline solid can be identified by characteristic peaks in its powder X-ray diffraction pattern (FIG. 22). One with skill in the art of analytical chemistry would be able to readily identify carbidopa 3',4'-diphosphate sodium salt solid by as few as one characteristic peak in its powder X-ray diffraction pattern. Therefore, in one or more embodiments, a crystalline carbidopa 3',4'-diphosphate sodium salt is provided demonstrating at least 1, at least 2, at least 3, at least 4, at least 5, at least 6, at least 7, at least 8, at least 9, at least 10, at least 11, at least 12, at least 13, at least 14 or 15 characteristic peaks in a powder X-ray diffraction pattern at values of two theta of 5.852±0.20, 6.861±0.20, 7.338±0.20, 11.159±0.20, 11.729±0.20, 12.953±0.20, 13.714±0.20, 14.381±0.20, 14.686±0.20, 15.479±0.20, 16.676±0.20, 17.179±0.20, 17.592±0.20, 18.861±0.20 and 20.305±0.20.

Compositions and combinations comprising the above-described L-dopa and carbidopa polymorphs are also contemplated. Therefore, in one or more embodiments, pharmaceutical compositions and combinations comprising the above-described L-dopa and carbidopa polymorphs are provided as well as methods of treating Parkinson's disease by administering such pharmaceutical compositions and combinations. In particular methods of treating Parkinson's disease by administering a pharmaceutical composition comprising one or more of the L-dopa and carbidopa polymorphs identified by characteristic peaks in the powder X-ray diffraction patterns of any one of FIGS. 13-22 is provided.

Powder X-ray diffraction (PXRD) analysis of samples was conducted in the following manner. Samples for X-ray diffraction analysis were prepared by spreading the sample in a thin layer on the sample holder and gently flattening the sample with a microscope slide. For example, the sample may have been ground to a fine powder with mortar and pestle, or with glass microscope slides for limited quantity samples. Samples were run in one of three configurations: circular bulk holder, a quartz zero background plate, or hot stage mount (similar mounting to a zero background plate).

Diffraction patterns were collected using an Inel G3000 difrractometer equipped with an incident beam germanium monochromator to provide Cu-K$_{\alpha 1}$ radiation. The X-ray generator was operated at a voltage of 40 kV and a current of 30 mA. The Inel G3000 is equipped with a position sensitive detector that monitors all diffraction data simultaneously. The detector was calibrated by collecting the attenuated direct beam for seven seconds in 1 degree intervals across a 90 degree two theta range. The calibration was checked against a silicon line position reference standard (NIST 640c). Samples were placed on an aluminum sample holder and leveled with a glass slide.

Alternatively, X-ray powder diffraction can be performed using a Rigaku Miniflex difractometer (30 kV and 15 mA; X-ray source: Cu; Range: 2.00-40.00° Two Theta; Scan rate: 1-5 degree/minute) or a Scintag X1 or X2 difractometer (2 kW normal focus X-ray tube with either a liquid nitrogen or Peltier cooled germanium solid state detector; 45 kV and 40 mA; X-ray source: Cu; Range: 2.00-40.00° Two Theta; Scan Rate: 1-5 degree/minute).

Characteristic powder X-ray diffraction pattern peak positions are reported in terms of angular positions (two theta) with an allowable variability of ±0.20°. The variability of ±0.10° is intended to be used when comparing two powder X-ray diffraction patterns. In practice, if a diffraction pattern peak from one pattern is assigned a range of angular positions (two theta) which is the measured peak position ±0.20° and a diffraction pattern peak from another pattern is assigned a range of angular positions (two theta) which is measured peak position ±0.20° and if those ranges of peak position overlap, then the two peaks are considered to have the same angular position (two theta). For example, if a diffraction pattern peak from one pattern is determined to have a peak position of 5.20° for comparison purposes the allowable variability allows the peak to be assigned a position in the range of 5.00°-5.40°. If a comparison peak from the other diffraction pattern is determined to have a peak position of 5.35° and the allowable variability allows the peak to be assigned a position in the range of 5.15°-5.55°, then the two peaks being compared are considered to have the same angular position (two theta) because there is overlap between the two ranges of peak positions.

Single crystal X-ray diffraction analysis of samples was conducted in the following manner. Samples for X-ray diffraction analysis were prepared by affixing selected single crystals to glass pins with epoxy adhesive. X-ray diffraction data was collected using a Bruker SMART system with an APEX area detector (50 kv and 40 mA; X-ray source: Mo). Data were collected at −100° C.

IX. EXAMPLES

The following non-limiting examples are provided to further illustrate the present disclosure. Abbreviations used in the examples below include the following:

"DBU" means 1,8-diazabicyclo[5.4.0]-undec-7-ene.
"DCM" means dichloromethane.
"EDTA" means ethylenediaminetetraacetic acid.
"FCC" means flash column chromatography.
"HPLC" means high pressure liquid chromatography
"IPA" means isopropanol.
"LC-MS" means liquid chromatography-mass spectrometry.
"m-CPBA" means meta-chloroperoxybenzoic acid.
"MTBE" means methyl tertiary butyl ether.
"pa" means peak area.
"THF" means tetrahydrofuran.
"TLC" means thin layer chromatography.
"$t_{1/2}$" means biological half-life, i.e., the time required for half the quantity of a drug or other substance administered to a living organism to be metabolized or eliminated by normal biological processes.

Example 1: Synthesis of L-Dopa Monophosphates

L-dopa 3'-monophosphate and L-dopa 4'-monophosphate were prepared as shown in Scheme 1 below:

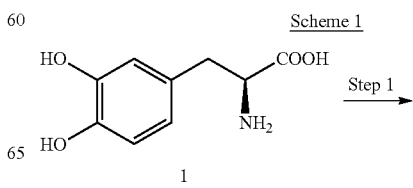

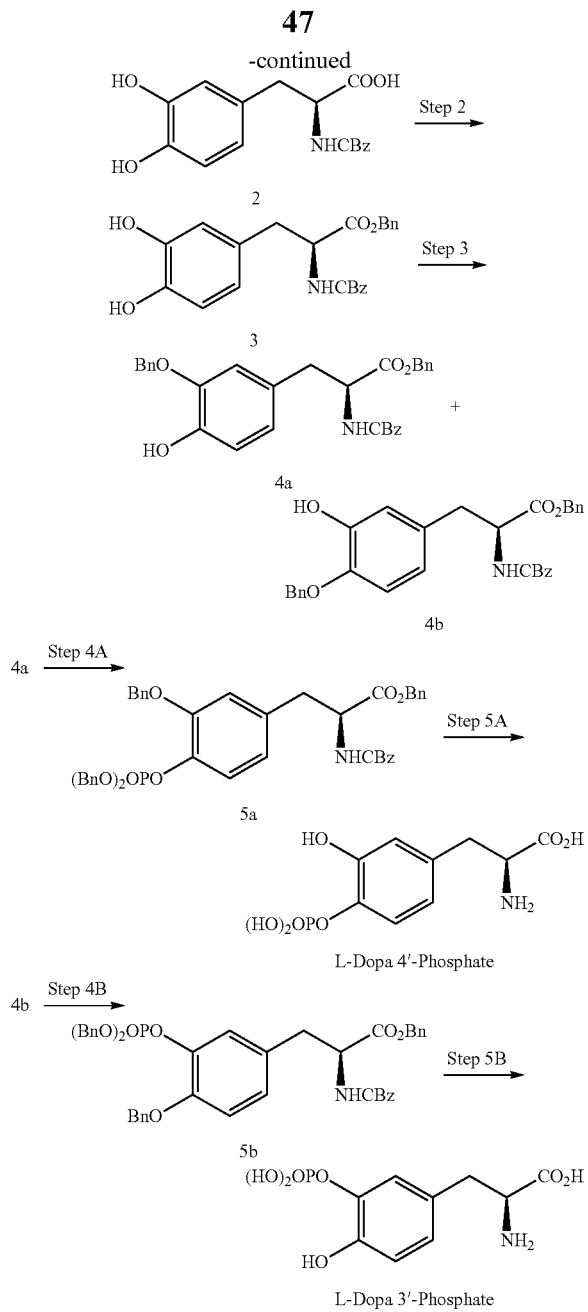

with MTBE (500 mL×2). The combined organic layer was washed with water (500 mL), saturated sodium chloride solution (500 mL), dried over sodium sulfate, and concentrated under vacuum at 45° C. to 50° C. to provide crude Compound 2 as a viscous liquid (120 g, 72%).

Step 2

Cesium carbonate (123 g, 0.37 mol) was added in two lots to a solution of Compound 2 (250 g, 0.75 mol) in dimethylformamide (2 L) at 0° C. Benzyl bromide (90.3 mL, 0.75 mol) was added drop-wise to this mixture over a period of 30 minutes at 0° C. and then the reaction mass was stirred at room temperature for 16 hours. Reaction completion was monitored by TLC. After the complete consumption of starting material, the reaction mass was diluted with water (5 L) and extracted with MTBE (1 L×2). The combined organic layer was washed with water (1 L), saturated sodium chloride solution (0.5 L), dried over sodium sulfate, and concentrated under vacuum at 45° C. to 50° C. to provide crude Compound 4 as a viscous liquid (250 g).

Step 3

Cesium carbonate (698.5 g, 2.14 mol) was added in four lots to a solution of Compound 3 (900 g, 2.14 mol) in dimethylformamide (7.2 L) at 0° C. Benzyl bromide (512 mL, 4.28 mol) was added drop-wise to this mixture over a period of one hour at 0° C. and then the reaction mass was stirred at room temperature for 16 hours. Reaction completion was monitored by TLC. After the complete consumption of starting material, the reaction mass was diluted with water (15 L) and extracted with MTBE (3 L×2). The combined organic layer was washed with water (3 L), saturated sodium chloride solution (1.5 L), dried over sodium sulfate, and concentrated under vacuum at 45° C. to 50° C. to provide a crude product as a viscous liquid (1 Kg).

The crude product obtained was blended with the crude product from previous batches (total of 1.6 Kg) and was repeatedly purified by flash column chromatography over silica gel (230-400 mesh) using 10-20% ethyl acetate in petroleum ether to provide Compounds 4a (270 g) and 4b (255 g).

Step 4A

Potassium tert-butoxide (65.6 g, 0.58 mol) was added in four lots to a solution of Compound 4a (200 g, 0.39 mol) in tetrahydrofuran (2.0 L) at 0° C. A 10% w/w solution dibenzylphosphoryl chloride in toluene (2.31 Kg, 0.78 mol) was added drop-wise to this mixture over a period of 30 minutes at 0° C. and then the reaction mass was stirred at room temperature for 2 hours. Reaction completion was monitored by thin layer chromatography. After the complete consumption of starting material, the reaction mass was cooled to 0° C. to 5° C. and quenched with water (1.0 L). The organic layer was separated and the aqueous layer was extracted with toluene (500 mL). The combined organic layer was washed with water (1 L), saturated NaCl solution (500 mL), dried over sodium sulfate, and concentrated under vacuum at 45° C. to 50° C. The crude product obtained was purified by column chromatography over silica gel (230-400 mesh) using 30%-40% ethyl acetate in petroleum ether to yield Compound 5a as a viscous liquid (185 g, 61.6%).

Step 4B

Potassium tert-butoxide (68.9 g, 0.61 mol) was added in four lots to a solution of Compound 4b (210 g, 0.41 mol) in tetrahydrofuran (2.2 L) at 0° C. A 10% w/w solution dibenzylphosphoryl chloride in toluene (2.43 Kg, 0.82 mol) was added drop-wise to this mixture over a period of 30 minutes at 0° C. After complete addition, the reaction mass was stirred at room temperature for 2 hours. Reaction completion was monitored by thin layer chromatography.

Specifically, L-dopa 3'-monophosphate and L-dopa 4'-monophosphate were prepared as described in Steps 1 through 5B below.

Step 1

A solution of sodium hydroxide (40 g, 1.0 mol) in water (300 mL) was added drop-wise to a suspension of Compound 1 (100 g, 0.5 mol) in water (300 mL) over a period of 20 minutes at 0° C. Benzylchloroformate (103.9 g, 0.6 mol) in dioxane (400 mL) was added drop-wise to the suspension over a period of 30 minutes at 0° C. and then the reaction mass was stirred at room temperature for 16 hours. Reaction completion was monitored by TLC. After the complete consumption of starting material, the reaction mass was basified to pH=10 using 10% sodium hydroxide (200 mL) and extracted with MTBE (500 mL). The organic layer was separated and discarded. The aqueous layer was acidified to pH=2 using 6 N HCl (150 mL) and extracted After reaction completion, the reaction mass was cooled to 0° C. to 5° C. and quenched with water (1.0 L). The organic layer was separated and the aqueous layer was extracted with toluene (500 mL). The combined organic layer was washed with water (1 L), saturated NaCl solution (500 mL), dried over sodium sulfate, and concentrated under vacuum at 45° C. to 50° C. The crude product obtained from this batch was blended with the crude product (45 g) from another batch and purified by column chromatography over silica gel (230-400 mesh) using 30%-40% ethyl acetate in petroleum ether to yield Compound 5b as a viscous liquid (250 g, 65%).

Step 5A

10% Pd/C (30 g, 50% wet) was added to a solution of Compound 5a (100 g, 0.13 mol) in ethanol and water (1 L, 4:1) under nitrogen atmosphere. The reaction flask was evacuated and purged with hydrogen gas three times and then hydrogenated at 4 Kg/cm$^2$ pressure (approximately 4 atmospheres) for 16 hours. After the reaction was complete, water (500 mL) was added to the reaction mixture and the catalyst was removed by filtration through K100 cellulose filter pad (520 mm diameter). The filtrate was concentrated under reduced pressure. The crude product obtained was stirred with ethanol (60 mL), filtered, and dried under suction to give (S-2-amino-3-(3-hydroxy-4-(phosphonooxy) phenyl)-propanoic acid; L-dopa (4-phosphate) (17 g, 47%) as an off-white solid. $^1$H NMR (300 MHz, D$_2$O) δ 7.1 (d, J=8.1 Hz, 1H), 6.7 (s, 1H), 6.68 (d, J=8.1 Hz, 1H), 4.1 (q, J=5.1 Hz, 1H), 3.15 (dd, J=14.7 Hz, 4.5 Hz, 1H), 3.0-2.93 (m, 1H); MS (LCMS) m/z 278 [M+H]+.

Step 5B

10% Pd/C (30 g, 50% wet) was added to a solution of Compound 5b (100 g, 0.13 mol) in ethanol and water (1 L, 4:1) under nitrogen atmosphere. The reaction flask was evacuated and purged with hydrogen gas three times and then hydrogenated at 4 Kg/cm$^2$ pressure (approximately 4 atmospheres) for 16 hours. After the reaction was complete, water (500 mL) was added to the reaction mixture and the catalyst was removed by filtration through K100 cellulose filter pad (520 mm diameter). The filtrate was concentrated under reduced pressure. The crude product obtained was stirred with ethanol (60 mL), filtered, and dried under suction to give (S-2-amino-3-(4-hydroxy-3-(phosphonooxy) phenyl)-propanoic acid; L-dopa (3-phosphate) (21 g, 58.5%) as an off-white solid. $^1$H NMR (300 MHz, D$_2$O) δ 7.06 (s, 1H), 6.85 (s, 2H), 4.08 (q, J=4.8 Hz, 1H), 3.16 (dd, J=14.7 Hz, 5.1 Hz, 1H), 3.0-2.92 (m, 1H); MS (LCMS) m/z 278 [M+H]+.

Example 2: Synthesis of L-Dopa Diphosphate

L-dopa 3',4'-diphosphate was prepared as shown in Scheme 2 below:

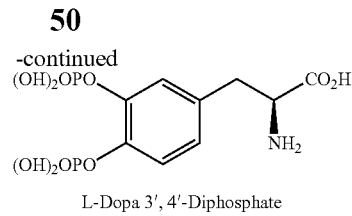

L-Dopa 3',4'-Diphosphate

Specifically, L-dopa 3',4'-diphosphate was prepared as described in Steps 6 and 7 below.

Step 6

Cesium carbonate (484 g, 1.48 mol) was added in two lots to a solution of Compound 3 (250 g, 0.59 mol) in dimethylformamide (2.5 L) at 0° C. A 10% w/w solution of dibenzylphosphoryl chloride in toluene (3.52 Kg, 1.18 mol) was added drop-wise to this mixture over a period of one hour at 0° C. and the reaction mass was stirred at room temperature for 2 hours. Reaction completion was monitored by TLC. After the complete consumption of the starting material, the reaction mass was cooled to 0° C. to 5° C. and quenched with water (5 L). The organic layer was separated and the aqueous layer was extracted with toluene (1 L). The combined organic layer was washed with water (1 L), saturated sodium chloride solution (0.5 L), dried over sodium sulfate, filtered, and concentrated under vacuum at 45° C. to 50° C. The crude product obtained was purified by column chromatography over silica gel (230-400 mesh) using 10%-15% ethyl acetate in petroleum ether to provide Compound 6 as a gummy liquid (240 g) of intermediate purity.

Step 7

10% Pd/C (20 g, 50% wet) was added to a solution of Compound 6 (50 g, 0.05 mol) in THF (500 mL) under nitrogen atmosphere. The reaction flask was evacuated and purged with hydrogen gas three times and then hydrogenated at 6 Kg/cm$^2$ pressure for 8 hours. After the reaction was complete, water (250 mL) was added to the reaction mixture and the catalyst was removed by filtration through K100 cellulose filter pad (520 mm diameter). The filtrate was concentrated under reduced pressure. The crude product obtained was stirred with ethanol (30 mL), filtered, and dried under suction to provide L-dopa (3,4-Phosphate) (12.8 g, 64%, purity corrected) as off-white solid. $^1$H NMR (300 MHz, D$_2$O) δ 7.21 (d, J=8.4 Hz, 1H), 7.16 (s, 1H), 6.95 (d, J=7.8 Hz, 1H), 4.23 (q, J=2.7 Hz, 1H), 3.24 (dd, J=15 Hz, 4.8 Hz, 1H), 3.08-3.01 (m, 1H); MS (LCMS) m/z 358 [M+H]+.

Example 3: Synthesis of Carbidopa Monophosphates

Carbidopa 3'-phosphate and carbidopa 4'-phosphate were prepared as shown in Scheme 3 below:

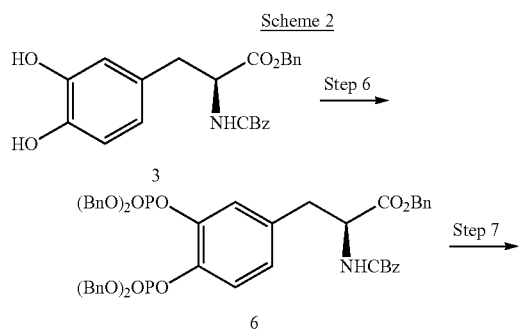

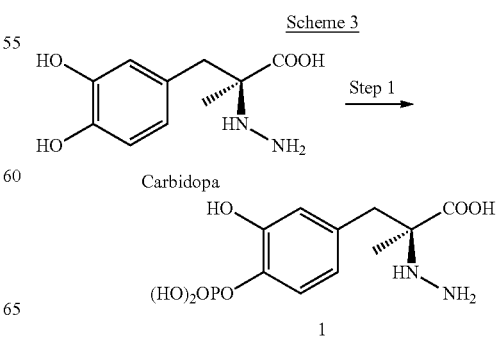

-continued

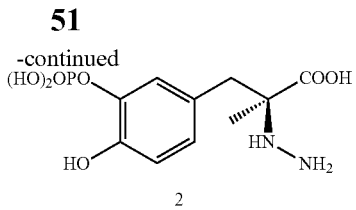

2

Specifically, carbidopa 3'-phosphate and carbidopa 4'-phosphate were prepared as described in Step 1 below.

Step 1

A thick mixture of phosphorus pentoxide (2.325 g, 16.38 mmol) and phosphoric acid (85% aq., 1.79 mL, 26.2 mmol) was heated to 100° C. for 15 minutes resulting in a clear solution. The solution was cooled back to 50° C. and carbidopa monohydrate (0.400 g, 1.64 mmol) was added. After 3 hours, the solution was cooled to room temperature, stirred for 14 hours, and then warmed to 35° C. After 24 hours, the solution was cooled to room temperature and stirred for 60 hours. Water (2 mL, exotherm to 50° C.) was added, the solution was stirred for 5 minutes, and then analyzed by HPLC (Agilent Poroshell 120 EC-C18 #693975-902 4.6×150 mm column, 1 mL/minute 0.1% aq. $H_3PO_4$/$CH_3CN$, 3 minute 97:3, 4 minute gradient to 70:30, 2 minute gradient to 0:100, hold 1 minute, detection at 220 nm) showing: carbidopa (6.7 minutes): 2.6 pa %, phosphate 1 (5.1 minutes): 38.2 pa %, phosphate 2 (5.7 minutes): 37.7 pa %, diphosphate (2.3 minutes): 5.9 pa %. The aqueous solution was diluted with water (5×), then purified by preparative HPLC (Kromasil Phenyl 3 cm ID×25 cm, 5 micron column, 30 mL/minute 0.1% formic acid/$CH_3CN$, 10 minute 97:3, 5 minute gradient to 93:7, 0.5 minute gradient to 100:0, detection at 277 nm). Pure fractions of separated monophosphates were combined, concentrated on a rotary evaporator (35° C. bath temperature) to 10 mL each, then lyophilized, giving carbidopa 4'-phosphate 1 (152 mg, 30% yield) and carbidopa 3'-phosphate 2 (137 mg, 27% yield) as white amorphous powders. Carbidopa 3'-monophosphate: $^1$H NMR (400 MHz, Deuterium Oxide) δ 7.20 (dd, J=8.2, 1.2 Hz, 1H), 6.84 (d, J=2.1 Hz, 1H), 6.77 (dd, J=8.3, 2.2 Hz, 1H), 3.19 (d, J=14.2 Hz, 1H), 2.99 (d, J=14.2 Hz, 1H), 1.52 (s, 3H); MS (ESI) m/z 307 [M+H]+. Carbidopa 4'-monophosphate: 1H NMR (400 MHz, Deuterium Oxide) δ 7.14 (t, J=1.4 Hz, 1H), 7.01-6.83 (m, 2H), 3.19 (d, J=14.3 Hz, 1H), 3.00 (d, J=14.4 Hz, 1H), 1.52 (s, 3H); MS (ESI) m/z 307 [M+H]+.

Example 4a: Synthesis of Carbidopa Diphosphate

Carbidopa 3',4'-diphosphate was prepared as shown in Scheme 4a below:

Scheme 4a

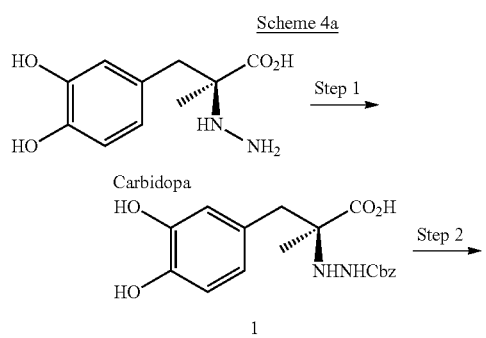

-continued

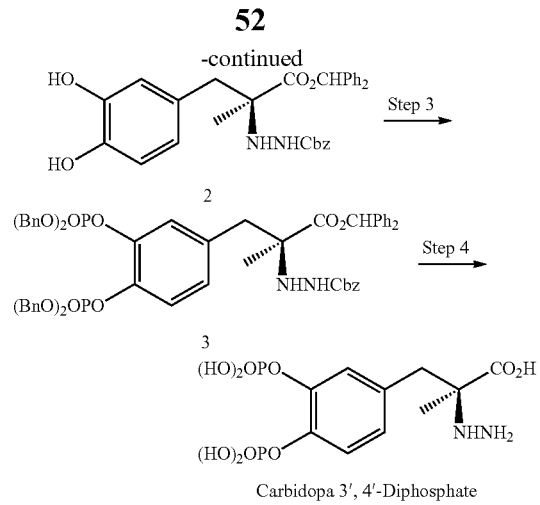

Carbidopa 3', 4'-Diphosphate

Specifically, carbidopa 3',4'-diphosphate was prepared as described in Steps 1 through 4 below.

Step 1

A slurry of carbidopa monohydrate (20.0 g, 82 mmol), sodium bicarbonate (7.57 g, 90 mmol), water (200 mL), and THF (100 mL) was cooled to 5° C. to 10° C. and N-(benzyloxycarbonyloxy)succinimide (20.4 g, 82 mmol) was added. The mixture was warmed to ambient temperature and became a nearly homogeneous solution over 5 hours, when LC-MS showed nearly complete reaction. The solution was diluted with MTBE (100 mL), the layers separated, and organic layer extracted with saturated aqueous $NaHCO_3$ (100 mL). The aqueous layers were acidified with 2 N HCl (160 mL) and the acidic aqueous layer was extracted with MTBE (2×100 mL). During the second back-extraction, a small amount of product began to precipitate. The combined organic layers were washed with brine (20 mL) and residual solid rinsed out of the separatory funnel with MTBE (20 mL). The resulting mixture was concentrated to 43 g total mass and 10% THF/MTBE (60 mL) was added. The mixture was too thick to stir, so additional MTBE (60 mL to 6 vol 5% THF/MTBE) was added. The resulting white slurry was then heated to 50° C. The slurry was cooled to ambient temperature over one hour and then stirred for 14 hours. The white solid was filtered, washed with 5% THF/MTBE (20 mL), and dried in a vacuum oven (50° C.), giving (S)-2-(2-((benzyloxy)carbonyl)-hydrazinyl)-3-(3,4-dihydroxyphenyl)-2-methylpropanoic acid compound with THF (4:3) (31.1 g, 71.9 mmol, 91% yield) as a white solid. $^1$H NMR (400 MHz, DMSO-$d_6$) δ 8.66 (d, J=9.0 Hz, 2H), 8.18 (br s, 1H), 7.49-7.17 (m, 5H), 6.59 (dd, J=5.0, 3.0 Hz, 2H), 6.44 (dd, J=8.0, 2.0 Hz, 1H), 5.04 (s, 2H), 2.73 (d, J=13.4 Hz, 1H), 2.59 (d, J=13.3 Hz, 1H), 1.07 (s, 3H); MS (ESI) m/z 361 [M+H]+.

Step 2

A solution of benzophenone hydrazone (20.0 g, 102 mmol) in DCM (100 mL) was cooled to <0° C. and iodine (0.052 g, 0.204 mmol) and 1,1,3,3-tetramethylguanidine (25.6 mL, 204 mmol) were added. m-CPBA (30.5 g, 132 mmol) was added portion-wise between −10° C. and 00° C. over 5 minutes (exothermic, dry ice/acetone bath to control). The mixture was stirred between 00° C. and 12° C. for 15 minutes and then washed with water (3×200 mL). The resulting mixture was dried ($Na_2SO_4$), concentrated to 76 mL total volume, and rinsed into a 125 mL Erlenmeyer flask with an additional 16 mL of DCM, to make an approximately 1 M dark purple solution of (diazomethylene)dibenzene. In a separate flask, a slurry of (S)-2-(2-((benzyloxy)

carbonyl)hydrazinyl)-3-(3,4-dihydroxyphenyl)-2-methylpropanoic acid compound with tetrahydrofuran (4:3) (30.7 g, 74.0 mmol) in IPA (300 mL) was cooled to less than 10° C. and the (diazomethylene)dibenzene solution (78 mL, 78 mmol) was added. The resulting mixture was warmed to room temperature and LC-MS showed a stalled reaction after 30 minutes. Additional diphenyldiazomethane (0.2 eq, 14 mL) was added and stirring continued at room temperature. After 35 minutes, the remaining diphenyldiazomethane solution (9 mL) was added. After 2 hours, 20 minutes, a purple color persisted and LC-MS showed that the reaction was complete. The reaction mixture was concentrated to approximately 60 mL and 20% aq. $CH_3CN$ (300 mL) was added. The mixture was washed with cyclohexane (10×300 mL), ethyl acetate (450 mL) added, and the mixture was washed with saturated aqueous $NaHCO_3$ (150 mL) and brine (60 mL). The mixture was dried ($Na_2SO_4$) and concentrated, giving (S)-benzyl 2-(1-(benzhydryloxy)-3-(3,4-dihydroxyphenyl)-2-methyl-1-oxopropan-2-yl)hydrazine-carboxylate (39.4 g, 74.8 mmol, >99% yield). $^1$H NMR (400 MHz, DMSO-$d_6$) δ 8.65 (br s, 2H), 8.19 (br s, 1H), 7.43-7.20 (m, 15H), 6.70 (s, 1H), 6.55 (d, J=2.0 Hz, 1H), 6.45 (d, J=8.0 Hz, 1H), 6.20 (dd, J=7.9, 2.0 Hz, 1H), 4.95 (d, J=3.4 Hz, 2H), 2.81 (d, J=13.6 Hz, 1H), 2.67 (d, J=13.7 Hz, 1H), 1.17 (d, J=3.1 Hz, 3H); MS (ESI) m/z 549 [M+Na]+.

Step 3

A solution of (S)-benzyl 2-(1-(benzhydryloxy)-3-(3,4-dihydroxyphenyl)-2-methyl-1-oxopropan-2-yl)hydrazinecarboxylate (39.4 g, 74.8 mmol) and $CH_3CN$ (394 mL) was cooled to less than 00° C. and DBU (27.1 mL, 180 mmol) and tetrabenzyl pyrophosphate (89 g, 165 mmol) were added at less than 00° C. After 40 minutes, water (400 mL) was added giving a biphasic solution. The layers were separated, the bottom (yellow oil) layer was washed (approximately 100 mL) with cold 1:1 $CH_3CN$/water (2×100 mL), then diluted with ethyl acetate (400 mL), and washed with brine (80 mL). the mixture was dried ($Na_2SO_4$) and concentrated. FCC (50-100% MTBE/heptanes) gave (S)-benzyl 2-(1-(benzhydryloxy)-3-(3,4-bis((bis(benzyloxy)phosphoryl)oxy)phenyl)-2-methyl-1-oxopropan-2-yl)hydrazine-carboxylate (67.2 g, 64.2 mmol, 86% yield) as a clear oil. $^1$H NMR (400 MHz, DMSO-$d_6$) δ 7.45-7.16 (m, 35H), 7.06 (d, J=8.6 Hz, 1H), 6.88 (dd, J=8.7, 2.0 Hz, 1H), 6.71 (s, 1H), 5.12 (ddt, J=9.9, 7.0, 3.9 Hz, 10H), 4.99-4.80 (m, 2H), 2.95-2.76 (m, 2H), 1.11 (d, J=1.8 Hz, 3H); MS (ESI) m/z 1069 [M+Na]+.

Step 4

A solution of (S)-benzyl 2-(1-(benzhydryloxy)-3-(3,4-bis((bis(benzyloxy)-phosphoryl)oxy)phenyl)-2-methyl-1-oxopropan-2-yl)hydrazinecarboxylate (60.6 g, 57.9 mmol) in THF (550 mL) was added to 5% Pd/C (wet JM#9) (12.1 g, 56.9 mmol) in a 2 L stainless steel pressure bottle. The mixture was shaken under 60 psi of hydrogen at 22° C. for 2 hours. The starting temperature was 12.4° C. (the solution had been stored in the freezer) and the $T_{max}$ was 31.6° C. Water (deionized, 275 mL) was then added and the hydrogenation was continued for another 17 hours. The mixture was filtered through a nylon membrane with 100 mL of washing with 1:1 THF-water. The mixture was diluted with MTBE (100 mL) and the layers were separated. The aqueous layer was washed with MTBE (3×100 mL), then concentrated on a rotary evaporator (35° C. bath temperature) to 100 g total mass, and lyophilized for 3 days to a white glass. The amorphous solid was broken up and lyophilized for one day to remove traces of additional water, giving carbidopa diphosphate (22.3 g, >99%) still containing 10 to 15 weight % water by Karl Fischer titration (85% corrected yield). $^1$H NMR (500 MHz, DMSO-$d_6$) δ 7.15 (d, J=8.3 Hz, 1H), 7.11 (s, 1H), 6.89 (dd, J=8.1, 2.1 Hz, 1H), 3.00-2.82 (m, 2H), 1.31 (s, 3H); MS (ESI) m/z 387 [M+H]+. By HPLC (Agilent Poroshell 120 EC-C18 #693975-902 4.6×150 mm column, 1 mL/minute 0.1% aq $H_3PO_4/CH_3CN$, 3 minute 97.5:2.5, 4 minute gradient to 70:30, 2 minute gradient to 0:100, hold 1 minute, detection at 220 nm), the material is 96.4% purity (peak area % at 220 nm; diphosphate retention time=2.37 minutes).

Example 4b: Synthesis of Carbidopa Diphosphate

Carbidopa 3',4'-diphosphate was prepared as shown in Scheme 4b below:

Scheme 4b

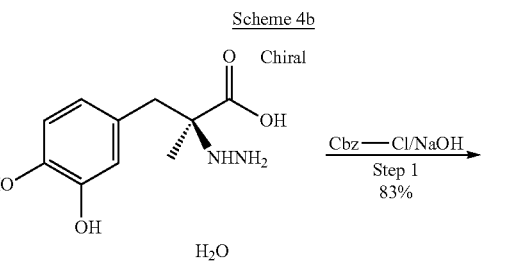

Cbz—Cl/NaOH
Step 1
83%

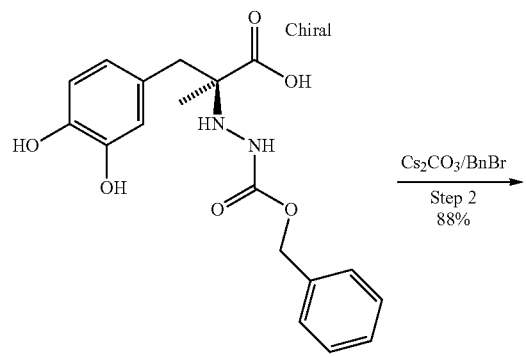

$Cs_2CO_3$/BnBr
Step 2
88%

1

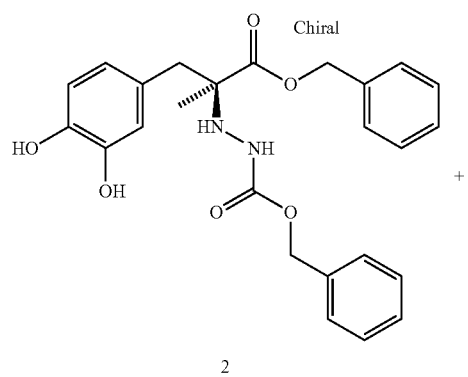

+

2

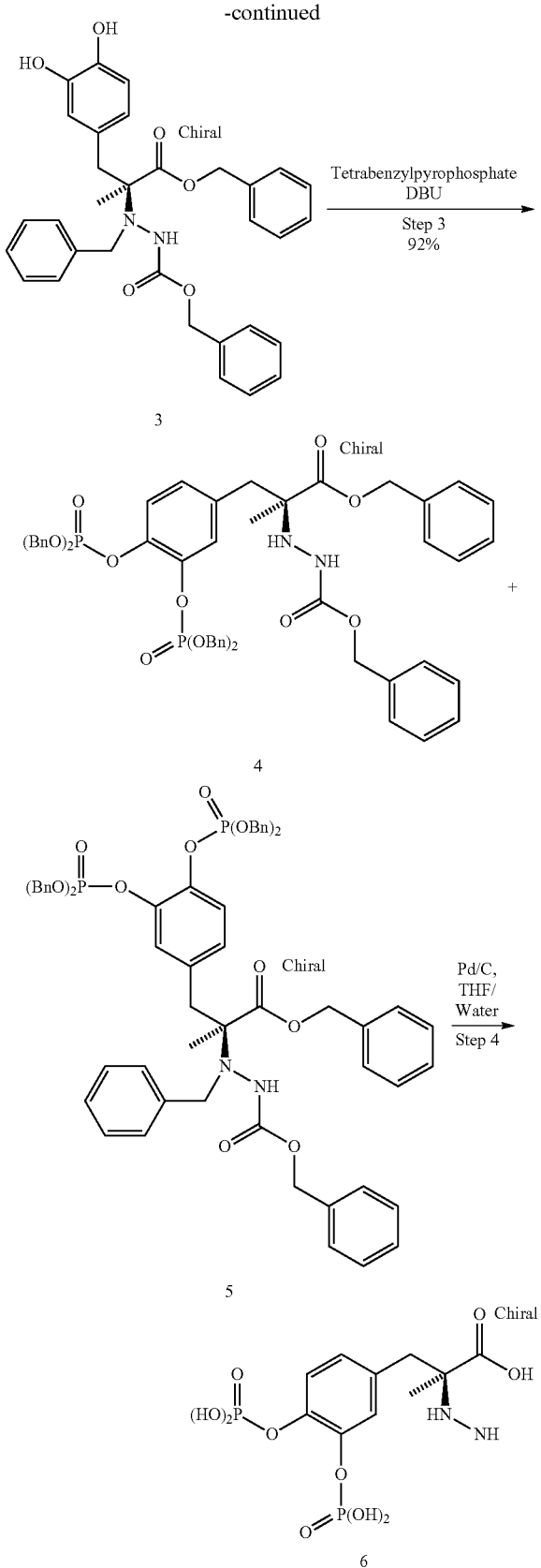

Specifically, carbidopa 3',4'-diphosphate was prepared as described in Steps 1 through 4 below.

Step 1

To a suspension of S(−)-Carbidopa (25 g, 92 mmol) in water (76 mL) was added a solution of sodium hydroxide (7.24 g, 183 mol) in water (76 mL) drop-wise over a period of 20 minutes at <5° C. After the addition of base, the mixture was stirred for 15 minutes or until the reaction mixture was a solution. To this solution was added benzylchloroformate (18.67 g, 110 mmol) in THF (101 mL) drop-wise over a period of 30 minutes at <10° C. and then the reaction mixture was allowed to warm to rt. The reaction mixture was stirred at 25° C. for 1 hr. After 1 hr, an additional 0.2 eq of benzylchloroformate (3.74 g, 3.12 mL) was added and the reaction mixture was stirred 1.5 hr at 25° C. After 1.5 h, the reaction mixture (pH=5.75) was basified to pH=9 using 10% sodium hydroxide and extracted with MTBE (3×150 mL). The organic layer was separated and discarded. The aqueous layer (pH=8.6) was acidified to pH=2.75 using 6 N HCl and extracted with MTBE (3×150 mL). The combined organic layers was washed with saturated sodium chloride solution (150 mL), dried over magnesium sulfate and partially (75%) concentrated under vacuum. To the solution was added 250 mL of THF and partially (75%) concentrated under vacuum again. To the yellow solution was added 250 mL of MTBE and concentrated to 50% by volume. The resulting white slurry was cooled to 0° C., filtered and the solid washed with cold MTBE to afford 32.31 g (white solid) of Compound 1 (potency 84.5% w/w, 95.6% pa, PAY 83%).

Step 2

Cesium carbonate (2.3 g, 7.08 mmol) was added to a solution of Compound 2 (5.0 g, 11.79 mmol) in DMF (50 mL) at 2° C. The mixture was stirred for 10 mins. To this mixture was added benzyl bromide (2.0 g, 11.79 mmol, 1.4 mL) dropwise over a period of 10 minutes at 2° C. After the addition, the reaction mixture was stirred at 25° C. for 64 hr. After 64 hr, the reaction mixture was diluted with water (150 mL) and extracted with MTBE (3×150 mL). The combined organic layers was washed with water (50 mL), brine (50 mL), dried (MgSO4), filtered and concentrated to afford 5.36 g of Compounds 2 and 3 in an 88% yield. Compound 2: MS (ESI) m/z 451 [M+H]+, Compound 3, MS (ESI) m/z 541 [M+H]+.

Step 3

To a solution of Compounds 2 and 3 (9.8 g, 21.75 mmol) in ACN (100 ml) was added tetrabenzyl pyrophosphate (29.9 g, 54.4 mmol) at −14° C. DBU (8.61 ml, 56.6 mmol) was added to the reaction mixture at −7° C. dropwise. The reaction mixture was then stirred at <0° C. for 30 mins. After 30 mins, the reaction mixture was allowed to warm to room temperature. After 1 h, the reaction mixture was quenched with water (300 mL), extracted with MTBE (2×150 mL), washed water (150 mL), brine (150 mL), dried (MgSO4), filtered and concentrated to afford 24.69 g of Compounds 4 and 5 in a 92% yield. Compound 4, MS (ESI) m/z 972 [M+H]+.

Step 4

Tetrahydrofuran (10.00 mL) was added to Compounds 4 and 5 (1.026 g, 0.980 mmol) and 5% Pd/C (50% wet JM#9) (0.199 g, 1.870 mmol, 0.10 g dry weight) in a 20 mL Barnstead w/glass liner. The mixture was stirred under 80 psig of Hydrogen at 25° C. for 1.5 hr. Water (5.00 mL) was added and the mixture was hydrogenated for another 1.5 hr. Then after 1.5 hr, the mixture was filtered through a polypropylene membrane, 2.5 mL of MTBE was added, the mixture was shaken in a separatory funnel, and the lower aqueous layer was drained. The aqueous solution was washed twice with 2.5 mL of MTBE, giving a significant reduction in volume (THF and toluene pulled into the MTBE). The colorless aq. solution (water layer) was lyophilized for 3 days, giving 385 mg of the desired product (93.9% pa) compound 6.

Example 5: Alternative Synthesis of L-Dopa 4'-Monophosphate

L-Dopa 4'-monophosphate was prepared as shown in Scheme 5 below:

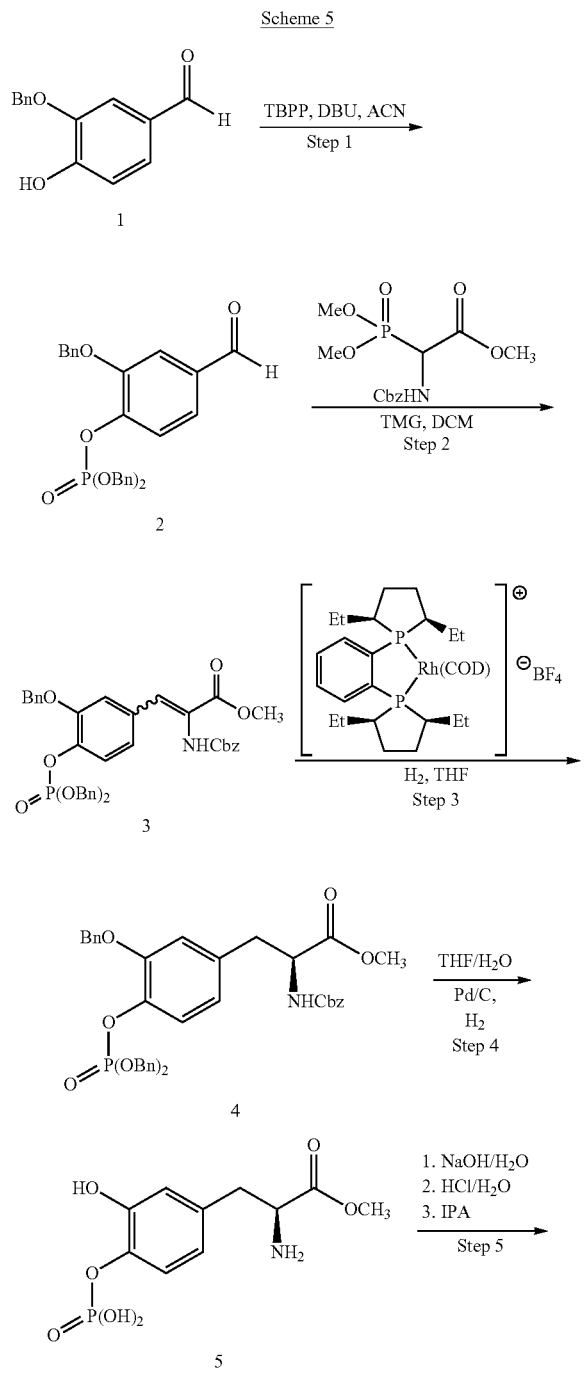

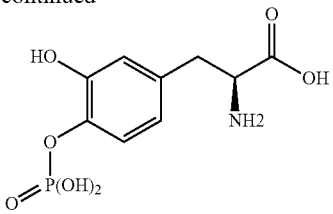

Specifically, L-Dopa 4'-monophosphate was prepared as described in Steps 1 through 5 below.

Step 1

To a solution of 3-(benzyloxy)-4-hydroxybenzaldehyde, Compound 1, (10.0 g, 43.8 mmol) in acetonitrile (100 ml) tetrabenzyl diphosphate (TBPP) (24.8 g, 46.0 mmol) at 25° C. was added. The reaction mixture was cooled to 4° C. and DBU (7.67 g, 50.4 mmol) was added to the reaction mixture. After the addition, the reaction mixture was allowed to warm to room temperature and stirred at room temperature (~20-25° C.) for 60 mins. The reaction mixture was then quenched with water (400 ml) and extracted with MTBE (3×100 mL). The organic layer was washed with saturated sodium bicarbonate solution (150 mL), water (150 mL), saturated sodium chloride solution (150 mL), and concentrated to afford Compound 2 (20.7 g, 96.5% purity, 93% yield). $^1$H NMR (400 MHz, DMSO-$d_6$) δ 9.92 (s, 1H), 7.67 (dd, J=1.8, 0.9 Hz, 1H), 7.54 (dd, J=8.1, 1.8 Hz, 1H), 7.48-7.39 (m, 3H), 7.35-7.22 (m, 13H), 5.22 (s, 2H), 5.09 (dd, J=8.2, 2.1 Hz, 4H).

Step 2

To a solution of (+/−)-benzyloxycarbonyl-alpha-phosphonoglycine trimethylester (31.1 g, 94 mmol) and dibenzyl (2-(benzyloxy)-4-formylphenyl) phosphate, Compound 2, (44.3 g, 94% purity, 85 mmol) in 443 mL of DCM at 2° C. was added 1,1,3,3-tetramethylguanidine (TMG) (11.78 g, 102 mmol). The resulting mixture was stirred at room temperature overnight. The next day the reaction mixture was washed with 3×222 mL of water and concentrated to afford 68.9 g of Compound 3. Compound 3 was then slurried with 40.5 g of silica gel 60 in 689 mL of ethyl acetate for 1 h and filtered. The filtrate was concentrated to afford 73.4 g of Compound 3 as an oil. Compound 3 was then precipitated at 4° C., and slurried in 350 mL of MTBE at 4° C. for 1 hr. The slurry was then filtered and the solid washed with cold MTBE. The solid was dried in the vacuum oven at 40° C. overnight to afford 50.4 g of Compound 3 (99.6% purity, 85% yield). $^1$H NMR (400 MHz, DMSO-$d_6$) δ 7.60 (t, J=1.4 Hz, 1H), 7.44-7.18 (m, 23H), 5.10 (qd, J=5.9, 2.6 Hz, 8H), 3.72 (s, 3H).

Step 3

Into a 2.0 gal reactor was charged Compound 3, methyl 3-(3-(benzyloxy)-4-((bis(benzyloxy)phosphoryl)oxy)phenyl)-2-(((benzyloxy)carbonyl)amino)acrylate (446.31 g, 521 mmol) in 3.6 L of THF. This solution was sparged with $N_2$ for 30 minutes. Into another 2.0 gal reactor was charged 1,2-bis[(2S,5S)-2,5-diethylphospholano]benzene(1,5-cyclooctadiene)rhodium(I) tetrafluoroborate (3.44 g, 5.21 mmol) and purged with $N_2$ 10 times then sparged with $N_2$ for 30 minutes. The starting material solution was then transferred into this reactor using $N_2$ pressure. The lines were purged with $H_2$, then the reactor was purged with $H_2$ three times. The reaction was stirred at 35° C. under 100 psig of $H_2$. After 20 hrs, HPLC showed Compound 4, with a 99% ee. The reaction solution was then transferred into a 12 L extractor and 3.6 L of ethyl acetate was added. The solution was washed 2× with 3.7 L of 5 wt % cysteine/8% sodium bicarbonate followed by 3.6 L of 5 wt % aq NaCl. The organic layer was separated and stirred with 43.4 g of ENO-PC activated carbon at room temperature under $N_2$ overnight. The mixture was filtered and the filtrate concentrated to afford Compound 4 (420.1 g, (oil), 88% w/w purity, 100% yield, chiral purity: 99% ee. The crude product (S)-methyl 3-(3-(benzyloxy)-4-((bis(benzyloxy)phosphoryl)oxy)phenyl)-2-(((benzyloxy)carbonyl)amino)propanoate, Compound 4, was used, as is, in the next step. $^1$H NMR (400 MHz, DMSO-$d_6$) δ 7.85 (d, J=8.1 Hz, 1H), 7.46-7.16 (m, 21H), 7.09 (dd, J=8.2, 1.4 Hz, 1H), 6.81 (dd, J=8.2, 1.9 Hz, 1H), 5.09-4.98 (m, 8H), 4.31 (ddd, J=10.2, 8.1, 5.0 Hz, 1H), 3.63 (s, 3H), 3.08-2.78 (m, 2H).

Step 4

To a 150-mL Parr hydrogenator was added 10 wt % on a dry basis of 5% Pd/C (1.33 g, catalyst contains 63.6% H2O). Charged a 2.9 wt % aqueous sodium bicarbonate solution (20.7 g) to the reactor. Compound 4 (5.70 g, 85% potency) was dissolved in THF (48.5 mL, 10 mL/g of substrate) and then transferred to the reactor. Pressurized the reactor with argon to 60 psig and vented pressure to 10 psig; perform argon pressure purge a total of 6 times. In a similar fashion, pressure purged the reactor with hydrogen 3 times (fill to 50 psig, vent to 5 psig). Refilled the reactor to 50 psig of H2 and agitated at 750 rpm at 25° C. for at least 2 h. Following reaction completion, filtered the biphasic solution to remove the catalyst. Rinsed the reactor and filter cake with water (4.1 mL, 2 mL/g relative to theoretical yield of product). The biphasic reaction mixture was diluted with 16 mL of MTBE. The aqueous layer was removed and washed with 16 mL of MTBE. The aq layer was then transferred to a 250-mL flask and quantity sufficient 6 M aq HCl was added to adjust to pH 1.8. Mixed the solution vigorously, then added iPrOH (73 mL) to bring final solvent composition to 3:1 iPrOH/water. The slurry was stirred overnight. The crystallization slurry was filtered and the wetcake solids were washed with iPrOH. The white solid was dried in the vacuum oven at 50° C. to afford Compound 5 (1.72 g, crystalline solid, 85% yield). 1H NMR (400 MHz, Deuterium Oxide) δ 7.25 (dt, J=8.3, 1.1 Hz, 1H), 6.87 (t, J=1.5 Hz, 1H), 6.80 (dd, J=8.3, 2.2 Hz, 1H), 4.41 (ddd, J=7.9, 5.4, 0.7 Hz, 1H), 3.87 (d, J=0.7 Hz, 3H), 3.36-3.08 (m, 2H).

Step 5

To a solution of Compound 5, (S)-methyl 2-amino-3-(3-hydroxy-4-(phosphonooxy)phenyl)propanoate, (10.0 g, 34.3 mmol) in 40 mL of water at 15-20° C. was added 22.89 mL (4.0 eq) of 6 N NaOH. When the pH reached 7-8 the solution was passed through a filter for clarification. After clarification, the pH adjustment was continued. After the base was added, the rxn mixture was stirred at 25° C. for 60 mins (pH=12.06). After 60 mins the reaction mixture was acidified with 4.0 eq 6N HCL (137 mmol, 22.89 mL). The final pH was adjusted to 1.8. After 10 mins the rxn mixture became cloudy and 200 mL of IPA was added. The slurry was stirred for 30 mins and the solid was filtered and washed with IPA. The solid was dried in the vacuum oven at 40° C. overnight to afford Compound 6, (S)-2-amino-3-(3-hydroxy-4-(phosphonooxy)phenyl)propanoic acid (7.85 g, 99% purity, 87% yield, 99.6% ee). $^1$H NMR (400 MHz, Deuterium Oxide) δ 7.24 (dd, J=8.3, 1.3 Hz, 1H), 6.91 (d, J=2.1 Hz, 1H), 6.83 (dd, J=8.3, 2.2 Hz, 1H), 4.25 (dd, J=8.0, 5.2 Hz, 1H), 3.35-3.05 (m, 2H).

Example 6: Alternative Synthesis of L-Dopa 4'-Monophosphate

L-Dopa 4'-monophosphate was prepared as shown below:

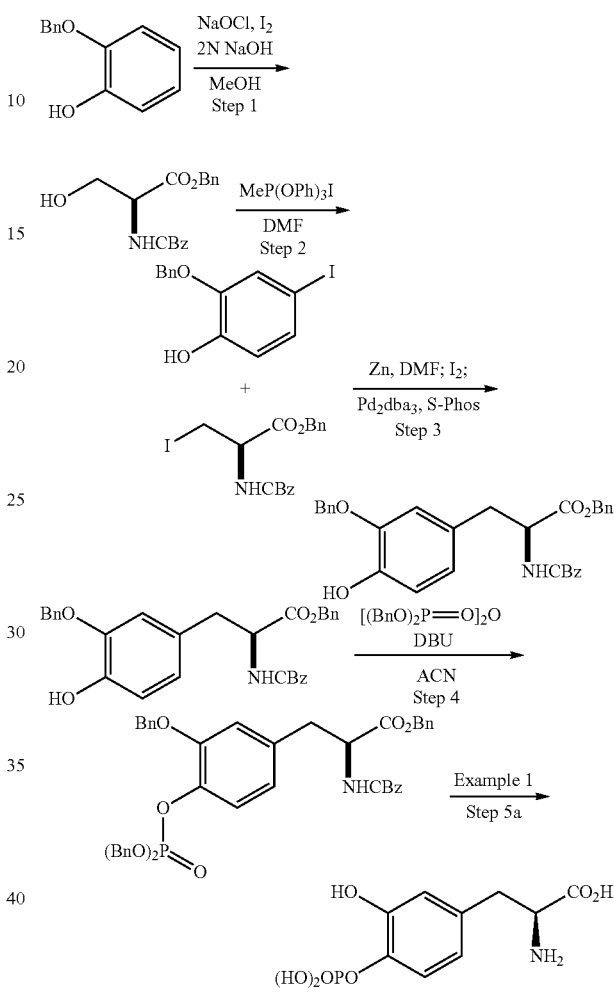

Step 1

A solution of 2-(benzyloxy)phenol (63.7 ml, 364 mmol) in MeOH (1050 ml) was cooled to −10° C. and sodium iodide (54.5 g, 364 mmol) and sodium hydroxide (382 ml, 764 mmol) were added (NaOH over 5 min, temp to 10° C. and dark solution with NaOH addition). Cooled back to <5° C. and added sodium hypochlorite (247 ml, 400 mmol) dropwise, keeping the temperature at <5° C. After 10 min, removed 500 mL MeOH by rotary evaporation, then added MTBE (730 mL) and 2 N HCl (909 ml, 1818 mmol), washed with 1 N $Na_2S_2O_3$ (130 mL×3; lighter each time) and brine (64 mL), dried ($Na_2SO_4$), conc, and flushed with cyclohexane (100 mL) to a crude yellow solid. Added cyclohexane (130 mL), heated to 55° C. (yellow solution), then cooled slowly, seeding at 45° C. (~50 mg—solution) and 40° C. (~50 mg, slurry developed). Continued cooling to room temperature (~20-25° C.) and stirred vigorously overnight. Filtered, washing with cyclohexane (64 mL), giving crop 1 material (69.93 g, 59%, very pure by 1H NMR, slightly off-white solid). Concentrated the mother liquors to ~70 mL, seeded, aged 1 h, and sticky dark material was precipitating with product. Added MTBE (7 mL), sonicated (good for color dissolution), stirred 20 min, and filtered. Washed with 10% MTBE/cyclohexane (32 mL), giving crop 2 material (4.65 g, some small impurities by 1H NMR). Overall, isolated 2-(benzyloxy)-4-iodophenol (74.6 g, 229 mmol, 62.9% yield). $^1$H NMR (501 MHz, DMSO-d6) δ 9.33 (s, 1H), 7.49-7.42 (m, 2H), 7.42-7.35 (m, 2H), 7.35-7.29 (m, 1H), 7.24 (d, J=2.0 Hz, 1H), 7.09 (dd, J=8.3, 2.1 Hz, 1H), 6.64 (d, J=8.3 Hz, 1H), 5.09 (s, 2H).

Step 2

A solution of (S)-benzyl 2-(((benzyloxy)carbonyl) amino)-3-hydroxypropanoate (150 g, 455 mmol) in DMF (750 ml) was cooled to 0° C. and methyltriphenoxyphosphonium iodide (247 g, 547 mmol) was added (no exotherm). After 20 min between 5 and −5° C., complete by LC-MS. After 30 min, added sodium bicarbonate (19.13 g, 228 mmol) and MTBE (750 mL, temp to 8° C.), then carefully added water (750 mL, minor $CO_2$ evolution early in addition), keeping the temp <20° C. Washed into a separatory funnel with additional water (750 mL, total 1.5 L, 10 vol) and MTBE (750 mL, total 1.5 L, 10 vol), aq pH~8. Separated layers, washed the organic layer with brine (300 mL), and checked layers by LC-MS. Dried ($Na_2SO_4$), conc to minimal volume (401 g total mass), and added MeOH (3.0 L, yellow solution). Added water (1.5 L) over 30 min, seeding with previously isolated crystalline material (0.1 wt %, 150 mg) after 2 vol, 300 mL water had been added (did not dissolve). A slurry gradually developed, then rapidly thickened after 650 mL water had been added. After stirring at ambient temperature for 30 min, filtered the white slurry, washing with 2:1 MeOH/water (300 mL slurry wash, 300 mL displacement wash) and left on the glass frit with vacuum for 12 h. Added MeOH (2.25 L, 15 vol) to the wet cake, stirred vigorously for 30 min to break up the slurry, then added water (1.125 L) over 30 min, stirred additional 15 min, and filtered, washing with 2:1 MeOH/water (300 mL displacement wash). Dried the white solid in a vacuum oven at 50° C. to constant weight, giving (R)-benzyl 2-(((benzyloxy)carbonyl)amino)-3-iodopropanoate (173 g, 394 mmol, 86% yield). $K_f$ titration showed 253 ppm water. $^1$H NMR (400 MHz, DMSO-d6) δ 7.96 (d, J=8.3 Hz, 1H), 7.44-7.14 (m, 10H), 5.10 (d, J=33.8 Hz, 4H), 4.38 (td, J=8.7, 4.6 Hz, 1H), 3.55 (dd, J=10.3, 4.6 Hz, 1H), 3.37 (t, J=9.7 Hz, 1H). MS (ESI) m/z 457 [M+$NH_4$]+.

Step 3

A slurry of zinc (47.0 g, 719 mmol) and DMF (325 ml) was stirred in a 2 L 3-neck round-bottom flask with magnetic stirring. The gray slurry was cooled to 16° C. in an ice bath and iodine (7.60 g, 29.9 mmol) was added (yellow to clear supernatant immediately with exotherm from 16 to 27° C.). Cooled back to 10° C. and added (R)-benzyl 2-(((benzyloxy) carbonyl)amino)-3-iodopropanoate (105 g, 240 mmol) portionwise over 10 min at <25° C. After an additional 10 min between 20 and 25° C., LCMS showed complete zinc insertion (aliquot 2N HCl quench). Added $Pd_2(dba)_3$ (0.457 g, 0.499 mmol), 2-dicyclohexylphosphino-2',6'-dimethoxy-biphenyl (0.410 g, 0.998 mmol), and 2-(benzyloxy)-4-iodo-phenol (65.1 g, 200 mmol) in one portion (no exotherm) and stirred at room temperature (start=2:30). After 1 h, an exotherm to 27° C. was observed, so cooled in a room temperature water bath back to 20-25° C. and stirred overnight. After 15 h, 40 min, LC-MS showed complete and clean reaction. Added MTBE (650 mL) and silica (65 g), stirred 15 min, and filtered the gray slurry, washing the gray solid with MTBE (325+130 mL). Washed the yellow filtrate with satd aq $NH_4Cl$ (325 mL, temp to 27° C. with a small amount of $H_2$ evolution, at pH ~5-6) and brine (130 mL), dried ($Na_2SO_4$), conc, and FCC (800 g column, 50-100% DCM/heptanes, then to 10% MTBE/DCM; only separating non-polar highly colored impurities and baseline material, upgrading HPLC pa % from 91 to 93 pa %) gave (S)-benzyl 3-(3-(benzyloxy)-4-hydroxyphenyl)-2-(((benzyloxy)carbo-nyl)amino)propanoate (106 g, 207 mmol, 104% yield) as a light brown oil. $^1$H NMR showed extra mass primarily CBz alanine Bn ester from protonation of excess alkylzinc during workup. Used without further purification in the next step, assuming quantitative yield. $^1$H NMR (501 MHz, DMSO-d6) δ 8.86 (s, 1H), 7.80 (d, J=8.0 Hz, 1H), 7.47-7.41 (m, 2H), 7.41-7.08 (m, 13H), 6.94 (d, J=2.0 Hz, 1H), 6.70 (d, J=8.0 Hz, 1H), 6.63 (dd, J=8.0, 1.9 Hz, 1H), 5.15-4.93 (m, 6H), 4.27 (ddd, J=9.7, 7.9, 5.5 Hz, 1H), 2.93 (dd, J=13.8, 5.5 Hz, 1H), 2.78 (dd, J=13.8, 9.8 Hz, 1H). MS (ESI) m/z 512 [M+H]+.

Step 4

A solution of (S)-benzyl 3-(3-(benzyloxy)-4-hydroxyphe-nyl)-2-(((benzyloxy)carbonyl)amino)propanoate (102 g, 200 mmol) in ACN (510 ml) was stirred at room temperature and tetrabenzyl pyrophosphate (118 g, 220 mmol) was added. Cooled in an ice bath and added DBU (45.2 ml, 300 mmol) over 10 min, keeping the temp between 20 and 25° C. After 30 min, LC-MS showed complete reaction. Added MTBE (1.0 L) and water (510 mL), separated layers (very little aq loss by LCMS), and washed the org layer with brine (3×200 mL). Dried ($Na_2SO_4$), conc, and FCC (split in two portions; each purified on an 800 g column with 25-75% MTBE/heptanes gradient elution, then combined) gave (S)-benzyl 3-(3-(benzyloxy)-4-((bis(benzyloxy)phosphoryl) oxy)phenyl)-2-(((benzyloxy)carbonyl)amino)propanoate (132 g, 171 mmol, 86% yield) as an amber oil. $^1$H NMR (400 MHz, DMSO-d6) δ 7.87 (d, J=8.1 Hz, 1H), 7.43-7.17 (m, 26H), 7.07 (dd, J=8.2, 1.3 Hz, 1H), 6.79 (dd, J=8.3, 1.9 Hz, 1H), 5.14-4.91 (m, 10H), 4.38 (ddd, J=10.0, 8.0, 5.2 Hz, 1H), 3.05 (dd, J=13.8, 5.2 Hz, 1H), 2.88 (dd, J=13.8, 10.1 Hz, 1H). MS (ESI) m/z 789 [M+$NH_4$]+.

The preparation of levodopa 4'-monophosphate was completed as with Step 5a from Example 1.

Example 7: Alternative Synthesis of Carbidopa 4'-Monophosphate

Carbidopa 4'-monophosphate was prepared as shown in Scheme 7 below:

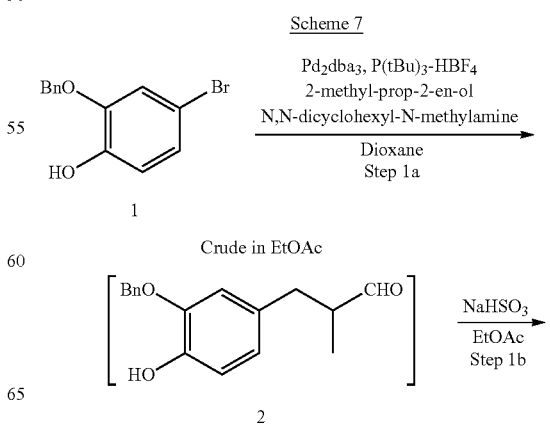

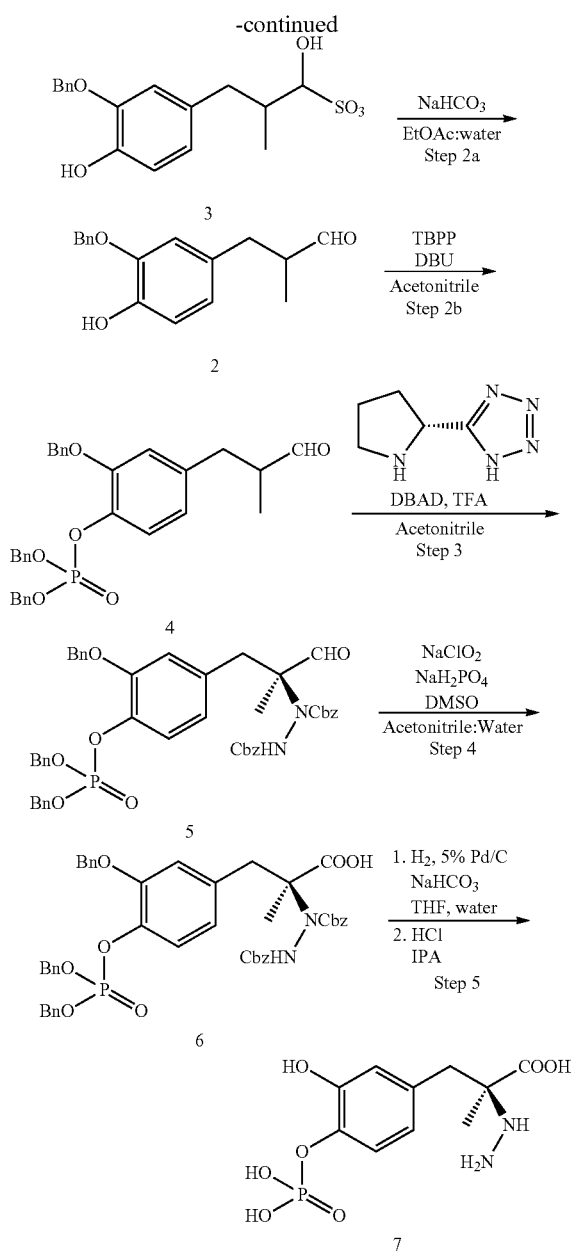

Specifically, Carbidopa 4'-monophosphate was prepared as described in Steps 1 through 5 below.

Step 1

A 500 mL three-neck round bottom flask was charged with compound 1 (25.04 g, 90 mmol), tris(dibenzylideneacetone)palladium (1.23 g, 1.343 mmol), tri-tert-butylphosphonium tetrafluoroborate (0.875 g, 3.02 mmol), and a stir bar. A thermocouple, reflux condenser, and stopper were placed onto the three necks of the flask. The flask was purged with nitrogen for 1 h. During this time, a second flask was charged with dioxane (200.0 mL), 2-methylprop-2-en-1-ol (8.30 mL, 99 mmol), and N-cyclohexyl-N-methylcyclohexanamine (30.0 mL, 140 mmol), and this flask was sparged with nitrogen for 1 h. The dioxane solution was then transferred via cannula into the flask containing compound 1, palladium and ligand. The reaction mixture was heated to 100° C. for 1 h. After this time, the reaction was cooled to 35° C. and diluted with ethyl acetate (250 mL) and 1.0 M HCl (250 mL). The biphasic mixture was stirred for 10 min and phase cut. The organic solution was removed from the reactor and the aqueous phase returned. Ethyl acetate (150 mL) was added to the aqueous material and the mixture was agitated for 10 min. The aqueous layer was drained from the reaction, and the original ethyl acetate was returned to the reactor. This combined mixture was washed (2×10 min with stirring) with 5% N-acetylcysteine/8% sodium bicarbonate mixture. After separating the aqueous waste after each wash, the yellow organic solution was filtered through Celite® diatomaceous earth. Karl Fischer titration of the organic reaction mixture showed that the content of water was 3.3 wt %. The yellow organic solution was returned to the reactor and stirred as sodium bisulfite (18.67 g, 179 mmol) was added. The reaction mixture was heated to 40° C. for 13 h. After this time, the precipitate was filtered and the solid was washed with ethyl acetate (3×100 mL) to give a white solid in 64.2% yield. The potency of the material was determined to be 60.0% by Q-NMR spectroscopy. 1H NMR (400 MHz, D2O, 1:1 diastereomers): b ppm 7.48-7.36 (m, 5H), 6.92 (m, 1H), 6.86 (dd, J=8.0, 4.0 Hz, 1H), 6.76 (dd, J=8.0, 4.0 Hz, 1H), 5.21-5.19 (m, 2H), 4.27-4.25 (m, 1H), 3.10-3.05 (m, 0.5H), 2.68-2.63 (m, 0.5H), 2.52-2.49 (m, 0.5H), 2.38-2.16 (m, 1.5H), 0.94 (d, J=8.0 Hz, 1.5H), 0.84 (d, J=8.0 Hz, 1.5H).

Step 2a

To a 500-mL 3-neck round bottom flask with attached thermocouple and overhead stirring was charged compound 3 (15.05 g, 63.3% w/w, 23.2 mol), sodium bicarbonate (16.97 g, 202 mmol), water (155 mL) and ethyl acetate (140 mL). The resulting biphasic suspension was stirred vigorously at 25° C. After the complete consumption of starting material, the reaction was transferred to a separatory funnel and the layers separated. The organic layer was washed with brine (75 mL). The organic layer was dried over sodium sulfate, and concentrated in vacuo to provide compound 2 as a white solid (6.22 g, 62.9%). 1H NMR (400 MHz, CDCl3): δ ppm 9.68 (d, J=2.0 Hz, 1H), 7.46-7.32 (m, 5H), 6.86 (d, J=8.0 Hz, 1H), 6.73 (d, J=1.6 Hz, 1H), 6.68 (dd, J=8.0, 1.6 Hz, 1H), 5.58 (s, 1H), 5.08 (s, 2H), 2.98 (dd, J=13.6, 6.0 Hz, 1H), 2.65-2.56 (m, 1H), 2.53 (dd, J=13.6, 8.0 Hz, 1H), 1.05 (d, J=6.8 Hz, 3H).

Step 2b

To a 250-mL 3-neck flask with attached thermocouple and overhead stirring was added compound 2 (6.29 g, 23.22 mmol) followed by acetonitrile (63 mL). Then tetrabenzyl pyrophosphate (13.54 g, 24.38 mmol) was added at 25° C. The reaction was cooled to 2.1° C. in an ice bath and DBU (4.55 mL, 30.2 mmol) was added to the reaction mixture dropwise and the resulting solution was stirred at 2° C. After the complete consumption of starting material, the reaction mass was diluted with water (65 mL) and extracted with MTBE (130 mL). The combined organic layer was washed with water (65 mL), 5% sodium chloride solution (30 mL), dried over sodium sulfate, and concentrated in vacuo to provide crude compound 4 as a yellow oil (11.38 g, 92.4%). 1H NMR (400 MHz, CDCl3): δ ppm 9.75 (d, J=1.2 Hz, 1H), 7.46-7.42 (m, 2H), 7.36-7.23 (m, 13H), 7.17 (dd, J=8.0, 1.2 Hz, 1H), 6.81 (dd, J=2.0, 1.2 Hz, 1H), 6.72 (dd, J=8.0, 2.0 Hz, 1H), 5.11 (s, 2H), 5.10 (s, 2H), 5.07 (s, 2H), 3.05 (dd, J=13.6, 5.6, Hz, 1H), 2.69-2.59 (m, 1H), 2.56 (dd, J=13.6, 8.0 Hz, 1H), 1.09 (d, J=7.2 Hz, 3H).

Step 3

To a 500-mL 3-neck round bottom flask with attached thermocouple was added (R)-5-(pyrrolidin-2-yl)-1H-tetrazole (0.15 g, 1.07 mmol) and acetonitrile (40 mL). TFA (0.084 mL, 1.07 mmol) was then added followed by (E)- dibenzyl diazene-1,2-dicarboxylate (8.25 g, 27.7 mmol). Then a solution of compound 4 (11.4 g, 21.49 mmol) in acetonitrile (70 mL) was added via cannula. The resulting solution was stirred at 25° C. After the complete consumption of starting material, the reaction mixture was diluted with acetonitrile (88 mL) and water (58 mL) was added to precipitate the product. The resulting slurry was stirred overnight at 25° C. and then filtered and washed with 28 wt % water in acetonitrile (30 mL) to provide compound 5 (8.9 g, 50% yield) as a white solid. 1H NMR (400 MHz, CDCl$_3$): δ ppm 9.72 (s, 1H), 7.42-7.17 (m, 25H), 7.09-7.05 (m, 1H), 6.67-6.34 (m, 2H), 5.80 (bs, 1H), 5.30-4.80 (m, 10H), 3.39-3.21 (m, 1H), 2.92-2.77 (m, 1H), 1.14-1.00 (bs, 3H).

Step 4

A 100 mL three-neck round bottom flask was fit with a thermocouple and charged with compound 5 (5.10 g, 6.15 mmol), acetonitrile (50.0 mL), and dimethyl sulfoxide (DMSO) (1.00 mL, 14.1 mmol). The white suspension was stirred and a 2.0 mL water solution of sodium dihydrogenphosphate monohydrate (1.78 g, 12.90 mmol) was prepared and added to the reaction. Following this addition, a 2.0 mL water solution of sodium chlorite (2.88 g (80 wt %), 25.5 mmol) was added dropwise over 90 s. The cloudy reaction turned light yellow and more deep yellow and became more clear as the reaction proceeded. After 90 min, the reaction was quenched with a 6.0 mL water solution of sodium sulfite (1.60 g, 12.7 mmol). The reaction was stirred for 20 min after the sulfite addition. After this time, the reaction was poured into a separatory funnel and the round bottom flask was rinsed with 50 mL of isopropyl acetate and 50 mL of water. The aqueous and organic layers were separated. The organic layer was washed with 50 mL of water. An emulsion formed upon shaking the layers. At this time, 20 mL of brine was then added and the phases separated upon disappearance of the emulsion. An additional 50 mL of isopropyl acetate was added to the reaction, and the flask was put on a rotary evaporator until the reaction mixture appeared cloudy. The total volume of the reaction mixture after distillation was ~10 mL. The reaction flask was put into the 4° C. refrigerator for 16 h. After this time, the white solid that formed was collected, washed with 20 mL of isopropyl acetate, and dried in vacuo to give 75.0% yield of compound 6. 1H NMR (400 MHz, CDCl3): δ ppm 7.58-7.14 (m, 26H), 7.01-6.84 (m, 1H), 6.41-6.29 (m, 1H), 5.46-4.64 (m, 10H), 3.80-3.49 (m, 1H), 3.02-2.94 (m, 1H), 1.19 (br s, 3H).

Step 5

A 1-gallon Parr reactor was charged with 5 wt % dry basis of 5% Pd/C (63.6% H2O, 15.0 g), water (182 mL) and 5 wt % aqueous sodium bicarbonate (215 mL). To the aqueous catalyst slurry was added a THF solution (1090 mL) of compound 6 (109 g, 85% potent). The reactor was assembled and inerted with nitrogen, followed by purging with hydrogen (4×30 psig pressure purges). The reactor was then re-pressurized to 30 psig with hydrogen. The reactor was vigorously agitated at 25° C. for at least 1 h. Upon obtaining complete reaction conversion, hydrogen was vented and the reactor was inerted with nitrogen. The biphasic reaction mixture was then filtered to remove the catalyst, followed by rinsing with water (93 mL). The biphasic reaction mixture was diluted with MTBE (370 mL). The mixture was stirred for 15 min, then allowed to settle for 10 min (note the product is contained in the aqueous layer). Separated the layers and washed the aqueous layer with MTBE (370 mL) as described above.

Using quantity sufficient 6 M aqueous HCl, the solution is acidified to pH 1.9. Seeded the aqueous solution with 0.1 wt % of compound 7 to induce nucleation. Added isopropanol (1326 mL) to the seed slurry and mixed for at least 5 h at ambient temperature. The slurry was filtered to collect the product, recirculating the liquors as a rinse if necessary. Washed the wetcake solids with isopropanol (370 mL). The product solids were air-dried on the funnel for 2 h. Isolated 38.5 g of compound 7 as the trihydrate (97.2% potency adjusted yield). 1H NMR (400 MHz, D20): δ ppm 7.21 (d, J=8.0 Hz), 6.87 (d, J=2.0 Hz, 1H), 6.77 (dd, J=8.0, 2.0 Hz, 1H), 3.19 (d, J=16.0 Hz, 1H), 3.00 (d, J=16.0 Hz, 1H), 1.54 (s, 3H).

Example 8: Synthesis of L-Dopa 3'-Phonoxymethyl Ester

L-dopa 3'-phonoxymethyl ester was prepared as shown in Scheme 8 below:

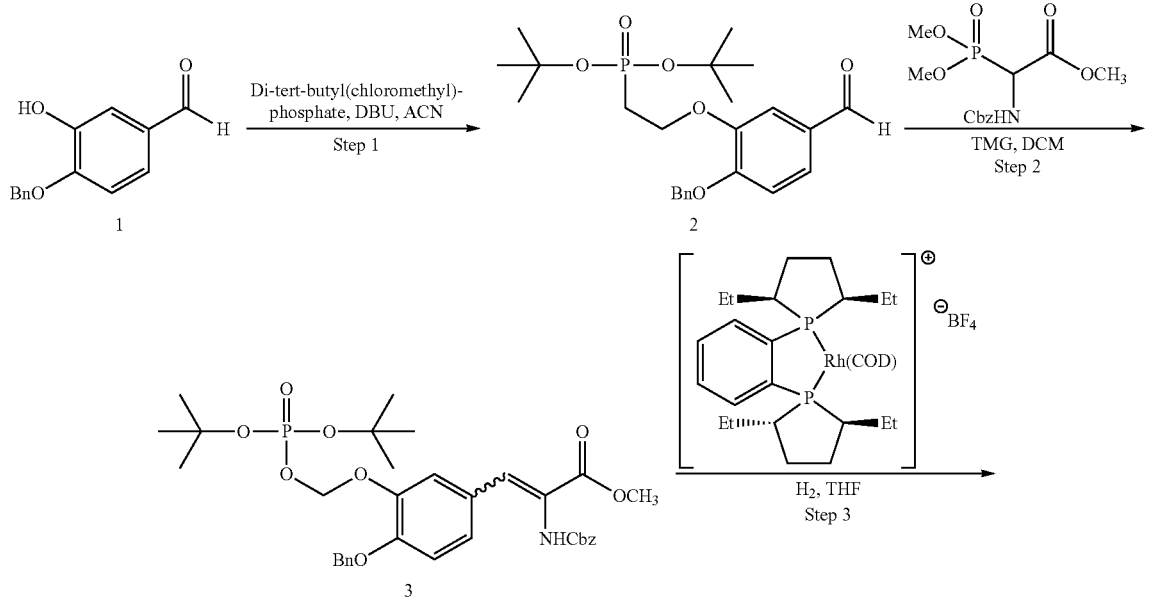

Scheme 8

-continued

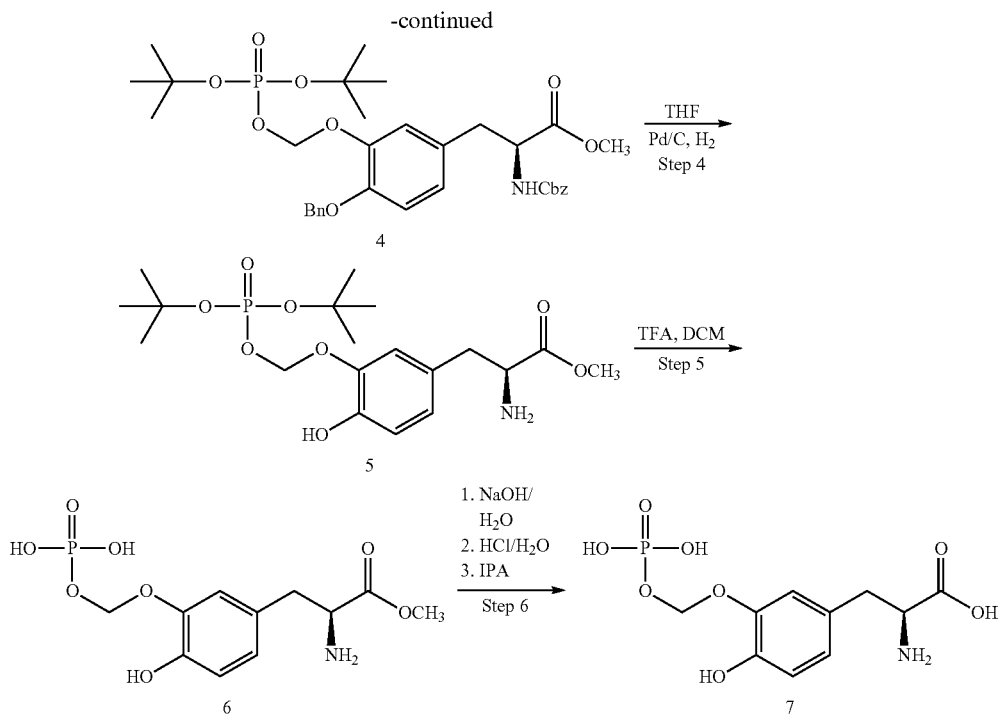

Specifically, L-dopa 3'-phonoxymethyl ester was prepared as described in Steps 1 through 6 below.

Step 1

To a solution of 4-(benzyloxy)-4-hydroxybenzaldehyde, Compound 1, (10.0 g, 43.8 mmol) in acetonitrile (133 ml) was added di-tert-butyl(chloromethyl)phosphate (12.53 g, 46.0 mmol) at 25° C. The reaction mixture was cooled to 4° C. and DBU (7.67 g, 50.4 mmol) was added. After the addition, the reaction mixture was allowed to warm to room temperature (~20-25° C.) and then heated to 50° C. for 39 h. After 22 h the reaction mixture cooled to room temperature and quenched with water (400 ml) and extracted with MTBE (3×100 mL). The organic layer was washed with saturated sodium bicarbonate solution (150 mL), water (150 mL), saturated sodium chloride solution (150 mL), and concentrated to afford Compound 2 (19.48 g, 49% purity, 50% yield. The crude product was passed down a silica gel column using a ethyl acetate-hexane gradient to afford 8.08 g of Compound 2 (94% purity, 40% yield. $^1$H NMR (400 MHz, DMSO-d$_6$) δ 9.85 (s, 1H), 7.66 (dd, J=8.3, 1.9 Hz, 1H), 7.63 (d, J=2.0 Hz, 1H), 7.49-7.44 (m, 2H), 7.43-7.32 (m, 4H), 5.65 (d, J=12.0 Hz, 2H), 5.25 (s, 2H), 1.36 (d, J=0.6 Hz, 18H).

Step 2

To a solution of (+/−)-benzyloxycarbonyl-alpha-phosphonoglycine trimethylester (5.35 g, 16.14 mmol) and 2-(benzyloxy)-5-formylphenoxy)methyl di-tert-butyl phosphate, Compound 2, (6.78 g, 14.67 mmol) in 70 mL of DCM at 00° C. was added 1,1,3,3-tetramethylguanidine (TMG) (2.0 g, 17.60 mmol). The resulting reaction mixture was stirred at room temperature overnight. The next day the reaction mixture was washed with 3×35 mL of water and concentrated to afford 13.11 g of crude product. The crude product was then purified by column chromatography on silica gel using ethyl acetate-hexane gradient to afford 7.34 g of Compound 3 (81% purity, 62% yield. $^1$H NMR (400 MHz, DMSO-d$_6$) δ 7.50-7.28 (m, 13H), 7.21 (s, 1H), 7.16 (s, 1H), 5.59 (d, J=11.9 Hz, 2H), 5.18 (s, 2H), 5.09 (d, J=12.1 Hz, 2H), 3.69 (s, 3H), 1.35 (d, J=0.5 Hz, 18H).

Step 3

Into a 120 ml parr reactor was charged methyl 3-(4-(benzyloxy)-3-(((di-tert-butoxyphosphoryl)oxy)methoxy)phenyl)-2-(((benzyloxy)carbonyl)amino)acrylate, Compound 3, (7.34 g, 9.07 mmol) and 1,2-bis[(2S,5S)-2,5-diethylphospholano]benzene(1,5-cyclooctadiene)rhodium (I) tetrafluoroborate (0.060 g, 0.091 mmol) and tetrahydrofuran (59.5 ml). The mixture was purged with H$_2$ and the reaction mixture was stirred at 35° C. under 100 psig of H$_2$ for 20 hrs. After 20 hrs, the reaction mixture was concentrated and purified by column chromatography on silica gel using ethyl acetate-hexane gradient to afford 5.44 g of Compound 4 (76% purity, 69% yield, 98% ee). $^1$H NMR (400 MHz, DMSO-d$_6$) δ 7.80 (d, J=8.0 Hz, 1H), 7.48-7.25 (m, 10H), 7.04 (d, J=2.1 Hz, 1H), 7.01 (d, J=8.4 Hz, 1H), 6.89 (dd, J=8.3, 2.1 Hz, 1H), 5.55 (dd, J=11.6, 1.6 Hz, 2H), 5.08 (s, 2H), 4.99 (d, J=2.7 Hz, 2H), 4.22 (ddd, J=9.8, 7.9, 5.2 Hz, 1H), 3.62 (s, 3H), 3.03-2.67 (m, 2H), 1.37 (d, J=1.2 Hz, 18H).

Step 4

Into a 50 mL parr reactor was charged 5% Pd/C (JM #9) δ 0.418 g, 2.311 mmol). The (S)-methyl 3-(4-(benzyloxy)-3-(((di-tert-butoxyphosphoryl)oxy)methoxy)phenyl)-2-(((benzyloxy)carbonyl)amino)propanoate, Compound 4, (2.0 g, 2.311 mmol) was dissolved in tetrahydrofuran (15.2 ml). This solution was charged into the reactor and purged with argon followed by H$_2$. The reaction mixture was stirred under 50 psig of H$_2$ at room temperature for 1 hour. After 1 h, the catalyst was filtered off and washed with THF. The solution was concentrated and purified by column chromatography on silica gel using ethyl acetate-methanol to afford 1.04 g of Compound 4, (95% purity, 98% yield). $^1$H NMR (400 MHz, DMSO-d$_6$) δ 9.13 (s, 1H), 6.88 (d, J=1.9 Hz, 1H), 6.74 (d, J=8.1 Hz, 1H), 6.71 (d, J=2.0 Hz, 1H), 5.50 (d, J=11.4 Hz, 2H), 3.58 (s, 3H), 3.49 (t, J=6.6 Hz, 1H), 2.81-2.58 (m, 2H), 1.70 (s, 2H), 1.39 (d, J=0.6 Hz, 18H).

Step 5

(S)-methyl 2-amino-3-(3-(((di-tert-butoxyphosphoryl)oxy)methoxy)-4-hydroxyphenyl)propanoate, Compound 5, (1.04 g, 2.34 mmol) in 10 mL of DCM at 5° C. was added 876 uL (5.0 eq) of trifluoroacetic acid dropwise. The reaction mixture was stirred at 25° C. until completed. After 60 mins, the starting material was consumed and the product gummed out of the DCM layer. The product, Compound 6, was extracted from the DCM layer with 3 mL of water. The aqueous layer was then taken, as is, to the next step. LC/MS [M+1]=322.1

Step 6

(S)-methyl 2-amino-3-(4-hydroxy-3-((phosphonooxy)methoxy)phenyl)propanoate, Compound 6, (752 mg, 2.341 mmol) in 4 mL of water at 5° C. was added 2.62 mL of 6 N NaOH dropwise over 5 min to a pH=12.5. The rxn mixture was stirred at 25° C. until completed. After 60 mins the reaction mixture was acidified with 6N HCL to a pH=1.9. To this solution was added IPA until the product precipitated out while maintaining the pH of 1.9. The product, Compound 7, was filtered and washed with IPA to afford, 630 mg, with a purity of 90%. $^1$H NMR (400 MHz, Deuterium Oxide) δ 7.17 (d, J=1.8 Hz, 1H), 6.99-6.96 (m, 1H), 6.94 (dd, J=8.3, 1.8 Hz, 1H), 5.57 (d, J=12.6 Hz, 2H), 4.16 (dd, J=7.9, 5.1 Hz, 1H), 3.33-3.05 (m, 2H).

Example 9: Synthesis of L-Dopa 4'-Phonoxymethyl Ester

L-dopa 4'-phonoxymethyl ester was prepared as shown in Scheme 9 below:

Scheme 9

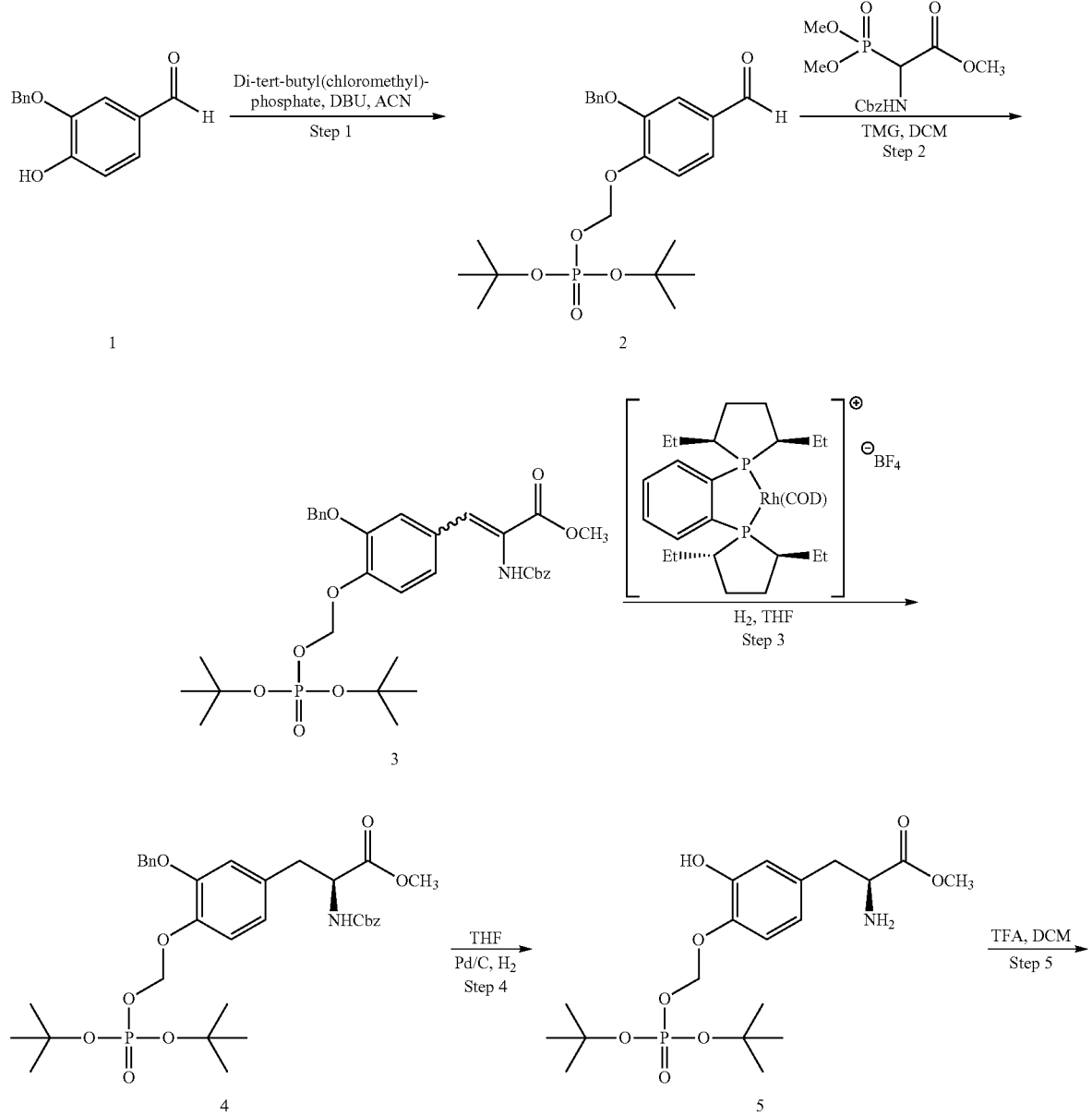

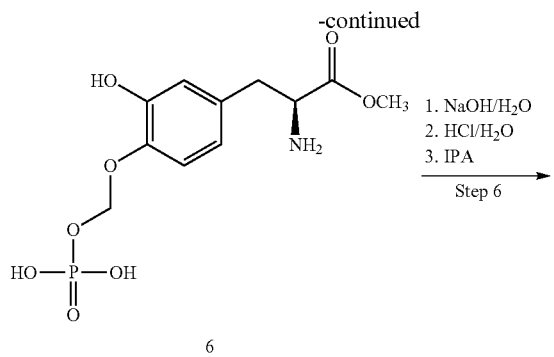 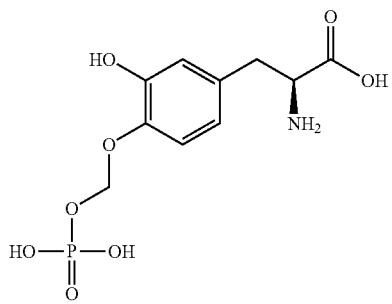

Specifically, L-dopa 4'-phonoxymethyl ester was prepared as described in Steps 1 through 6 below.

Step 1

To a solution of 3-(benzyloxy)-4-hydroxybenzaldehyde, Compound 1, (10.0 g, 43.8 mmol) in acetonitrile (133 ml) was added di-tert-butyl(chloromethyl)phosphate (12.53 g, 46.0 mmol) at 25° C. The reaction mixture was cooled to 4° C. and DBU (7.67 g, 50.4 mmol) was added. After the addition, the reaction mixture was allowed to warm to room temperature (~20-25° C.) and then heated to 50° C. for 22 h. After 22 h the reaction mixture cooled to room temperature and quenched with water (400 ml) and extracted with MTBE (3×100 mL). The organic layer was washed with saturated sodium bicarbonate solution (150 mL), water (150 mL), saturated sodium chloride solution (150 mL), and concentrated to afford Compound 2 (20.0 g, 70% purity, 73% yield). The crude product was passed down a silica gel column using a ethyl acetate-hexane gradient to afford 8.77 g of Compound 2 (91% purity, 41% yield). $^1$H NMR (400 MHz, DMSO-$d_6$) δ 9.87 (s, 1H), 7.59 (d, J=7.0 Hz, 2H), 7.49-7.45 (m, 2H), 7.43-7.31 (m, 4H), 5.72 (d, J=12.7 Hz, 2H), 5.20 (s, 2H), 1.37 (d, J=0.6 Hz, 18H).

Step 2

To a solution of (+/−)-benzyloxycarbonyl-alpha-phosphonoglycine trimethylester (5.51 g, 16.64 mmol) and (2-(benzyloxy)-4-formylphenoxy)methyl di-tert-butyl phosphate, Compound 2, (7.49 g, 15.13 mmol) in 75 mL of DCM at 0° C. was added 1,1,3,3-tetramethylguanidine (2.09 g, 18.16 mmol). The resulting reaction mixture was stirred at room temperature overnight. The next day the reaction mixture was washed with 3×35 mL of water and concentrated to afford 13.11 g of crude product. The crude product was then purified by column chromatography on silica gel using ethyl acetate-hexane gradient to afford 8.37 g of Compound 3 (85% purity, 72% yield). $^1$H NMR (400 MHz, DMSO-$d_6$) δ 7.54 (d, J=2.0 Hz, 1H), 7.50-7.21 (m, 13H), 7.16 (d, J=8.5 Hz, 1H), 5.63 (d, J=12.1 Hz, 2H), 5.09 (d, J=19.1 Hz, 4H), 3.71 (s, 3H), 1.37 (d, J=0.5 Hz, 18H).

Step 3

Into a 120 ml parr reactor was charged methyl 3-(3-(benzyloxy)-4-(((di-tert-butoxyphosphoryl)oxy)methoxy) phenyl)-2-(((benzyloxy)carbonyl)amino)acrylate (8.37 g, 10.85 mmol) and 1,2-bis[(2S,5S)-2,5-diethylphospholano] benzene(1,5-cyclooctadiene) rhodium(I) tetrafluoroborate (0.072 g, 0.109 mmol) and tetrahydrofuran (70.5 ml). The mixture was purged with $H_2$ and the reaction mixture was stirred at 35° C. under 100 psig of $H_2$ for 20 hrs. After 20 hrs, the reaction mixture was concentrated and purified by column chromatography on silica gel using ethyl acetate-hexane gradient to afford 6.34 g of Compound 4 (78% purity, 69% yield, 97% ee). $^1$H NMR (400 MHz, DMSO-$d_6$) δ 7.80 (d, J=8.1 Hz, 1H), 7.54-7.22 (m, 10H), 7.12-6.97 (m, 2H), 6.80 (dd, J=8.2, 2.0 Hz, 1H), 5.54 (d, J=11.3 Hz, 2H), 5.13-4.90 (m, 4H), 4.25 (ddd, J=10.1, 8.1, 5.0 Hz, 1H), 3.62 (s, 3H), 3.04-2.73 (m, 2H), 1.35 (d, J=0.5 Hz, 18H).

Step 4

Into a 50 mL parr reactor was charged 5% Pd/C (JM #9) (0.429 g, 2.372 mmol). The (S)-methyl 3-(3-(benzyloxy)-4-(((di-tert-butoxyphosphoryl)oxy)methoxy)phenyl)-2-(((benzyloxy)carbonyl)amino)propanoate, Compound 4, (2.0 g, 2.372 mmol) was dissolved in tetrahydrofuran (THF) (15.6 ml). This solution was charged into the reactor and purged with argon followed by $H_2$. The reaction mixture was stirred under 50 psig of $H_2$ at room temperature for 1 hour. After 1 h, the catalyst was filtered off and washed with THF. The solution was concentrated and purified by column chromatography on silica gel using ethyl acetate-methanol to afford 1.08 g of Compound 4, (94% purity, 99% yield). $^1$H NMR (400 MHz, DMSO-$d_6$) δ 9.20 (s, 1H), 6.95 (d, J=8.2 Hz, 1H), 6.66 (d, J=2.1 Hz, 1H), 6.54 (dd, J=8.2, 2.1 Hz, 1H), 5.49 (d, J=11.3 Hz, 2H), 3.57 (s, 3H), 3.50 (t, J=6.6 Hz, 1H), 2.79-2.59 (m, 2H), 1.72 (2, 2H), 1.38 (d, J=0.5 Hz, 18H).

Step 5

(S)-methyl 2-amino-3-(4-(((di-tert-butoxyphosphoryl) oxy)methoxy)-3-hydroxyphenyl)propanoate, Compound 5, (1.08 g, 2.34 mmol) in 11 mL of DCM at 5° C. was added 901 uL (5.0 eq) of trifluoroacetic acid dropwise. The rxn mixture was stirred at 25° C. until completed. After 60 mins, the starting material was consumed and the product gummed out of the DCM layer. The product, Compound 6, was extracted from the DCM layer with 3 mL of water. The aqueous layer was then taken, as is, to the next step. LC/MS [M+1]=322.1

Step 6

(S)-methyl 2-amino-3-(3-hydroxy-4-((phosphonooxy) methoxy)phenyl)propanoate, Compound 6, (752 mg, 2.341 mmol) in 3 mL of water at 5° C. was added 6 N NaOH dropwise over 5 min to a pH=12.5. The rxn mixture was stirred at 25° C. until completed. After 60 mins the reaction mixture was acidified with 6N HCL to a pH=1.9. To this solution was added IPA until the product precipitated out while maintaining the pH of 1.9. The product, Compound 7, was filtered and washed with IPA to afford, 850 mg, with a purity of 88%. $^1$H NMR (400 MHz, Deuterium Oxide) δ 7.09 (dd, J=8.2, 0.7 Hz, 1H), 6.76 (d, J=2.1 Hz, 1H), 6.73 (dt, J=8.3, 1.3 Hz, 1H), 5.43 (dd, J=12.6, 0.7 Hz, 2H), 4.08-3.97 (m, 1H), 3.21-2.89 (m, 2H).

Example 10: Synthesis of Carbidopa 3'-Phonoxymethyl Ester and Carbidopa 4'-Phonoxymethyl Ester Carbidopa 3'-phonoxymethyl ester and Carbidopa 4'-phonoxymethyl ester were prepared as shown in Scheme 10 below:

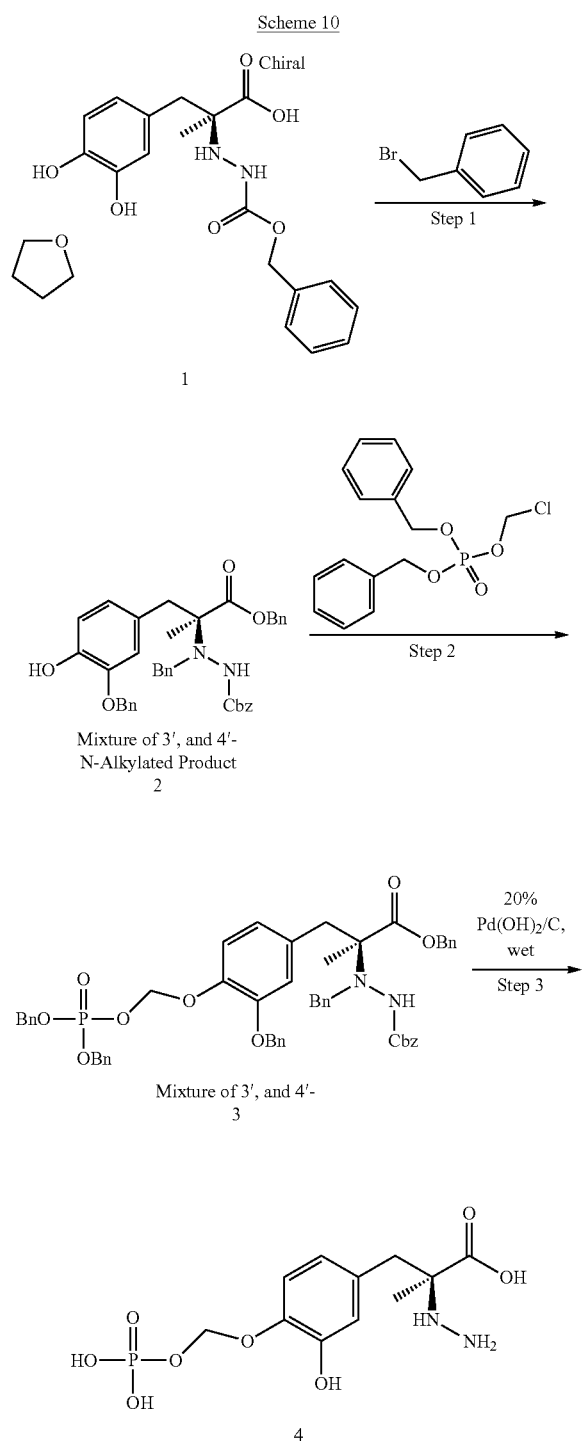

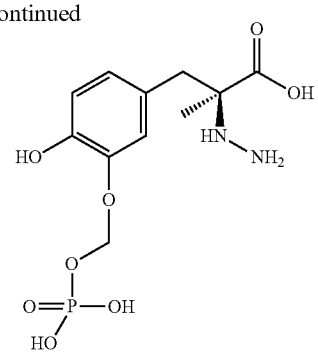

Specifically, Carbidopa 3'-phonoxymethyl ester and Carbidopa 4'-phonoxymethyl ester were prepared as described in Steps 1 through 3 below.

Step 1—Preparation of (S)-benzyl 2-benzyl-2-(1-(benzyloxy)-3-(3-(benzyloxy)-4-hydroxyphenyl)-2-methyl-1-oxopropan-2-yl)hydrazinecarboxylate (a mixture of 3' and 4') (Compound 2)

To a 500 mL round bottom flask were added (S)-2-(2-((benzyloxy)carbonyl)hydrazinyl)-3-(3,4-dihydroxyphenyl)-2-methylpropanoic acid compound with tetrahydrofuran(1:1), Compound 1, (10 g, 84 wt %, 19.42 mmol) and 100 mL DMF. Cesium carbonate (11.39 g, 35 mmol) was added, and the mixture was stirred at room temperature for 15 minutes. The mixture was cooled in an ice bath. Benzyl bromide (7.38 mL, 62.2 mmol) was added portionwise. The mixture was stirred in the ice bath overnight. The slurry was filtered, and the cake was washed with methyl t-butyl ether. The filtrate was mixed with water, and the layers were separated. The aqueous layer was extracted with methyl t-butyl ether. The combined organic layers were washed with brine, dried over anhydrous sodium sulfate, and concentrated. The crude was purified by flash chromatography using a 220 g silica column (0-30% ethyl acetate in heptanes) to afford Compound 2 as a colorless thick oil (1.20 g, 9.8%).

MS (ESI+) 631.1

Step 2-Preparation of (S)-benzyl 2-benzyl-2-(1-(benzyloxy)-3-(3-(benzyloxy)-4-(((bis(benzyloxy)phosphoryl)oxy)methoxy)phenyl)-2-methyl-1-oxopropan-2-yl)hydrazinecarboxylate (a mixture of 3' and 4') (Compound 3)

To a 100 mL round bottom flask were added dibenzyl (chloromethyl) phosphate (1.632 g, 4.99 mmol), (S)-benzyl 2-benzyl-2-(1-(benzyloxy)-3-(3-(benzyloxy)-4-hydroxyphenyl)-2-methyl-1-oxopropan-2-yl)hydrazinecarboxylate, Compound 2, (2.1 g, 3.33 mmol) and 25 mL acetonitrile. The mixture was cooled in an ice bath. 1,8-Diazabicyclo[5.4.0]undec-7-ene (0.745 mL, 4.99 mmol) was added, and the mixture was stirred in the ice bath for 30 minutes, then at room temperature overnight. Water was added to the reaction mixture, and the mixture was extracted with ethyl acetate twice. The combined organic layers were washed with water and brine, dried over anhydrous sodium sulfate, and concentrated. The crude was purified first by flash chromatography using a 120 g silica column (0-50% ethyl acetate in heptanes), followed by RP-HPLC (60-100% acetonitrile in 0.1% TFA/water on Phenonemex C18 5u column) to afford Compound 3 as a colorless oil (247 mg, 8%).

LC/MS (APCI+) m/z=921.2 (M+H)

Step 3—Preparation of (S)-2-hydrazinyl-3-(3-hydroxy-4-((phosphonooxy)methoxy)phenyl)-2-methylpropanoic acid (Compound 4) and (S)-2-hydrazinyl-3-(4-hydroxy-3-((phosphonooxy)methoxy)phenyl)-2-methylpropanoic acid (Compound 5)

(S)-benzyl 2-benzyl-2-(1-(benzyloxy)-3-(3-(benzyloxy)-4-(((bis(benzyloxy)phosphoryl)oxy)methoxy)phenyl)-2-methyl-1-oxopropan-2-yl)hydrazinecarboxylate, Compound 3, (240 mg, 0.261 mmol), 10 mL tetrahydrofuran and 5 mL water were added to 20% Pd(OH)2/C, wet (50 mg, 0.036 mmol) in a 50 ml pressure bottle. The mixture was stirred for 1 hour at 50 psi and room temperature. The reaction mixture was filtered. The filtrate was mixed with water, extracted with methyl t-butyl ether twice. The aqueous phase was dried by a lyophilizer. The concentrate was purified by RP-HPLC (0-10% 0.1% formic acid/acetonitrile in 0.1% formic acid/water on Kromacil Phenyl 3.0 cm ID×25 cm, 5u column). The two isomers were separated. The fractions collected were combined respectively, and dried by a lyophilizer to afford Compound 4 and Compound 5, each as a loose white solid.

Compound 4 (16.5 mg, 16.1%): $^1$H NMR (501 MHz, DMSO-$d_6$) δ 6.94 (d, J=8.1 Hz, 1H), 6.62 (d, J=2.1 Hz, 1H), 6.54 (dd, J=8.1, 2.1 Hz, 1H), 5.28 (d, J=14.6 Hz, 2H), 2.86 (d, J=13.6 Hz, 1H), 2.78 (d, J=13.6 Hz, 1H), 1.26 (s, 3H). MS (ESI+) 337.0

Compound 5 (30.9 mg, 30.2%): $^1$H NMR (400 MHz, DMSO-$d_6$) δ 7.00 (s, 1H), 6.68 (m, 2H), 5.32 (m, 2H), 2.91-2.77 (m, 2H), 1.26 (s, 3H). MS (ESI+) 337.0

Example 11: Synthesis of Carbidopa 4'-Monophosphate Methyl Ester

Carbidopa 4'-monophosphate methyl ester was prepared as shown in Scheme 11 below:

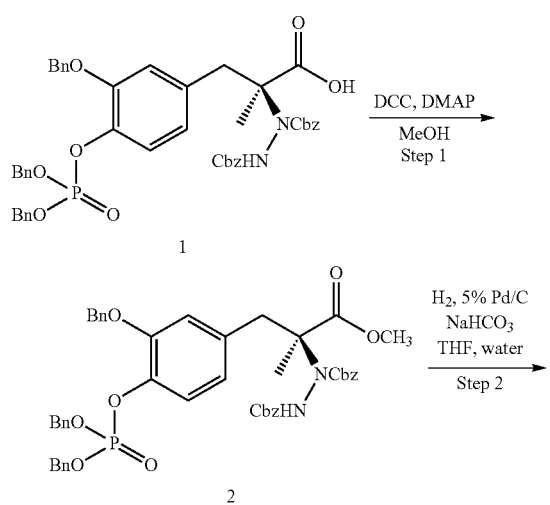

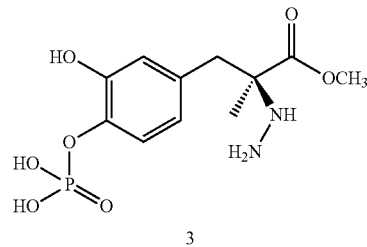

Step 1

A 100 mL round bottom flask was charged with (S)-3-(3-(benzyloxy)-4-((bis(benzyloxy)phosphoryl)oxy)phenyl)-2-(1,2-bis((benzyloxy)carbonyl)hydrazinyl)-2-methylpropanoic acid (3.03 g, 3.59 mmol) (1), DCC (0.889 g, 4.31 mmol), 25 mL of methanol, and a stir bar. To this stirring mixture, 4-(dimethylamino)pyridine (88 mg, 0.720 mmol) was added in one portion and the reaction was stirred for an additional 48 h. After this time, the solvent was removed on a rotary evaporator leaving a light yellow residue. The residue was suspended in acetonitrile (40 mL) and stirred at 5° C. for 2 h. The suspension was then filtered through a silica gel pad, eluting with 400 mL of acetonitrile. Removal of the acetonitrile on a rotary evaporator gave 94% yield of a pale yellow oil, which was used directly in the next step. LC/MS [M+H]: 859.40.

Step 2

A 150-ml Parr reactor was charged with 5% Pd/C (0.794 mg, 3.36 mmol). The catalyst was slurried in water (4.83 ml) and 5 wt % aq sodium bicarbonate (5.61 ml, 3.36 mmol). To this slurry was added a tetrahydrofuran (29 ml) solution of (S)-dibenzyl 1-(3-(3-(benzyloxy)-4-((bis(benzyloxy)phosphoryl)oxy)phenyl)-1-methoxy-2-methyl-1-oxopropan-2-yl)hydrazine-1,2-dicarboxylate (2.89 g, 3.36 mmol) (2). The reactor was sealed and purged with argon (4×40 psig), then H$_2$ (4×50 psig). The reactor was then re-pressurized to 50 psig of H$_2$ and stirred at ambient temperature for 60 min. After this time, the biphasic reaction mixture was filtered through Celite® diatomaceous earth, using water (2.2 mL) to rinse and filter the remnants in the reactor. The biphasic mixture was diluted with MTBE (8 ml), stirred for 5 min, and poured into a separatory funnel. The aqueous layer was separated and washed with DCM (3×30 mL). The aqueous layer was collected and dried on a lyophilizer to give 68% yield of compound 3 as an off-white solid. $^1$H NMR (400 MHz, D$_2$O): δ 1.46 (s, 3H), 2.92 (d, J=12 Hz, 1H), 3.05 (d, J=12 Hz, 1H), 3.79 (s, 3H), 6.65-6.72 (m, 2H), 7.11 (d, J=8.0 Hz, 1H).

Example 12: Phosphate Prodrug Stability Studies

1-Day Stability Studies

The L-dopa phosphate prodrugs and the carbidopa phosphate prodrugs were evaluated in a stability study. Aqueous solutions of the prodrugs (80 μg/mL) were monitored over a range of pH values at ambient storage conditions through one day to demonstrate feasibility of dosing over the course of infusion. Table 12-A below reports the results of this study which confirm that the prodrugs have good stability at room temperature over a one day period.

TABLE 12-A

Stability Study (Prodrugs)

| Compound | pH | % Remaining After One Day |
|---|---|---|
| L-dopa 3'-phosphate | 7.0 | >99% |
| L-dopa 4'-phosphate | 7.0 | >99% |
| L-dopa 3',4'-diphosphate | 7.0 | >99% |
| Carbidopa 3'-phosphate | 6.5 | >94% |
| Carbidopa 4'-phosphate | 6.8 | >98% |
| Carbidopa 3',4'-diphosphate | 6.8 | >97% |

In addition, a solution combining the diphosphates of each compound (L-dopa 3',4'-diphosphate at 35 mg/mL and carbidopa 3',4'-diphosphate at 8.7 mg/mL) was monitored over one day at room temperature. This sample was purged with nitrogen to remove oxygen. Table 12-B below reports the results of this study which confirm good stability for the combination solution at room temperature with nitrogen purging over a one day period.

TABLE 12-B

Stability Study (Diphosphate Combination)

| Compound | pH | % Remaining After One Day |
|---|---|---|
| L-dopa 3',4'-diphosphate | 6.2 | >99% |
| Carbidopa 3',4'-diphosphate |  | >99% |

7-Day Stability Study

In addition, a solution combining the L-dopa 4'-monophosphate at 200 mg/mL and carbidopa 4'-monophosphate at 50 mg/mL was monitored over 7 days at room temperature. These samples were prepared with and without purging with nitrogen to remove oxygen. Table 12-C below reports the results of this study which confirm good stability for the combination solution at room temperature over 7 days.

TABLE 12-C

Stability Study (4' Monophosphate Combination)

| Compound | Purged or Non-pH Purged | % Remaining After 7 Days |
|---|---|---|
| L-dopa 4'-monophosphate | 7.4 Nitrogen Purged | >99% |
| Carbidopa 4'-monophosphate |  | >99% |
| L-dopa 4'-monophosphate | Non-Purged | >99% |
| Carbidopa 4'-monophosphate |  | >97% |

Example 13: Phosphate Prodrug Solubility Studies

The L-dopa phosphate prodrugs and the carbidopa phosphate prodrugs were evaluated in a solubility study. The solubility values of the phosphate prodrugs in water under ambient conditions were determined by visual assessment. Table 13-A reports the results of the study, including the measured values for L-dopa and carbidopa.

TABLE 13-A

Solubility Study

| Compound | pH | Solid State Form | Solubility (mg/mL) |
|---|---|---|---|
| L-dopa | 4-7 | Crystalline | <6 |
| L-dopa 3'-phosphate | 7.0 | Crystalline | >161 |
| L-dopa 4'-phosphate | 7.4 | Crystalline | >400 |

TABLE 13-A-continued

Solubility Study

| Compound | pH | Solid State Form | Solubility (mg/mL) |
|---|---|---|---|
| L-dopa 3',4'-diphosphate | 5.5 | Amorphous | >330 |
| Carbidopa | 4-7 | Crystalline monohydrate | <4 |
| Carbidopa 3'-phosphate | 7.1 | Amorphous | >96 |
| Carbidopa 4'-phosphate | 7.4 | Amorphous | >200 |
| Carbidopa 3',4'-diphosphate | 5.5 | Amorphous | >247 |

FIG. 1 shows increased solubility of L-dopa 4'-monophosphate and carbidopa 4'-monophosphate compared to L-dopa and carbidopa.

Example 14: Hydrazine Release Studies

Figure 2:
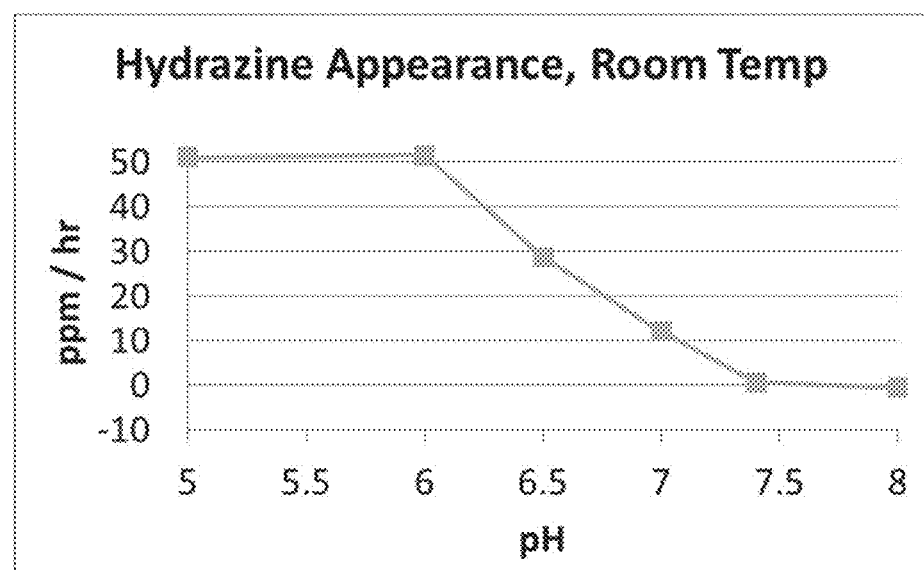
FIG. 2 is a graph of hydrazine release from a solution of L-dopa 4'-monophosphate and carbidopa 4'-phosphate at a ratio of 4:1 at varying pH levels.
Figure 3:
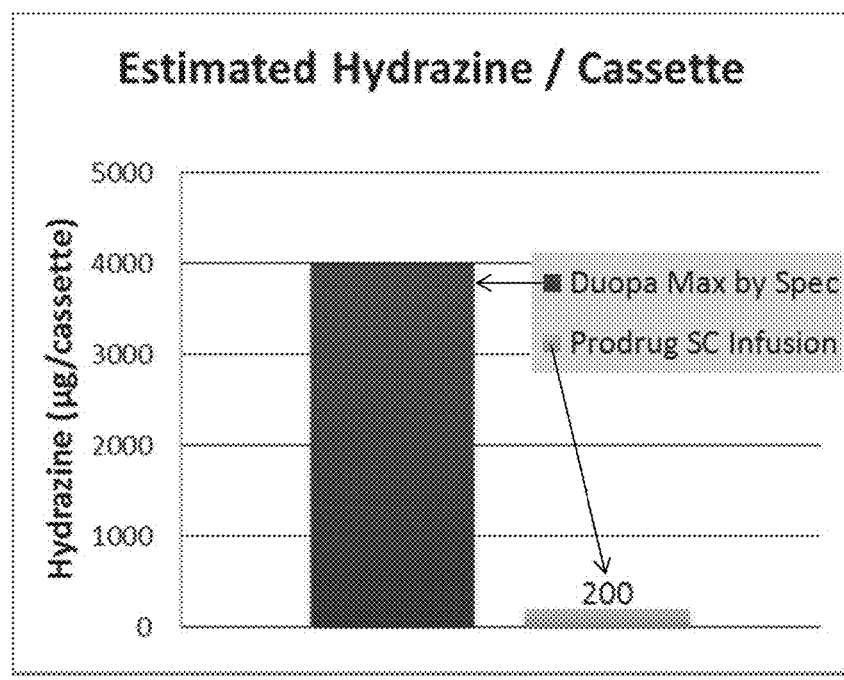
FIG. 3 is a graph comparing hydrazine release between Duopa® and a solution of L-dopa 4'-monophosphate and carbidopa 4'-monophosphate at a ratio of 4:1.

Solutions combining the L-dopa 4'-monophosphate at 50 mg/mL and carbidopa 4'-monophosphate at 12.5 mg/mL were monitored for the release of hydrazine over 7 days. These solutions were prepared from pH 5 to pH 8, were purged with nitrogen to remove oxygen and were held at room temperature. It was found that there was a large reduction in hydrazine release at a pH of about 7.4, as shown in Figure. 2. The amount of hydrazine released from Duopa® was also determined for comparison purposes. As shown in FIG. 3, the 4:1 ratio of a solution L-dopa 4'-monophosphate and carbidopa 4'-monophosphate at a pH of about 7.4 unexpectedly has a much lower release of hydrazine compared to Duopa®.

Example 15: In Vitro Bioconversion Studies

The in vitro bioconversion of the L-dopa phosphate prodrugs to L-dopa and the carbidopa phosphate prodrugs to carbidopa was evaluated in several studies. In brief, the L-dopa and carbidopa phosphate prodrugs (2.5 ug/mL) were incubated with tissue homogenate or fractions from rats, mini-pigs, or human, including blood, skin homogenate (3 mg/mL), liver microsomes (1 mg/mL), liver S9 fraction (1 mg/mL), kidney S9 fraction (1 mg/mL), and intestine S9 fractions (1 mg/mL). The reaction mixtures were incubated at 37° C. for 5 to 6 time points within 1 to 2 hours. At the end of each time point, the reaction mixtures were quenched by 2 to 3 volumes of 5% trichloroacetic acid in water. After quenching, the mixtures were centrifuged at 3000 rpm for 20 minutes, and the supernatants were analyzed by LC-MS for quantitation of the prodrug, L-dopa or carbidopa. The in vitro bioconversion was assessed by monitoring both time-dependent depletion of the prodrug and the formation of the corresponding L-dopa or carbidopa.

Table 15-A below reports the results of the study in blood. In blood, all four mono-phosphate prodrugs were rapidly dephosphorylated in rat, mini-pig, and human, with corresponding time-dependent formation of L-dopa or carbidopa. In general, the $t_{1/2}$ is the shortest in mini-pig, followed by rat, and then human. The diphosphate prodrugs of carbidopa and L-dopa were also rapidly dephosphorylated in rat blood with a $t_{1/2}$ of 53 minutes and 6 minutes, respectively, with corresponding formation of L-dopa or carbidopa. Dephosphorylation of the diphosphate prodrug of L-dopa was slower in human and mini-pig blood with a $t_{1/2}$ of 138 minutes and 125 minutes, respectively. Corresponding time-dependent formation of L-dopa was observed in both mini-pig and human blood incubations. However, the diphosphate prodrug of carbidopa was not dephosphorylated in mini-pig and human blood. No formation of carbidopa was observed in the blood incubations.

TABLE 15-A

In Vitro Bioconversion Study (Blood)

| Prodrug | Species | $T_{1/2}$ (min.) | L-Dopa or Carbidopa Formation |
|---|---|---|---|
| 3'-monophosphate prodrug of L-dopa | Human | 28 | Yes |
|  | Rat | 20.6 | Yes |
|  | Mini-pig | 8.8 | Yes |
| 4'-monophosphate prodrug of L-dopa | Human | 30.9 | Yes |
|  | Rat | 15 | Yes |
|  | Mini-pig | 8.8 | Yes |
| 3',4'-disphosphate prodrug of L-dopa | Human | 138 | Yes |
|  | Rat | 6 | Yes |
|  | Mini-pig | 125 | Yes |
| 3'-monophosphate prodrug of carbidopa | Human | 58 | Yes |
|  | Rat | 20.5 | Yes |
|  | Mini-pig | 8.9 | Yes |
| 4'-monophosphate prodrug of carbidopa | Human | 64.7 | Yes |
|  | Rat | 14.9 | Yes |
|  | Mini-pig | 8.8 | Yes |
| 3',4'-diphosphate prodrug of carbidopa | Human | stable | No |
|  | Rat | 53 | Yes |
|  | Mini-pig | stable | No |

Table 15-B below reports the results of the study in skin homogenates. In skin homogenates, the four mono-phosphate prodrugs were slowly dephosphorylated with a t½ ranging from 114 minutes to 992 minutes, with corresponding formation of L-dopa or carbidopa. The two diphosphate prodrugs were stable in skin homogenates of rat, mini-pig, and human. No formation of L-dopa or carbidopa was observed in the incubations.

TABLE 15-B

In Vitro Bioconversion Study (Skin Homogenates)

| Prodrug | Species | $T_{1/2}$ (min.) | L-Dopa or Carbidopa Formation |
|---|---|---|---|
| 3'-monophosphate prodrug of L-dopa | Human | 673 | Yes |
|  | Rat | 737 | Yes |
|  | Mini-pig | 885 | Yes |
| 4'-monophosphate prodrug of L-dopa | Human | 592 | Yes |
|  | Rat | 992 | Yes |
|  | Mini-pig | 424 | Yes |
| 3',4'-disphosphate prodrug of L-dopa | Human | stable | No |
|  | Rat | stable | No |
|  | Mini-pig | stable | No |
| 3'-monophosphate prodrug of carbidopa | Human | 602 | Yes |
|  | Rat | 724 | Yes |
|  | Mini-pig | 413 | Yes |
| 4'-monophosphate prodrug of carbidopa | Human | 138 | Yes |
|  | Rat | 271 | Yes |
|  | Mini-pig | 114 | Yes |
| 3',4'-diphosphate prodrug of carbidopa | Human | stable | No |
|  | Rat | stable | No |
|  | Mini-pig | stable | No |

In human liver microsomes, four prodrugs (3'-phosphate and diphosphate prodrugs of L-dopa, and 4'-phosphate and diphosphate prodrugs of carbidopa) were stable without formation of L-dopa or carbidopa observed.

In liver S9 fractions of rat, mini-pig and human, four prodrugs (4'-phosphate and diphosphate prodrugs of L-dopa, and 4'-phosphate and diphosphate prodrugs of carbidopa) were stable without formation of L-dopa or carbidopa observed.

In kidney S9 fractions of rat and human, four prodrugs (4'-phosphate and diphosphate prodrugs of L-dopa, and 4'-phosphate and diphosphate prodrugs of carbidopa) were stable without formation of L-dopa or carbidopa observed.

Table 14-C below reports the results of the study in intestinal S9 fractions. In intestinal S9 fractions of rat and human, four prodrugs (4'-phosphate and diphosphate prodrugs of L-dopa, and 4'-phosphate and diphosphate prodrugs of carbidopa) were rapidly dephosphorylated. The $t_{1/2}$ appeared to be shorter in human intestinal S9 than in rat intestinal S9. Corresponding time-dependent formation of L-dopa or carbidopa was observed in the incubations of prodrugs with rat or human intestinal S9 fractions. The results suggest significant phosphatase activities in rat and human intestine.

TABLE 15-C

In Vitro Bioconversion Study (Intestinal S9 Fractions)

| Prodrug | Species | $T_{1/2}$ (min.) | L-Dopa or Carbidopa Formation |
|---|---|---|---|
| 4'-monophosphate prodrug of L-dopa | Human | 34.3 | Yes |
|  | Rat | 158 | Yes |
| 3',4'-disphosphate prodrug of L-dopa | Human | 92 | Yes |
|  | Rat | 54.2 | Yes |
| 4'-monophosphate prodrug of carbidopa | Human | 24.1 | Yes |
|  | Rat | 73.6 | Yes |
| 3',4'-diphosphate prodrug of carbidopa | Human | 31.5 | Yes |
|  | Rat | 79 | Yes |

Example 16: Pharmacokinetic Studies in Rats

The in vivo conversion of the L-dopa phosphate prodrugs to L-dopa and the carbidopa phosphate prodrugs to carbidopa was evaluated in a rat pharmacokinetics study in which the prodrug was administered intravenously or subcutaneously to the rat. For comparison, a rat pharmacokinetics study with L-dopa and carbidopa was conducted to help assess the in vivo conversion of the prodrugs. The study design and measured exposures of L-dopa and carbidopa are summarized in Tables 16-A and 16-B, respectively. In brief, groups of three male Sprague-Dawley rats were given (1) L-dopa and carbidopa in aqueous solution, or (2) the individual prodrug in aqueous solution intravenously or subcutaneously. Blood samples were collected at multiple time points over 24 hours into a collection tube containing $NaAsO_4$, EDTA, and ascorbic acid. Plasma was separated from blood and subjected to protein precipitation with 2 to 3 volumes of 5% trichloroacetic acid in water, followed by centrifugation. The supernatants were subjected to LC-MS analysis for quantitation of prodrug, L-dopa or carbidopa.

TABLE 16-A

In Vivo Exposures in Rats (L-Dopa)

| Dosed Compound | Dosing Route | Dose (mg/kg) | L-dopa $AUC_{0\text{-}8\,h}$ (ng · hr/mL) | Estimated Conversion % (Based on L-dopa AUC) |
|---|---|---|---|---|
| 3'-monophosphate prodrug of L-dopa | SC | 7.05 | 645 | 96 |
|  | IV | 7.05 | 768 | 66 |
| 4'-monophosphate prodrug of L-dopa | SC | 7.05 | 1280 | >100 |
|  | IV | 7.05 | 1540 | >100 |
| 3',4'-diphosphate prodrug of L-dopa | SC | 8.5 | 1480 | >100 |
|  | IV | 8.5 | 1700 | >100 |

TABLE 16-A-continued

In Vivo Exposures in Rats (L-Dopa)

| Dosed Compound | Dosing Route | Dose (mg/kg) | L-dopa $AUC_{O-8\,h}$ (ng · hr/mL) | Estimated Conversion % (Based on L-dopa AUC) |
|---|---|---|---|---|
| L-dopa | SC | 5 | 669 | — |
|  | IV | 5 | 1170 | — |

TABLE 16-B

In Vivo Exposures in Rats (Carbidopa)

| Dosed Compound | Dosing Route | Dose (mg/kg) | Carbidopa $AUC_{O-8\,h}$ (ng · hr/mL) | Estimated Conversion % (Based on Carbidopa AUC) |
|---|---|---|---|---|
| 3'-monophosphate prodrug of carbidopa | SC | 1.7 | 605 | 88 |
|  | IV | 1.7 | 861 | 100 |
| 4'-monophosphate prodrug of carbidopa | SC | 1.7 | 863 | >100 |
|  | IV | 1.7 | 757 | 88 |
| 3',4'-diphosphate prodrug of carbidopa | SC | 2.1 | 615 | 90 |
|  | IV | 2.1 | 808 | 94 |
| Carbidopa | SC | 1.25 | 685 | — |
|  | IV | 1.25 | 860 | — |

By comparison of the in vivo exposures of L-dopa or carbidopa obtained from administration of the prodrugs to those obtained from administration of L-dopa or carbidopa alone, in vivo conversions of the prodrugs to the corresponding L-dopa or carbidopa were estimated to be greater than 66%.

Example 17: L-Dopa Diphosphate/Carbidopa Diphosphate Ratio Study

The effect of various dose ratios of the carbidopa diphosphate to the L-dopa diphosphate on steady state levels of L-dopa was evaluated in a rat pharmacokinetics study. In the study, the rats received a 16-hour subcutaneous infusion of a combination of L-dopa diphosphate (fixed dose) and carbidopa diphosphate (various doses) together in an aqueous solution. In brief, groups of three male Sprague-Dawley rats were given a combination of L-dopa diphosphate and carbidopa diphosphate with different dose ratios. Table 17-A provides a summary of the study design. Rats were initially given subcutaneous bolus doses over one minute at the dose volume of 1 mL/kg. After 1.5 hours, continuous infusion doses were administrated over the following 14.5 hours at the dose volume of 10 mL/kg. Blood samples were collected at 0.25, 0.5, 1, 6, 16 and 20 hours post bolus dose. The blood samples were processed in the same way as described in Example 16. Separate aliquots of blood samples were collected for measurement of hydrazine.

TABLE 17-A

Study Design of Prodrug Ratio Study in Rats

| Dose Group | Subcutaneous Bolus Dose (mg/Kg) over 1 min | | Subcutaneous Infusion Dose (mg/kg) over 14.5 h | |
|---|---|---|---|---|
|  | L-Dopa Diphosphate Prodrug | Carbidopa Diphosphate Prodrug | L-Dopa Diphosphate Prodrug | Carbidopa Diphosphate Prodrug |
| LD alone | 15 | 0 | 75 | 0 |
| LD 50:1 | 15 | 0.3 | 75 | 1.5 |
| LD 15:1 | 15 | 1 | 75 | 5 |
| LD 7.5:1 | 15 | 2 | 75 | 10 |
| LD 4:1 | 15 | 3.75 | 75 | 18.75 |
| LD 1:1 | 15 | 15 | 75 | 75 |

Figure 4:
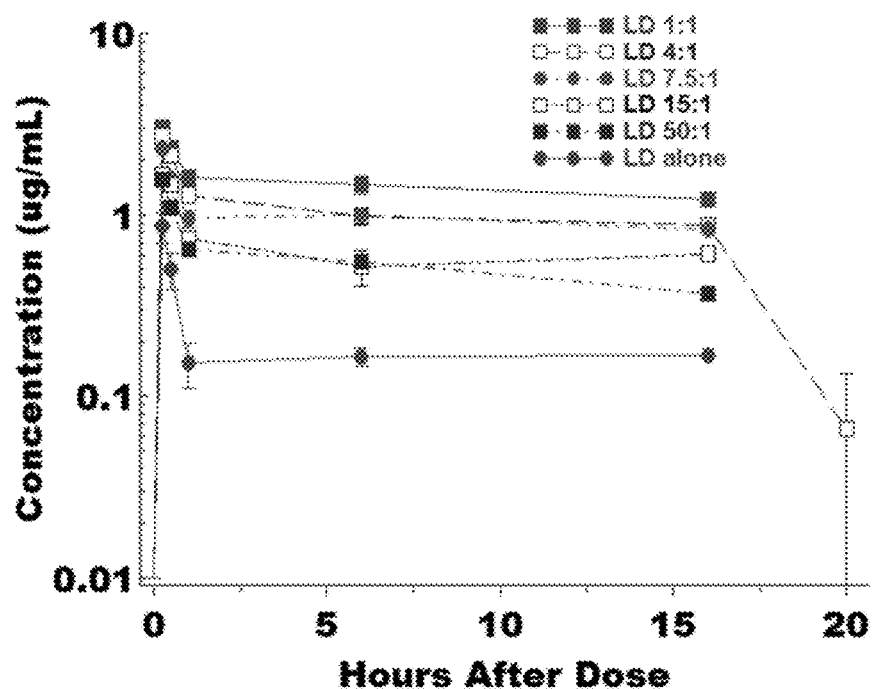
FIG. 4 is a time-concentration profile of L-dopa blood levels in rats after administration of a combination of L-dopa 3',4'-diphosphate and carbidopa 3',4'-diphosphate at different dose ratios.
Figure 5:
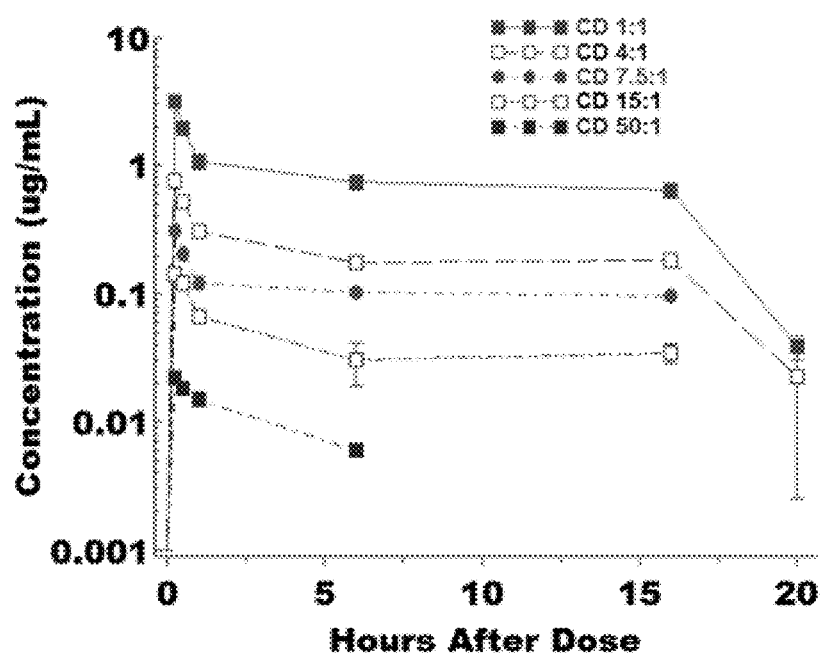
FIG. 5 is a time-concentration profile of carbidopa blood levels in rats after administration of a combination of L-dopa 3',4'-diphosphate and carbidopa 3',4'-diphosphate at different dose ratios

Both L-dopa and carbidopa levels were well maintained during the continuous infusion period between 1 hour and 16 hours in each dose group. FIG. 4 provides a time-concentration profile for L-dopa blood levels after administration of the combination of diphosphate prodrugs at different ratios. FIG. 5 provides a time-concentration profile for carbidopa blood levels after administration of the combination of diphosphate prodrugs at different ratios.

Figure 6:
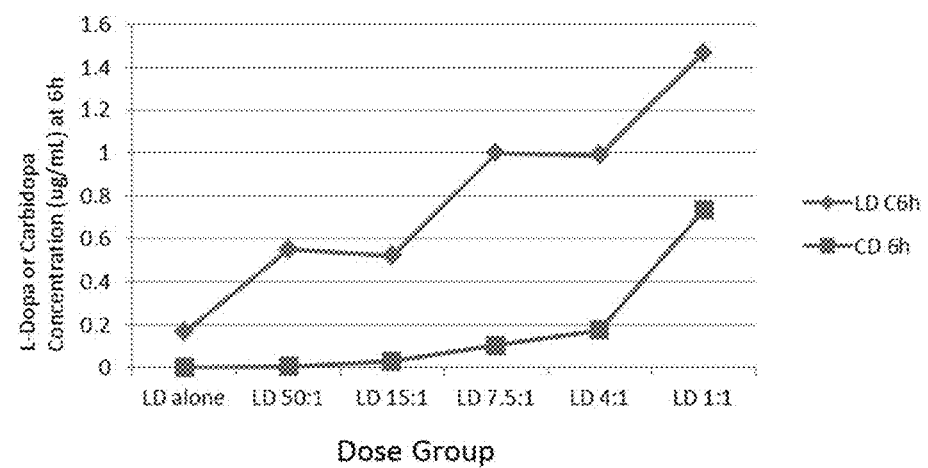
FIG. 6 is a graph of the steady-state blood levels of L-dopa and carbidopa in rats after administration of a combination of L-dopa 3',4'-diphosphate and carbidopa 3',4'-diphosphate at different dose ratios.

Table 17-B below reports the measured steady-state blood levels of L-dopa ("LD") and carbidopa ("CD"). FIG. 6 presents the same data graphically. The ratio of the L-dopa diphosphate to the carbidopa phosphate had a significant effect on the steady state level of L-dopa. For example, after administration of the L-dopa diphosphate alone, mean plasma concentration of L-dopa at 6 hours ($C_{6h}$) was 0.164 µg/mL. When a combination of L-dopa diphosphate and carbidopa diphosphate was administered at the dose ratio of 50:1, mean plasma concentration of L-dopa at 6 hours ($C_{6h}$) increased to 0.55 µg/mL. When a combination of L-dopa diphosphate and carbidopa diphosphate was administered at the dose ratio of 1:1, mean plasma concentration of L-dopa at 6 hours ($C_{6h}$) further increased to 1.47 µg/mL. In all groups, hydrazine levels were below the limit of quantitation (0.5 ng/mL).

TABLE 17-B

Steady-State Levels of L-Dopa and Carbidopa (Different Prodrug Ratios)

| Group | LD concentration at 6 h (µg/mL) | CD concentration at 6 h (µg/mL) |
|---|---|---|
| LD alone | 0.164 | 0 |
| LD 50:1 | 0.55 | 0.006 |
| LD 15:1 | 0.52 | 0.03 |
| LD 7.5:1 | 1 | 0.103 |
| LD 4:1 | 0.99 | 0.175 |
| LD 1:1 | 1.47 | 0.734 |

Example 18: L-Dopa 4'-Monophosphate/Carbidopa 4'-Monophosphate Pharmacokinetic Studies in Rats The effect of a 4:1 ratio of L-dopa 4'-monophosphate to carbidopa 4'-phosphate on steady state levels of L-dopa was evaluated in a rat pharmacokinetics study.

16-Hour Subcutaneous Infusion

Figure 7:
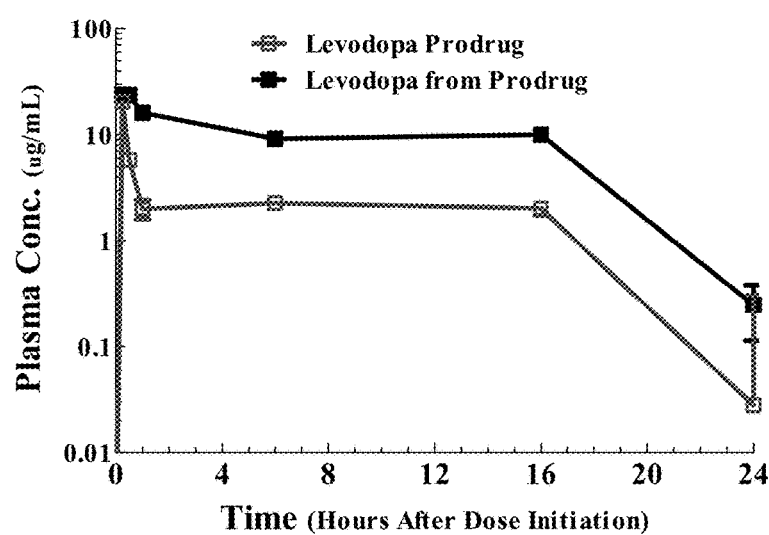
FIG. 7 is a time-concentration profile of L-dopa blood levels and L-dopa 4'-monophosphate blood levels in rats after administration of a combination of L-dopa 4'-monophosphate and carbidopa 4'-monophosphate at a ratio of 4:1.
Figure 8:
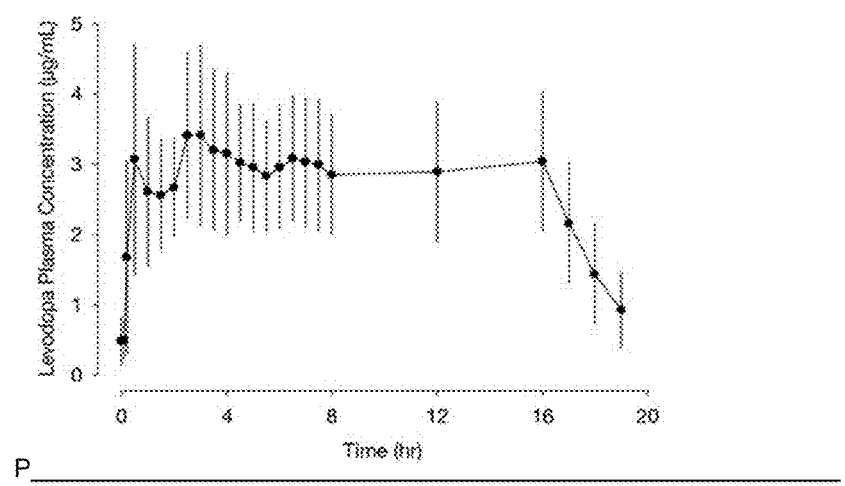
FIG. 8 is a time-concentration profile (mean±standard deviation) of L-dopa blood levels in humans after 16-hour infusion administration of Duopa® (levodopa, 1580±403 mg; carbidopa, 366±92 mg).
Figure 9:
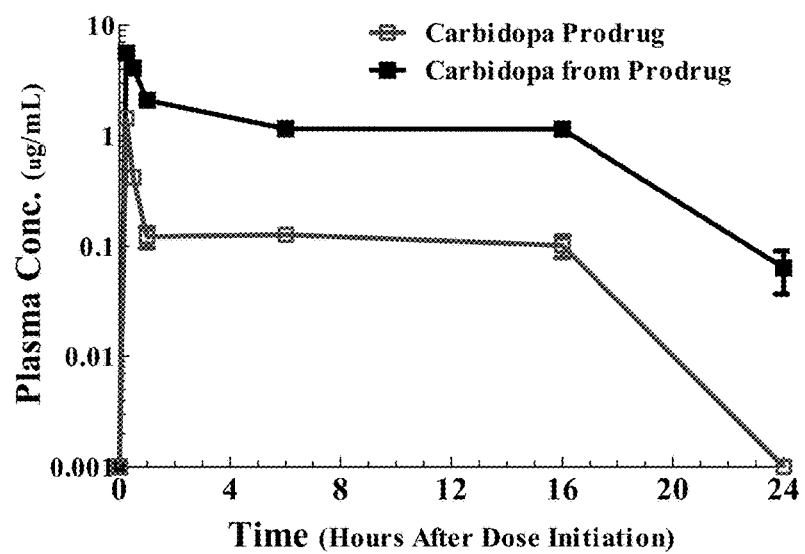
FIG. 9 is a time-concentration profile of carbidopa blood levels and carbidopa 4'-monophosphate blood levels in rats after administration of a combination of L-dopa 4'-monophosphate and carbidopa 4'-monophosphate at a ratio of 4:1.

In this study, a combination L-dopa 4'-monophosphate and the carbidopa 4'-monophosphate together in an aqueous solution at a dose ratio of 4:1 was initially administrated to the rats via subcutaneous bolus at the dose of 60/14 mg/kg over 1 min. After 1.5 hours, the combination was dosed again via continuous infusion at a dose of 300/71 mg/kg over next 14.5 hours. Blood samples were collected at 0, 0.25, 1, 6, 16, and 24 hours post dose. The blood samples were processed in the same way as described in Example 15. Separate aliquots of blood samples were collected for measurement of hydrazine. FIG. 7 provides a time-concentration profile for L-dopa and L-dopa 4'-monophosphate blood levels after administration of the combination of 4'-monophosphate prodrugs at a 4:1 ratio. As shown in FIG. 7, continuous subcutaneous infusion of 4:1 L-dopa 4'-monophosphate and carbidopa 4'-monophosphate delivered high systematic levels of L-dopa (e.g., ~10 μg/mL), which meets and/or exceeds the plasma levels (e.g., ~3 μg/mL) achieved with Duopa®, as shown in FIG. 8. Steady state concentration of ~1 μg/mL was maintained over the infusion period for carbidopa. Exposures of the remaining L-dopa 4'-monophosphate and carbidopa 4'-monophosphate were ~22% and ~8% of levodopa and carbidopa, respectively. The doses were well tolerated in rats, and no hydrazine was detected in rat plasma samples. FIG. 9 provides a time-concentration profile for carbidopa and carbidopa 4'-monophosphate blood levels after administration of the combination of 4'-monophosphate prodrugs at a 4:1 ratio.

7-Day 24-Hour Subcutaneous Infusion

In this study, the rat received a 24-hour subcutaneous infusion of a combination of the L-dopa (LD) 4'-monophosphate and the carbidopa (CD) 4'-monophosphate together in an aqueous solution at a dose ratio of 4:1 for 7 days. Table 18-A below reports the measured steady-state concentration of levodopa at various amounts of L-dopa 4'-monophosphate and carbidopa 4'-monophosphate in a 4:1 ratio.

TABLE 18-A

Steady-State Concentration Levels of L-Dopa

| Prodrug Dose LD-4'-Phosphate/CD-4'-phosphate (mg/kg) | L-Dopa Css (μg/mL) |
|---|---|
| 100/25 | 2.18 ± 0.3 |
| 300/75 | 9.36 ± 1.9 |
| 750/187.5 | 35.2 ± 13.5 |

Example 19: L-Dopa Diphosphate and Carbidopa Diphosphate Pharmacokinetic Studies in Mini-Pigs The in vivo conversion of the carbidopa diphosphate to carbidopa was evaluated in a mini-pig pharmacokinetics study in which the prodrug was administered in aqueous solution subcutaneously to a group of three mini-pigs. For comparison, a pharmacokinetics study with carbidopa also was conducted to help assess the in vivo conversion of the carbidopa prodrugs. Table 19-A reports the measured carbidopa exposures. The estimated in vivo conversion of the carbidopa diphosphate to carbidopa was approximately 100%, based on the carbidopa exposures.

TABLE 19-A

In Vivo Carbidopa Exposures in Mini-Pig

| Dosed Compound | Dosing Route | Dose (mg/kg) | Carbidopa $AUC_{O\text{-}8\,h}$ (ng · hr/mL) | Estimated Conversion % (Based on Carbidopa AUC) |
|---|---|---|---|---|
| 3',4'-diphosphate prodrug of carbidopa | SC | 8.5 | 6870 | 100 |
| Carbidopa | SC | 2 | 1610 | — |

The effect of various dose ratios of the carbidopa diphosphate to the L-dopa diphosphate on steady state levels of L-dopa was evaluated in a mini-pig pharmacokinetics study. In the study, the mini-pig received a 16-hour subcutaneous infusion of a combination of the L-dopa diphosphate and the carbidopa diphosphate together in an aqueous solution at a specified dose ratio. A wash-out period followed each dose ratio. The study design is summarized in Table 19-B below and was similar to the design of the previously described rat study except that there were no initial subcutaneous bolus doses. Blood samples were collected at 1, 2, 4, 6, 8, 10, 14, 16, and 24 hours post dose. The blood samples were processed in the same way as described in Example 12. Separate aliquots of blood samples were collected for measurement of dopamine.

TABLE 19-B

Study Design of Prodrug Ratio Study in Mini-Pigs

| Dose Group | Subcutaneous Infusion Dose (mg/kg) over 16 h | |
|---|---|---|
| | L-Dopa Diphosphate Prodrug | Carbidopa Diphosphate Prodrug |
| LD alone | 45.9 | 0 |
| LD 15:1 | 45.9 | 3.06 |
| LD 7.5:1 | 45.9 | 6.12 |
| LD 4:1 | 45.9 | 11.5 |

Figure 10:
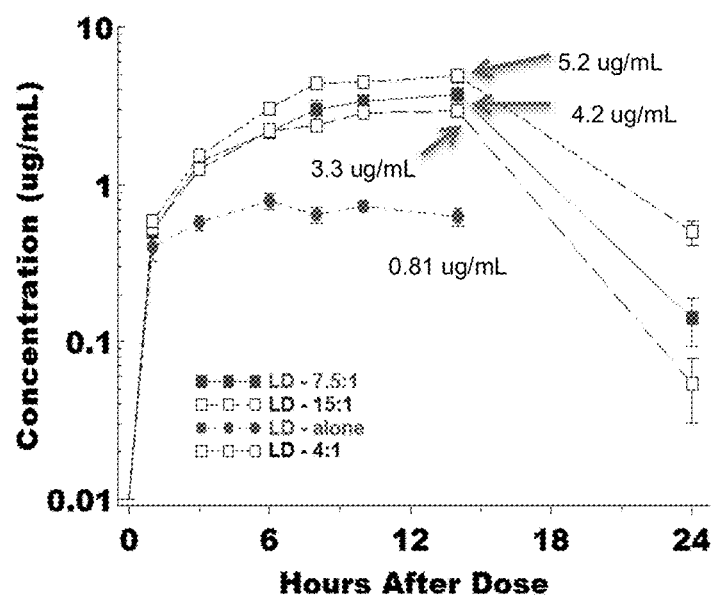
FIG. 10 is a time-concentration profile of L-dopa blood levels in mini-pigs after administration of a combination of L-dopa 3',4'-diphosphate and carbidopa 3',4'-diphosphate at different dose ratios.

FIG. 10 provides a time-concentration profile for L-dopa blood levels after administration of the combination of diphosphate prodrugs at different ratios. No dopamine was detected in the mini-pigs blood plasma samples.

Example 20: 15:1 L-Dopa 4'-Monophosphate/Carbidopa 4'-Monophosphate Pharmacokinetic Studies in Mini-Pigs The effect of a 15:1 ratio of L-dopa 4'-monophosphate to carbidopa 4'-phosphate on steady state levels of L-dopa was evaluated in a mini-pig pharmacokinetics study.

In this study, the pig received a 16-hour subcutaneous infusion of a combination of the L-dopa 4'-monophosphate and the carbidopa 4'-monophosphate together in an aqueous solution at a dose ratio of 15:1 without an initial bolus dose. The doses were 48/3.2 mg/kg for L-dopa 4'-monophosphate and the carbidopa 4'-monophosphate, respectively. Blood samples were collected at 1, 3, 6, 8, 10, 14, and 24 hours post dose. The blood samples were processed in the same way as described in Example 12. Separate aliquots of blood samples were collected for measurement of hydrazine. Table 20-A provides a summary of measured exposures of L-dopa 4'-monophosphate and L-dopa in the mini-pigs.

TABLE 20-A

| Minipig # | L-dopa Prodrug | | | Levodopa | | |
|---|---|---|---|---|---|---|
| | $C_{max}$ | $T_{max}$ | $AUC_{0-t}$ | $C_{max}$ | $T_{max}$ | $AUC_{0-t}$ |
| 1 | 814 | 3.0 | 7110 | 4320 | 14 | 63000 |
| 2 | 681 | 3.0 | 6450 | 6030 | 10 | 84300 |
| 3 | 689 | 6.0 | 6670 | 6180 | 14 | 85400 |
| Mean | 728 | 4.0 | 6740 | 5510 | 13 | 77600 |
| SEM | 43.1 | 1.0 | 194 | 597 | 1.3 | 7270 |

Figure 11:
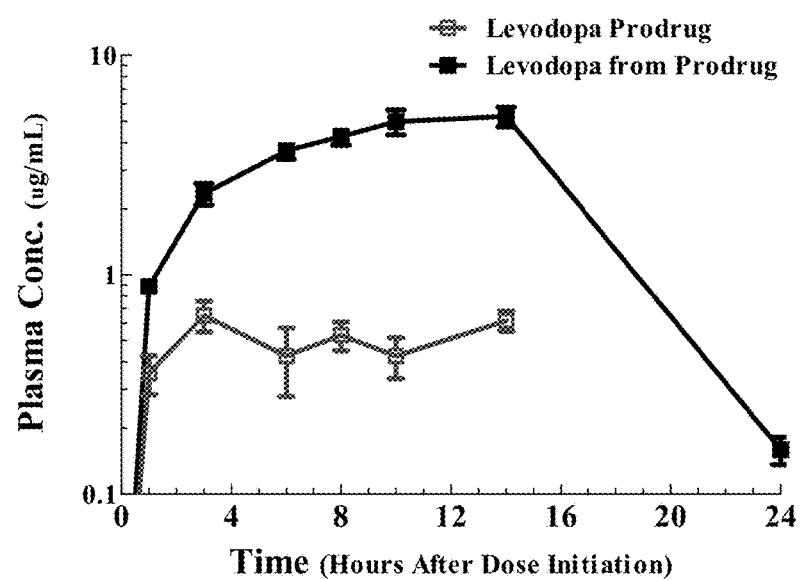
FIG. 11 is a time-concentration profile of L-dopa blood levels and L-dopa 4'-monophosphate blood levels in mini-pigs after administration of a combination of L-dopa 4'-monophosphate and carbidopa 4'-monophosphate at a ratio of 15:1.
Figure 12:
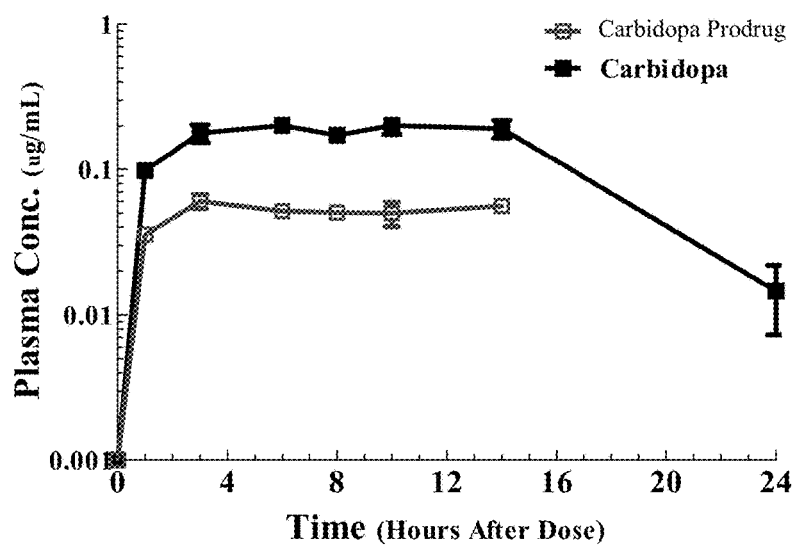
FIG. 12 is a time-concentration profile of carbidopa blood levels and carbidopa 4'-monophosphate blood levels in mini-pigs after administration of a combination of L-dopa 4'-monophosphate and carbidopa 4'-monophosphate at a ratio of 15:1

$C_{max}$ [ng/mL];
$T_{max}$ [hr];
$AUC_{0-t}$ [ng*hr/mL];

FIG. 11 provides a time-concentration profile for L-dopa and L-dopa 4'-monophosphate blood levels after administration of the combination of 4'-monophosphate prodrugs at a 15:1 ratio. As shown in FIG. 11, continuous subcutaneous infusion of 15:1 L-dopa 4'-monophosphate and carbidopa 4'-phosphate delivered high systematic levels of L-dopa (e.g., ~5.5 µg/mL), which meets and/or exceeds the plasma levels (e.g., ~3 µg/mL) achieved with Duopa®, as shown in FIG. 8. Plasma concentration of levodopa increased over time and was close to steady state at ~10 hours post dose. Steady-state levodopa plasma concentration was achieved at ~5.5 µg/mL. Exposure of the remaining the L-dopa 4'-monophosphate was ~10% of the levodopa exposure. Carbidopa plasma concentration reached steady-state at ~3 hours post dose with a steady-state concentration of ~0.2 µg/mL. Exposure of the remaining the carbidopa 4'-monophosphate was ~22% of the carbidopa exposure. The doses were well tolerated in mini-pigs, and no hydrazine was detected in mini-pig plasma samples. FIG. 12 provides a time-concentration profile for carbidopa and carbidopa 4'-monophosphate blood levels after administration of the combination of 4'-monophosphate prodrugs at a 15:1 ratio.

Example 21: L-Dopa 4'-Monophosphate and Carbidopa 4'-Monophosphate Pharmacokinetic Studies in Dogs In this study, the dog received a 24-hour subcutaneous infusion of a combination of the L-dopa (LD) 4'-monophosphate and the carbidopa (CD) 4'-monophosphate together in an aqueous solution at a dose ratio of 4:1. Table 21-A below reports the measured steady-state concentration of levodopa (L-dopa) at various amounts of the L-dopa 4'-monophosphate and carbidopa 4'-monophosphate in a 4:1 ratio. There was no mortality and all dogs survived to the end of the study. The (LD) 4'-monophosphate and the carbidopa (CD) 4'-monophosphate drugs were well tolerated. Test item related clinical signs in the 400/100 mg/kg consisted of emesis in both dogs, which occurred early during the dosing interval. Clinical pathology findings in the Levodopa and Carbidopa 4'-monophosphate prodrugs consisted of mildly increased neutrophil and monocyte counts at 400/100 mg/kg; mildly decreased triglycerides for animals administered ≥200/50 mg/kg; mildly increased bilirubin for animals administered ≥200/50 mg/kg; increased urine specific gravity at all doses; minimally increased urine phosphorus to creatinine ratio and fractional excretion of phosphorus at 400/100 mg/kg. Conclusions: Administration of L-dopa (LD) 4'-monophosphate and the carbidopa (CD) 4'-monophosphate at doses of up to 400/100 mg/kg resulted in no adverse findings. This resulted in a Levodopa concentration of 18.3 µg/mL and a Carbidopa concentration of 2.88 µg/mL.

TABLE 21-A

| Steady-State Concentration Levels of L-Dopa | | |
|---|---|---|
| Prodrug Dose LD-4'-monophosphate/CD-4'-monophosphate (mg/kg) | L-Dopa Css (µg/mL) | Carbidopa Css (µg/mL) |
| 100/25 | 2.13 | 0.673 |
| 200/50 | 5.08 | 1.47 |
| 400/100 | 18.3 | 2.88 |

Example 22: Phosphorus Load

When rats were administered L-dopa diphosphate/carbidopa diphosphate prodrug composition (i.e., diphosphate composition), there was an increase in serum phosphate at doses ≥300/75 mg/kg/day. This elevation in serum phosphate did not occur in rats administered L-dopa 4'-monophosphate/carbidopa 4'-monophosphate composition (i.e., monophosphate composition) at doses of up to 750/187.5 mg/kg/day.

Example 23: Safety and Tolerability

Local irritation and pain at the injection site were studied.
Local Tolerability:
Pain on injection was evaluated in rabbits using intravenous, paravenous, and subcutaneous bolus injection of LD/CD diphosphate at concentrations for 200/50 mg/mL. Immediately upon injection and through 24 hours of observation there was no indication of injection site pain or local tissue irritation. There were no adverse clinical signs or microscopic findings indicative of local intolerance in rats administered a single SC bolus dose of LD diphosphate at concentrations up to 125 mg/mL or in minipigs subcutaneously infused LD/CD diphosphate for 24 hours at 200/50 mg/mL.

In the 7-day SC infusion studies in rats there was no indication of infusion site irritation or intolerability for either the LD/CD diphosphates or the LD/CD monophosphates when infused at 41/10 and 75/18.75 mg/mL, respectively for 18 or 24 hours/day, respectively. When LD/CD monophosphate (200/50 mg/mL) was subcutaneously infused to dogs for 24 hours there was no apparent visual irritation at the injection site. The cumulative data is supportive of a low risk for pain on injection or local tissue irritation, when infused at the same site for 24 hours.
Rodent Toxicity:
A 7-day IV infusion toxicity study was conducted with L-Dopa and carbidopa diphosphate prodrugs together in an aqueous solution. Sprague-Dawley rats (n=5/sex/group) were administered dosages of 80/20, 240/60 or 720/180 mg/kg for 18 hours per day over 7 consecutive days. Although rats in the 720/180 mg/kg group exhibited an increase in serum phosphorus, other than body weight loss and reductions in food consumption there were no adverse clinical signs, clinical pathology or histopathology findings observed. The L-Dopa disphosphate and carbidopa diphosphate prodrugs dose of 720/180 mg/kg resulted in a levodopa plasma concentration of 15.2 µg/mL.

A 7-day SC infusion toxicity study was also conducted with L-Dopa and carbidopa diphosphate prodrugs together in an aqueous solution. Sprague-Dawley rats (n=5/sex/group) were administered dosages of 100/25, 300/75 or 750/187.5 mg/kg for 18 hours per day over 7 consecutive days. Although male rats in the 300/75 and male and female rats in the 750/187.5 mg/kg groups exhibited an increase in serum phosphorus, with exception of body weight loss and reductions in food intake there were no adverse clinical signs, clinical pathology or histopathology findings observed. The dose of 750/187.5 mg/kg resulted in a levodopa plasma concentration of 19.6 µg/mL.

A 7-day SC infusion toxicity study was also conducted with L-Dopa and carbidopa mixed monophosphate together in an aqueous solution. Male Sprague-Dawley rats (n=4 or 5/group) were administered dosages of 100/25, 300/75 or 750/187.5 mg/kg for 24 hours per day over 7 consecutive days. Rats in the 750/187.5 mg/kg group exhibited clinical signs that included aggressive behavior and increased activity. The findings were sufficiently pronounced that they impacted the SC catheter placement and patency and that some animals were removed from study prior to completing the full dose schedule. Mean body weights at the end of the study in the 300/75 mg/kg groups were decreased by 18% relative to the start of dosing on day 1. There were no significant effects on serum or urinary phosphate and there were no adverse clinical pathology or histopathology findings. The levodopa plasma concentration was 9.4 µg/mL in the 300/75 mg/kg group.

TABLE 24-A

Projected human PK parameters for monophosphate prodrugs and active drugs

| | CLp (l/hr) | | SC F | | Bioconversion ratio | | |
|---|---|---|---|---|---|---|---|
| | Value | Range | Value | Range | from to | Value | Range |
| L-dopa 4'-mono-phosphate | 100 | 2-fold | 0.75 | 0.7-1 | L-dopa 4'-monophosphate to levdopa | 0.9 | 0.8-1 |
| levodopa | 24 | 2-fold | | | | | |
| Carbidopa 4'-mono-phosphate | 141 | 2-fold | 0.65 | 0.5-0.9 | Carbidopa 4'-monophosphate to carbidopa | 0.7 | 0.5-1 |
| carbidopa | 18 | 2-fold | | | | | |

CLp, plasma clearance;
SC: subcutaneous;
F: bioavailability

Using the point estimate values, a simulation of 150/38 mg/hr (L-dopa 4'-monophosphate/Carbidopa 4'-monophosphate) continuous SC infusion provides a steady state concentration (Css) of levodopa at 3000 ng/ml, with phosphorus load of 427 mg/day as shown Table 24-B.

TABLE 24-B

Point estimate of PK parameters of L-dopa 4'-monophosphate, levodopa, Carbidopa 4'-monophosphate and carbidopa.

| CLp | Dose rate | | Css | Css | Css | Css |
|---|---|---|---|---|---|---|
| Levodopa | L-dopa 4'-monophosphate/ Carbidopa 4'-monophosphate | phosphorus load | levodopa | L-dopa 4'-monophosphate | Carbidopa | Carbidopa 4'-monophosphate |
| (L/hr) | (mg/day) | (mg/day) | (ng/ml) | (ng/ml) | (ng/ml) | (ng/ml) |
| 24 | 3600/912 | 427 | 3000 | 1200 | 722 | 186 |

Example 24: Human Prediction of Steady State Exposures of L-Dopa and L-Dopa 4'-Monophosphate, Carbidopa and Carbidopa 4'-Monophosphate as Well as Phosphorus Daily Load Key factors for human prediction include:
1) linear human pharmacokinetics;
2) bioconversion ratios of prodrugs in human are estimated at the mean bioconversion ratios observed in preclinical animals (0.9 for L-dopa 4'-monophosphate and 0.7 for Carbidopa 4'-monophosphate);
3) high bioavailability (F) of monophosphate prodrugs after subcutaneous (SC) dosing (0.75 for L-dopa 4'-monophosphate and 0.65 for Carbidopa 4'-monophosphate);
4) phosphate release from prodrug is complete after SC dosing.
Projected PK parameters for monophosphate prodrug and active drugs are shown in Table 24-A.

The aqueous solubility of L-dopa 4'-monophosphate can reach as high as >300 mg/mL. One 20-mL vial of dose solution per day could deliver >6000 mg per day of L-dopa 4'-monophosphate, which could deliver the Css of levodopa of >5 ug/mL assuming linear human pharmacokinetics.

Example 25: Crystalline Carbidopa-4'-Monophosphate Trihydrate Preparation 95 mg sample of amorphous carbidopa-4'-monophosphate was weighed in a 8 mL vial and dissolved with 200 µl of water. 500 µL of isopropyl alcohol was added after all the solid was dissolved. The solution turned cloudy after the addition of the isopropanol. The cloudy suspension was stirred using a magnetic stir bar at room temperature for 15 min. Then 200 µL of IPA was added. The slurry was stirred for an hour and then filtered. The wet cake was washed with 1 mL of IPA. The solid was air-dried overnight and then analyzed by powder x-ray diffraction (PXRD) the following day. The PXRD pattern for crystalline carbidopa-4'-monophosphate trihydrate is shown in FIG. 17.

Example 26a: Crystalline Carbidopa-4'-Monophosphate Dihydrate Preparation 420 mg of carbidopa-4'-monophosphate trihydrate was weighed into a 20 mL vial. 8.4 mL of n-butanol was added to the vial, and the content was stirred overnight at 30° C. with a magnetic stir bar. A wet cake sample was isolated and analyzed by PXRD. The PXRD pattern for crystalline carbidopa-4'-monophosphate dihydrate is shown in FIG. 18.

Example 26b: Crystalline Carbidopa-4'-Monophosphate Dihydrate Preparation 103 mg of amorphous carbidopa-4'-monophosphate was weighed into a 4 mL vial. 200 µl of water was added. After all the solids were dissolved, 500 µl of isopropyl alcohol was added and the solution was stirred at room temperature using a magnetic stir bar. 30 min later solids were observed in the vial. At that point 200 µl of IPA was added and the slurry was stirred for 30 more min. The solids were then isolated and a PXRD pattern of the wet cake was analyzed. The PXRD pattern of the wet cake was consistent with the PXRD pattern shown in FIG. 18.

Example 27: Crystalline Carbidopa-4'-Monophosphate Dehydrate Preparation

About 10 mg of carbidopa-4'-monophosphate trihydrate was loaded on a tared aluminum pan of the DVS Advantage (Surface Measurement Systems Ltd, Alperton, United Kingdom). The sample was subjected to the following humidity conditions at 25° C.: 30-0-90-0-30% relative humidity (RH) in 10% RH intervals. For each step, the dm/dt (change of mass over change in time) criteria was 0.001% over 5 minutes and a minimum dm/dt time of 30 minutes and a maximum dm/dt of 120 minutes. The nitrogen flow rate during analysis 200 was cc/min. The post-DVS sample was kept at 30% RH prior to PXRD analysis. The PXRD pattern for crystalline carbidopa-4'-monophosphate dehydrate is shown in FIG. 19.

Example 28: Crystalline L-Dopa-3'-Monophosphate Preparation

Crystalline L-dopa-3'-monophosphate was prepared according to Example 1 (Steps 1, 2, 3, 4b, 5b) described above. The PXRD pattern for crystalline L-dopa-3'-monophosphate is shown in FIG. 15.

Example 29: Crystalline L-Dopa-4'-Monophosphate Anhydrate (i) Preparation

Crystalline L-dopa-4'-monophosphate anhydrate (i) was prepared according to Example 5 described above. The PXRD pattern for crystalline L-dopa-4'-monophosphate anhydrate (i) is shown in FIG. 13.

Example 30: Crystalline L-Dopa-4'-Monophosphate Anhydrate (ii) Preparation 204 mg of L-dopa-4'-monophosphate anhydrate (i) was weighed in a 4-mL vial. 1 mL of dimethyl sulfoxide and 1 mL of water was added. The resulting slurry was stirred at 24° C. The solid was then filtered, air-dried and analyzed by PXRD. The PXRD pattern for crystalline L-dopa-4'-monophosphate anhydrate (ii) is shown in FIG. 14.

Example 31: Crystalline Carbidopa-3'-Monophosphate (i) Preparation 100 mg of amorphous carbidopa-3'-monophosphate was weighed in a 4 mL vial. 300 µl of water was added. Once the solid was dissolved, 600 µl of isopropanol was added. The resulting clear solution was stirred with a magnetic stir bar at room temperature overnight until solids came out of solution. 300 µl of isopropanol was added and the suspension was stirred for 15 min. The suspension was then filtered and the resulting solid was dried in a vacuum oven at room temperature. The dried solid was analyzed by PXRD. The PXRD pattern for crystalline carbidopa-3'-monophosphate (i) is shown in FIG. 20.

Example 32: Crystalline Carbidopa-3'-Monophosphate (ii) Preparation 25 mg of carbidopa-3'-monophosphate (i) was weighed in a 2 ml vial. 100 µl of water was added to dissolve the solid. The vial was placed in a Crystal 16 instrument (Avantium Technologies, Amsterdam, Netherlands) and subjected to the following heat/cool cycle while stirring with a magnetic stir bar: ramp at 10° C./h to 50° C., hold for 4 h, ramp at 20° C./hr to −15° C., hold for 4 h, ramp at 10° C./h to 50° C., hold for 4 h, ramp to −15° C. at 10° C./h, hold for 4 h, ramp to 50° C. at 10° C./h, hold for 4 h, ramp to −15° C. at 5° C./h, hold for 4 h, ramp to 25° C. at 10° C./h and hold until PXRD analysis. The solid was then filtered and the wet cake was analyzed by PXRD. The PXRD pattern for crystalline carbidopa-3'-monophosphate (ii) is shown in FIG. 21.

Example 33: Crystalline Carbidopa-3',4'-Diphosphate Sodium Salt Preparation 46 mg of amorphous carbidopa 3',4'-diphosphate and 5.6 mg of sodium hydroxide pellets was dissolved in 500 µL of dimethyl sulfoxide and 200 µL of water. 400 mg of IPA was added. The solution was then heated to 35° C., and then allowed to cool to room temperature. The solution was stirred with a magnetic stir bar until needles precipitated out. The solid was then filtered out and analyzed by PXRD. The PXRD pattern for crystalline carbidopa-3',4'-diphosphate sodium salt is shown in FIG. 22.

Example 34: Crystalline L-Dopa-3',4'-Diphosphate Trihydrate Preparation 62.1 mg of amorphous L-dopa 3',4'-diphosphate was weighed in a 2 ml vial. 200 µl of water was added to dissolve the solid. The vial was placed in a Crystal 16 instrument (Avantium Technologies, Amsterdam, Netherlands) and subjected to the following heat/cool cycle while stirring with a magnetic stir bar: ramp at 10° C./h to 50° C., hold for 4 h, ramp at 20° C./hr to −15° C., hold for 4 h, ramp at 10° C./h to 50° C., hold for 4 h, ramp to −15° C. at 10° C./h, hold for 4 h, ramp to 50° C. at 10° C./h, hold for 4 h, ramp to −15° C. at 5° C./h, hold for 4 h, ramp to 25° C. at 10° C./h and hold until PXRD analysis. The solid was then filtered and the wet cake was analyzed by PXRD. The PXRD pattern for crystalline L-dopa-3',4'-diphosphate trihydrate is shown in FIG. 16.

Alternatively, ethyl acetate, isopropanol, water-saturated ethyl acetate, methyl ethyl ketone, acetone, tetrahydrofuran, toluene, 2-methyl THF, dichloromethane, tert-tributylamine, isobutylacetate, 1,4-dioxane can also be used as solvents to crystallize out L-dopa-3',4'-diphosphate trihydrate. The following mixtures of solvents in a 1:1 ratio by volume can be used as well: acetone/water, isopropyl acetate/heptane.

X. FURTHER EMBODIMENTS

Embodiment 1

A pharmaceutical combination comprising a first compound corresponding in structure to Formula (I):

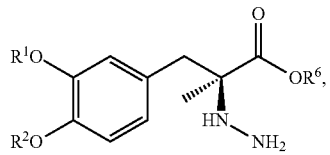
(I)

or a pharmaceutically acceptable salt thereof, wherein $R^1$ and $R^2$ are each independently selected from the group consisting of hydrogen, —P(O)(OH)$_2$, and —$R^5$—O—P(O)(OH)$_2$; $R^5$ is a $C_1$-$C_4$-alkyl; $R^6$ is hydrogen or a $C_1$-$C_4$-alkyl; and provided that at least one of $R^1$ and $R^2$ is —P(O)(OH)$_2$ or —$R^5$—O—P(O)(OH)$_2$; and a second compound corresponding in structure Formula (II):

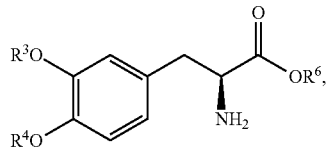
(II)

or a pharmaceutically acceptable salt thereof, wherein $R^3$ and $R^4$ are each independently selected from the group consisting of hydrogen, —P(O)(OH)$_2$, and —$R^5$—O—P(O)(OH)$_2$; $R^5$ is a $C_1$-$C_4$-alkyl; $R^6$ is hydrogen or a $C_1$-$C_4$-alkyl; and provided that at least one of $R^3$ and $R^4$ is —P(O)(OH)$_2$ or —$R^5$—O—P(O)(OH)$_2$.

Embodiment 2

The pharmaceutical combination of Embodiment 1, wherein the first compound is

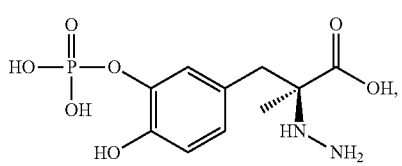
(I-a)

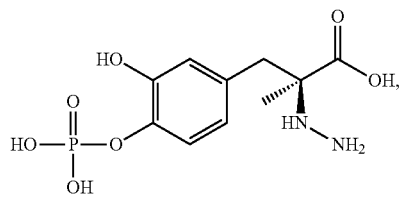
(I-b)

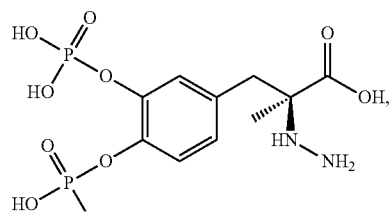
(I-c)

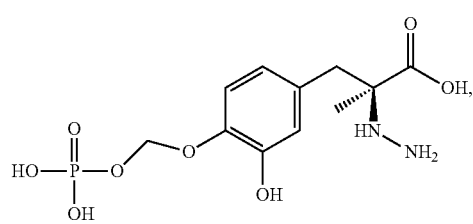
(I-d)

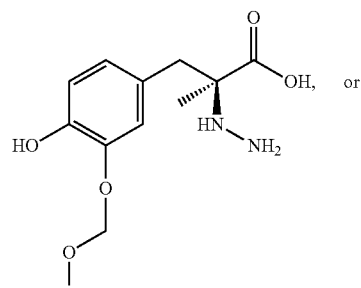
(I-e) or

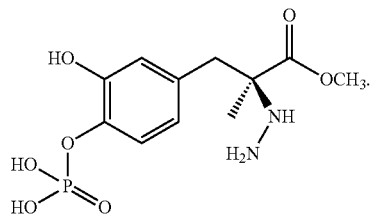
(I-f)

Embodiment 3

The pharmaceutical combination of Embodiment 1 or 2, wherein the second compound is

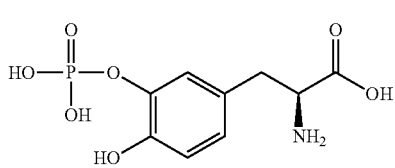
(II-a)

-continued

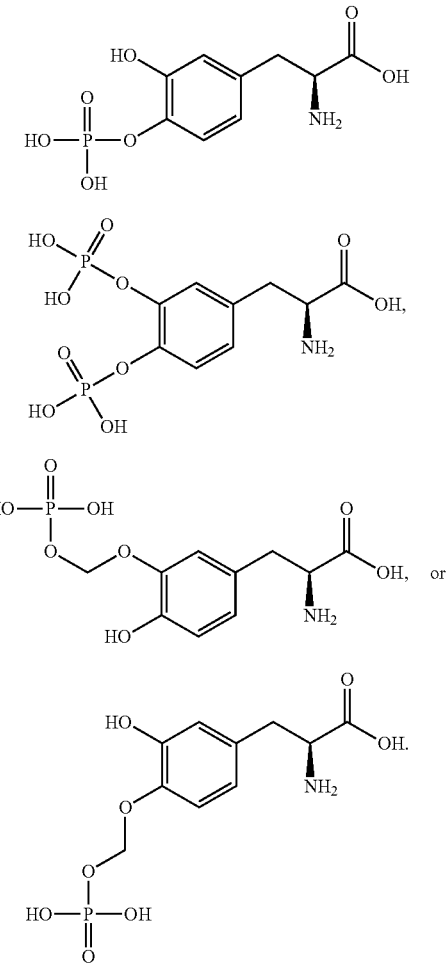

(II-b)

(II-c)

(II-d)

(II-e)

Embodiment 4

The pharmaceutical combination of any one of the previous embodiments wherein the first compound or pharmaceutically acceptable salt thereof, and the second compound or pharmaceutically acceptable salt thereof are present in separate pharmaceutical compositions or are both present in the same pharmaceutical composition.

Embodiment 5

The pharmaceutical combination of any one of the previous embodiments, wherein a weight ratio of the first compound or pharmaceutically acceptable salt thereof to the second compound or pharmaceutically acceptable salt thereof is about 1:1 to about 1:50, preferably about 1:2 to about 1:15, preferably about 1:4 to about 1:10, and more preferably about 1:4.

Embodiment 6

The pharmaceutical combination of any one of the previous embodiments, wherein the first compound or pharmaceutically acceptable salt thereof has a solubility of at least about 200 mg/ml in aqueous solution at about neutral pH, and the second compound or pharmaceutically acceptable salt thereof has a solubility of at least about 400 mg/ml in aqueous solution at about neutral pH.

Embodiment 7

The pharmaceutical combination of any one of the previous embodiments, wherein the combination is an aqueous combination suitable for intragastric, subcutaneous, intramuscular, intrajejunum, oral, intranasal or intravenous administration.

Embodiment 8

The pharmaceutical combination of any one of the previous embodiments, wherein the combination is an aqueous combination suitable for subcutaneous administration.

Embodiment 9

The pharmaceutical combination of any one of the previous embodiments, wherein the first compound is a compound corresponding in structure to Formula (I-a):

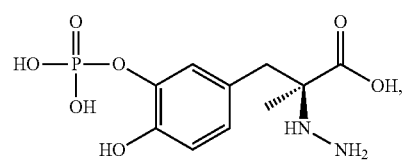

(I-a)

or a pharmaceutically acceptable salt thereof; and the second compound is a compound corresponding in structure to Formula (II-a):

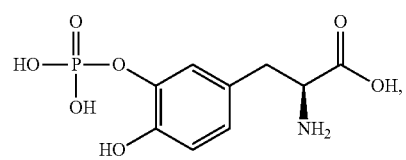

(II-a)

or a pharmaceutically acceptable salt thereof.

Embodiment 10

The pharmaceutical combination of any one of the previous embodiments, wherein the first compound is a compound corresponding in structure to Formula (I-b):

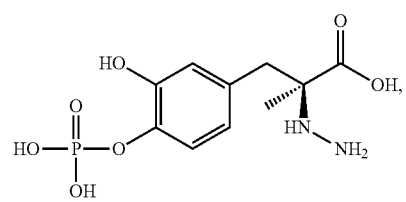

(I-b)

or a pharmaceutically acceptable salt thereof; and the second compound is a compound corresponding in structure to Formula (II-a):

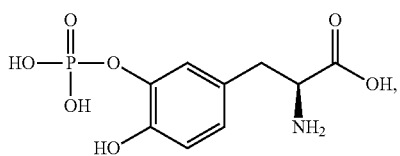

or a pharmaceutically acceptable salt thereof.

Embodiment 11

The pharmaceutical combination of any one of the previous embodiments, wherein the first compound is a compound corresponding in structure to Formula (I-c).

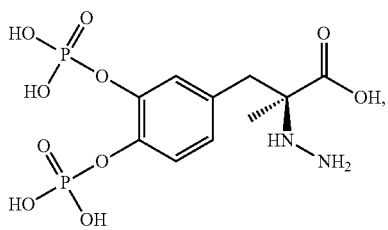

or a pharmaceutically acceptable salt thereof; and the second compound is a compound corresponding in structure to Formula (II-a):

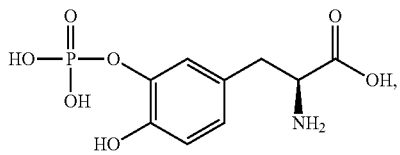

or a pharmaceutically acceptable salt thereof.

Embodiment 12

The pharmaceutical combination of any one of the previous embodiments, wherein the first compound is a compound corresponding in structure to Formula (I-a):

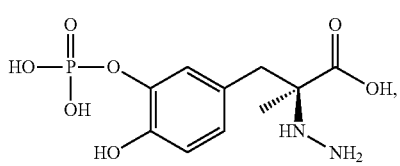

or a pharmaceutically acceptable salt thereof; and the second compound is a compound corresponding in structure to Formula (II-b):

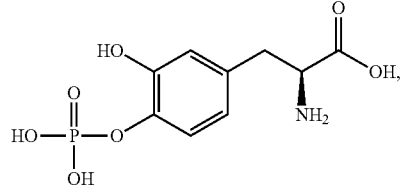

or a pharmaceutically acceptable salt thereof.

Embodiment 13

The pharmaceutical combination of any one of the previous embodiments, wherein the first compound is a compound corresponding in structure to Formula (I-b):

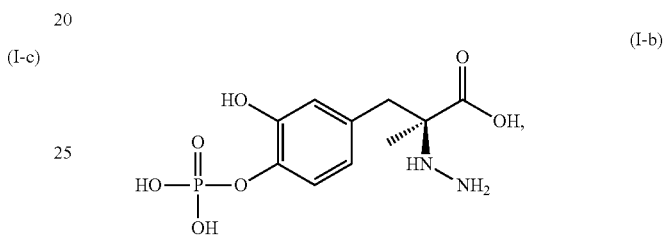

or a pharmaceutically acceptable salt thereof; and the second compound is a compound corresponding in structure to Formula (II-b):

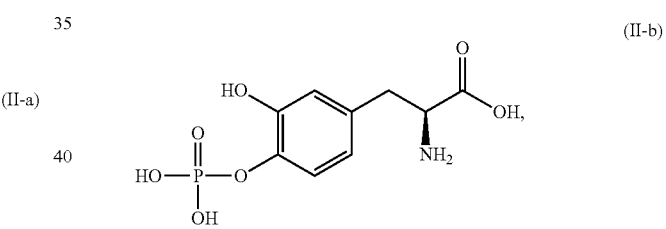

or a pharmaceutically acceptable salt thereof.

Embodiment 14

The pharmaceutical combination of any one of the previous embodiments, wherein the first compound is a compound corresponding in structure to Formula (I-c):

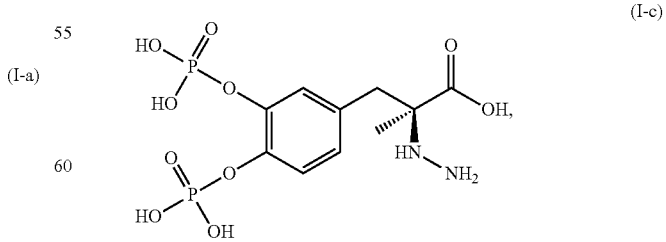

or a pharmaceutically acceptable salt thereof; and the second compound is a compound corresponding in structure to Formula (II-b):

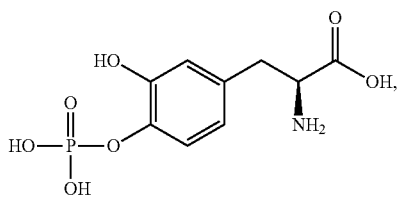

(II-b)

or a pharmaceutically acceptable salt thereof.

Embodiment 15

The pharmaceutical combination of any one of the previous embodiments, wherein the first compound is a compound corresponding in structure to Formula (I-a):

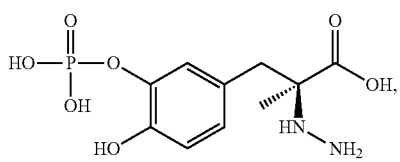

(I-a)

or a pharmaceutically acceptable salt thereof; and the second compound is a compound corresponding in structure to Formula (II-c):

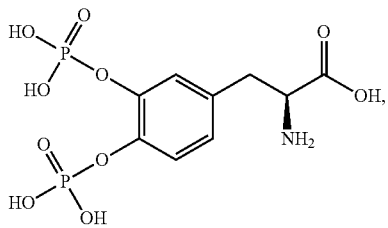

(II-c)

or a pharmaceutically acceptable salt thereof.

Embodiment 16

The pharmaceutical combination of any one of the previous embodiments, wherein the first compound is a compound corresponding in structure to Formula (I-b):

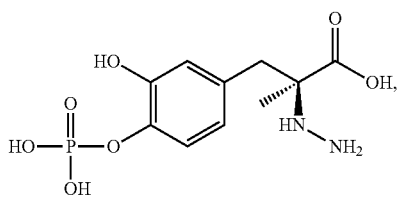

(I-b)

or a pharmaceutically acceptable salt thereof; and the second compound is a compound corresponding in structure to Formula (II-c):

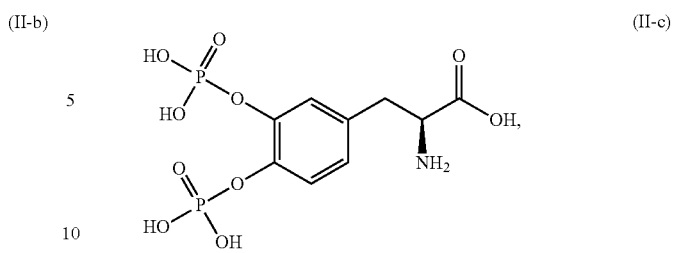

(II-c)

or a pharmaceutically acceptable salt thereof.

Embodiment 17

The pharmaceutical combination of any one of the previous embodiments, wherein the first compound is a compound corresponding in structure to Formula (I-c):

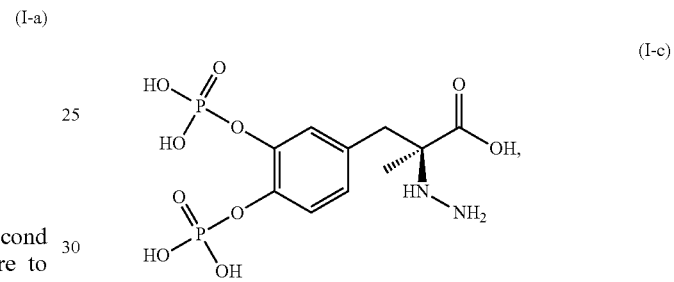

(I-c)

or a pharmaceutically acceptable salt thereof; and the second compound is a compound corresponding in structure to Formula (II-c):

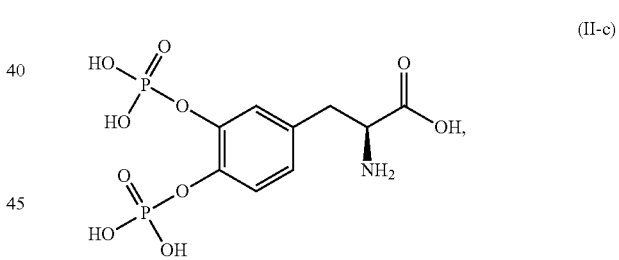

(II-c)

or a pharmaceutically acceptable salt thereof.

Embodiment 18

A method of treating Parkinson's disease in a subject in need thereof and/or a method of providing rescue therapy in a subject having Parkinson's disease, the method comprising administering to the subject a therapeutically effective amount of the pharmaceutical combination according to any one of the previous embodiments.

Embodiment 19

The method of Embodiment 18, wherein the first compound and the second compound are administered in separate pharmaceutical compositions to the subject, or the first compound and the second compound are administered to the subject in the same pharmaceutical composition comprising the first compound and the second compound.

Embodiment 20

The method of Embodiment 18 or 19, wherein the method comprises intragastric, subcutaneous, intrajejunum, oral, intranasal, intramuscular or intravenous administration of the first compound and the second compound.

Embodiment 21

The method of any one of Embodiments 18-20, wherein the method comprises subcutaneous administration of the first compound and the second compound.

Embodiment 22

The method of any one of Embodiments 18-21, wherein the method comprises substantially continuous administration of the first compound and the second compound over a period of at least about 12 hours.

Embodiment 23

The method of any one of Embodiments 18-22, wherein the weight ratio of the first compound administered to the second compound administered is from about 1:1 to about 1:50.

Embodiment 24

The method of any one of Embodiments 18-23, wherein the weight ratio of the first compound administered to the second compound administered is from about 1:2 to about 1:15.

Embodiment 25

The method of any one of Embodiments 18-24, wherein the weight ratio of the first compound administered to the second compound administered is from about 1:4 to about 1:10.

Embodiment 26

The method of any one of Embodiments 18-25, wherein the weight ratio of the first compound administered to the second compound administered is about 1:4.

Embodiment 27

The method of any one of Embodiments 18-26, wherein the weight ratio of the first compound administered to the second compound administered is about 1:7.5.

Embodiment 28

The method of any one of Embodiments 18-27, wherein the weight ratio of the first compound administered to the second compound administered is about 1:10.

Embodiment 29

The method of any one of Embodiments 18-28, wherein the first compound is selected from the group consisting of

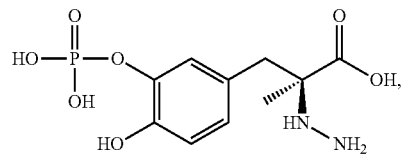
(I-a)

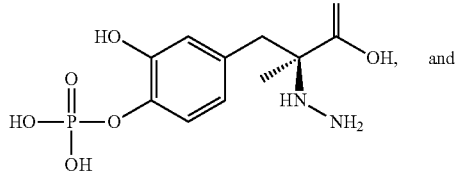
(I-b)

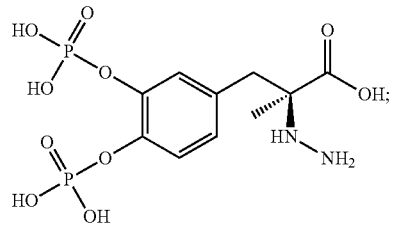
(I-c)

and the second compound is selected from the group consisting of

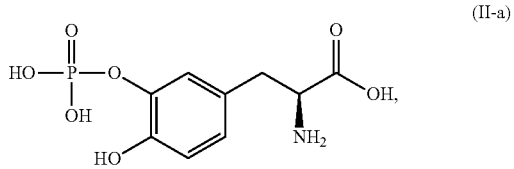
(II-a)

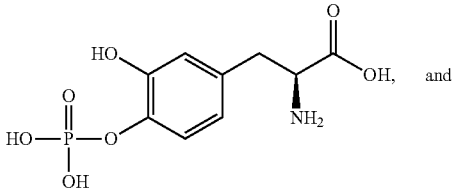
(II-b)

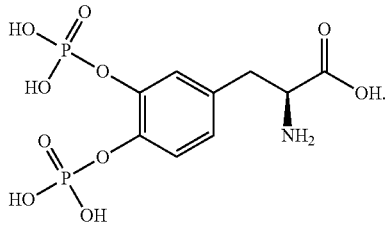
(II-c)

Embodiment 30

The method of any one of Embodiments 18-29 further comprising administering another anti-Parkinson's agent to the subject.

Embodiment 31

The method of any one of Embodiments 18-30, wherein the pharmaceutical combination is an aqueous combination.

Embodiment 32

The method of Embodiment 31, wherein the aqueous pharmaceutical combination is administered by intragastric, subcutaneous, intramuscular, intranasal, intrajejunum, oral or intravenous administration.

Embodiment 33

The method of Embodiments 31 or 32, wherein the aqueous pharmaceutical combination is administered by subcutaneous administration.

Embodiment 34

A compound corresponding in structure to Formula (I):

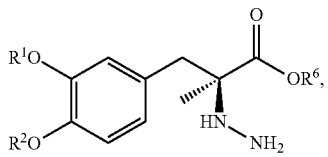

(I)

or a pharmaceutically acceptable salt thereof, wherein $R^1$ and $R^2$ are each independently selected from the group consisting of hydrogen, —P(O)(OH)$_2$, and —R$^5$—O—P(O)(OH)$_2$; R$^5$ is a C$_1$-C$_4$-alkyl; R$^6$ is hydrogen or a C$_1$-C$_4$-alkyl; and provided that at least one of $R^1$ and $R^2$ is —P(O)(OH)$_2$ or —R$^5$—O—P(O)(OH)$_2$.

Embodiment 35

The compound or pharmaceutically acceptable salt of Embodiment 34, wherein $R^1$ and $R^2$ are each independently selected from the group consisting of hydrogen, —P(O)(OH)$_2$, and —R$^5$—O—P(O)(OH)$_2$; R$^5$ is a C$_1$-C$_2$-alkyl; R$^6$ is hydrogen; and provided that at least one of $R^1$ and $R^2$ is —P(O)(OH)$_2$ or —R$^5$—O—P(O)(OH)$_2$.

Embodiment 36

The compound or pharmaceutically acceptable salt of Embodiment 34 or 35, wherein $R^1$ and $R^2$ are each independently hydrogen or —P(O)(OH)$_2$; R$^6$ is hydrogen; and one of $R^1$ and $R^2$ is —P(O)(OH)$_2$.

Embodiment 37

The compound or pharmaceutically acceptable salt of Embodiment 34 or 35, wherein $R^1$ and $R^2$ are each independently hydrogen or —R$^5$—O—P(O)(OH)$_2$; R$^5$ is a C$_1$-C$_2$-alkyl; R$^6$ is hydrogen; and provided that one of $R^1$ and $R^2$ is —R$^5$—O—P(O)(OH)$_2$.

Embodiment 38

The compound or pharmaceutically acceptable salt of Embodiment 34, wherein $R^1$ and $R^2$ are each independently hydrogen, —P(O)(OH)$_2$ or —R$^5$—O—P(O)(OH)$_2$; R$^5$ is a C$_1$-C$_2$-alkyl; R$^6$ is a C$_1$-C$_2$-alkyl; and provided that one of $R^1$ and $R^2$ is —P(O)(OH)$_2$ or —R$^5$—O—P(O)(OH)$_2$.

Embodiment 39

The compound or salt of any one of Embodiments 34-36, wherein the compound corresponds in structure to Formula (I-a):

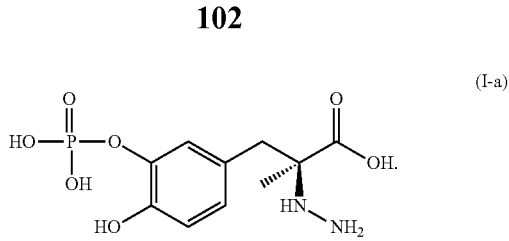

(I-a)

Embodiment 40

The compound or salt of any one of Embodiments 34-36, wherein the compound corresponds in structure to Formula (I-b):

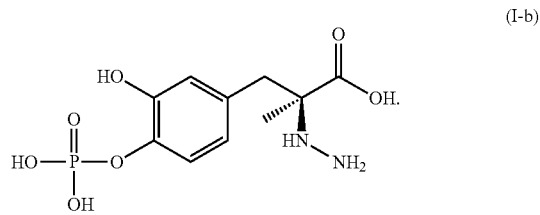 [SMILES: C[C@@](Cc1ccc(OP(=O)(O)O)c(O)c1)(NN)C(=O)O]

(I-b)

Embodiment 41

The compound or salt of any one of Embodiments 34-36, wherein the compound corresponds in structure to Formula (I-c):

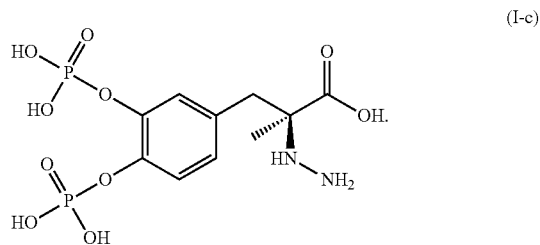 [SMILES: C[C@@](Cc1ccc(OP(=O)(O)O)c(OP(=O)(O)O)c1)(NN)C(=O)O]

(I-c)

Embodiment 42

The compound or salt of any one of Embodiments 34, 35 or 37, wherein the compound corresponds in structure to Formula (I-d):

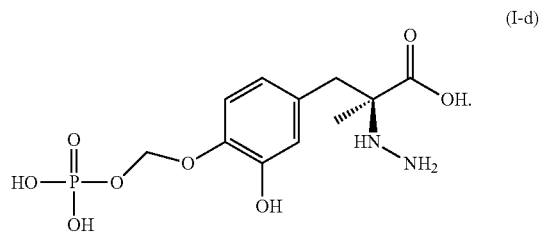 [SMILES: C[C@@](Cc1ccc(OCOP(=O)(O)O)c(O)c1)(NN)C(=O)O]

(I-d)

Embodiment 43

The compound or salt of any one of Embodiments 34, 35 or 37, wherein the compound corresponds in structure to Formula (I-e):

(I-e)

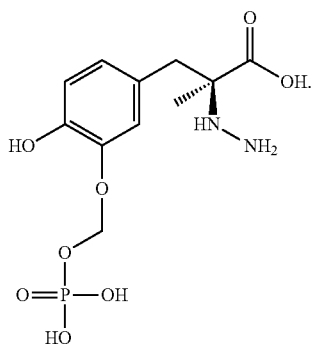

Embodiment 44

The compound or salt of any one of Embodiments 34 or 38, wherein the compound corresponds in structure to Formula (I-f):

(I-f)

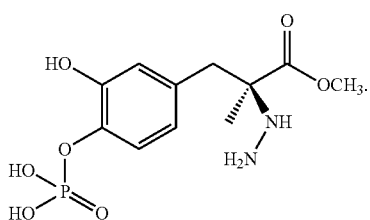

Embodiment 45

A compound corresponding in structure to Formula (II):

(II)

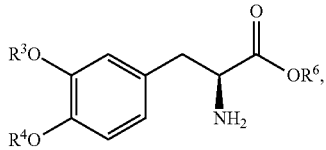

or a pharmaceutically acceptable salt thereof, wherein $R^3$ and $R^4$ are each independently selected from the group consisting of hydrogen, —P(O)(OH)$_2$, and —R$^5$—O—P(O)(OH)$_2$; $R^5$ is a $C_1$-$C_4$-alkyl; $R^6$ is hydrogen or a $C_1$-$C_4$-alkyl; and provided that at least one of $R^3$ and $R^4$ is —P(O)(OH)$_2$ or —R$^5$—O—P(O)(OH)$_2$.

Embodiment 46

The compound or salt of Embodiment 45, wherein $R^3$ and $R^4$ are each independently hydrogen or —R$^5$—O—P(O)(OH)$_2$; $R^5$ is a $C_1$-$C_2$-alkyl; $R^6$ is hydrogen; and provided that one of $R^3$ and $R^4$ is —R$^5$—O—P(O)(OH)$_2$.

Embodiment 47

The compound or salt of Embodiment 45 or 46, wherein the compound corresponds in structure to Formula (II-d):

(II-d)

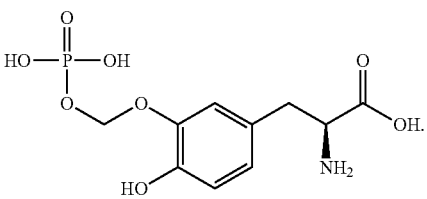

Embodiment 48

The compound or salt of Embodiment 45 or 46, wherein the compound corresponds in structure to Formula (II-e):

(II-e)

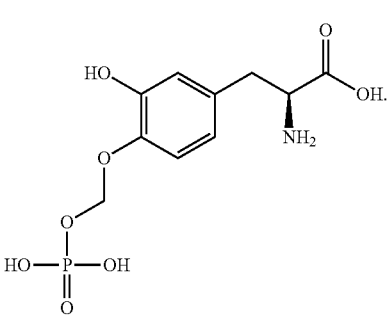

Embodiment 49

A pharmaceutical composition comprising a first compound corresponding in structure to Formula (I):

(I)

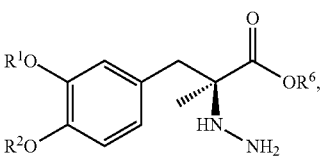

or a pharmaceutically acceptable salt thereof, wherein $R^1$ and $R^2$ are each independently selected from the group consisting of hydrogen, —P(O)(OH)$_2$, and —R$^5$—O—P(O)(OH)$_2$; $R^5$ is a $C_1$-$C_4$-alkyl; $R^6$ is hydrogen or a $C_1$-$C_4$-alkyl; and provided that at least one of $R^1$ and $R^2$ is —P(O)(OH)$_2$ or —R$^5$—O—P(O)(OH)$_2$; and a pharmaceutically acceptable carrier.

Embodiment 50

The pharmaceutical composition of Embodiment 49, wherein the first compound corresponds in structure to Formula (I-a):

(I-a)

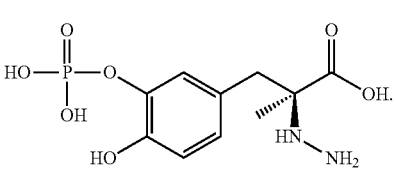

Embodiment 51

The pharmaceutical composition of Embodiment 49, wherein the first compound corresponds in structure to Formula (I-b):

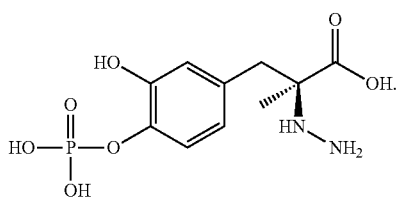

(I-b)

Embodiment 52

The pharmaceutical composition of Embodiment 49, wherein the first compound corresponds in structure to Formula (I-c):

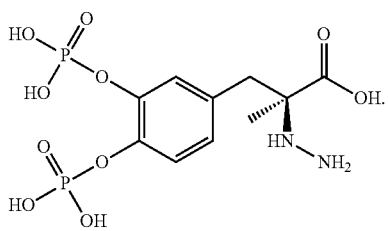

(I-c)

Embodiment 53

The pharmaceutical composition of any one of Embodiments 49-52, wherein the composition further comprises a second compound corresponding in structure to Formula (II):

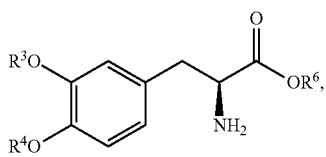

(II)

or a pharmaceutically acceptable salt thereof, wherein $R^3$ and $R^4$ are each independently selected from the group consisting of hydrogen, —P(O)(OH)$_2$, and —$R^5$—O—P(O)(OH)$_2$; $R^5$ is a $C_1$-$C_4$-alkyl; $R^6$ is hydrogen or a $C_1$-$C_4$-alkyl; and provided that at least one of $R^3$ and $R^4$ is —P(O)(OH)$_2$ or —$R^5$—O—P(O)(OH)$_2$.

Embodiment 54

The pharmaceutical composition of Embodiment 53, wherein the second compound corresponds in structure to Formula (II-a):

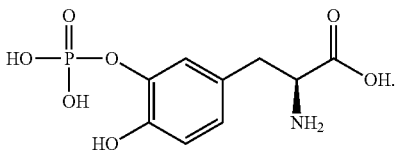

(II-a)

Embodiment 55

The pharmaceutical composition of Embodiment 53, wherein the second compound corresponds in structure to Formula (II-b):

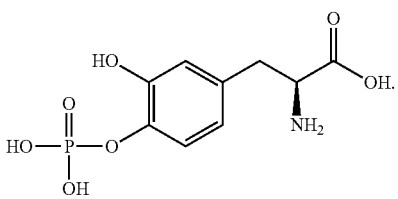

(II-b)

Embodiment 56

The pharmaceutical composition of Embodiment 53, wherein the second compound corresponds in structure to Formula (II-c):

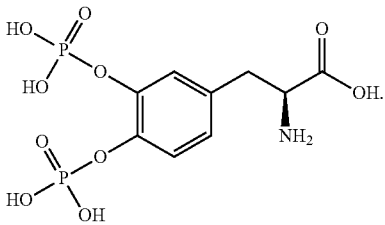

(II-c)

Embodiment 57

The pharmaceutical composition of any one of Embodiments 37-44, wherein the weight ratio of the first compound to the second compound is from about 1:1 to about 1:50, preferably from about 1:2 to about 1:15, even more preferably from about 1:4 to about 1:10.

Embodiment 58

The pharmaceutical composition of any one of Embodiments 49-57, wherein the weight ratio of the first compound to the second compound is about 1:4.

Embodiment 59

The pharmaceutical composition of any one of Embodiments 49-57, wherein the weight ratio of the first compound to the second compound is about 1:7.5.

Embodiment 60

The pharmaceutical composition of any one of Embodiments 49-57, wherein the weight ratio of the first compound to the second compound is about 1:10.

Embodiment 61

The pharmaceutical composition of any one of Embodiments 49-60, wherein the composition further comprises water and is suitable for infusion.

Embodiment 62

A kit comprising the pharmaceutical combination of any one of Embodiments 1-17.

Embodiment 63

A kit comprising the pharmaceutical composition of any one of Embodiments 49-62.

Embodiment 64

A compound selected from the group consisting of

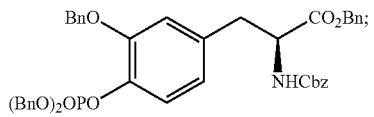  (a)

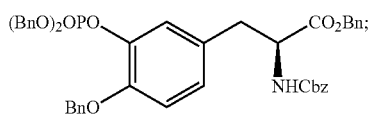  (b)

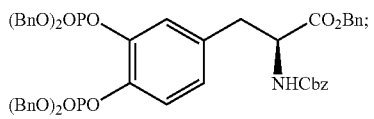  (c)

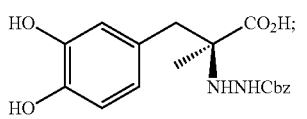  (d)

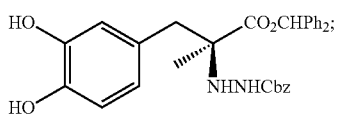  (e)

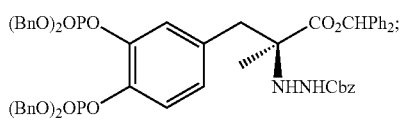  (f)

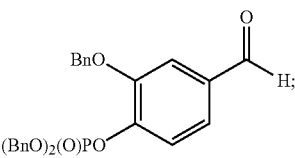  (g)

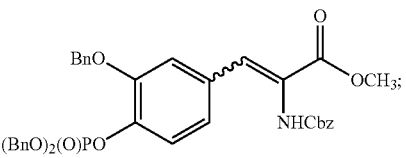  (h)

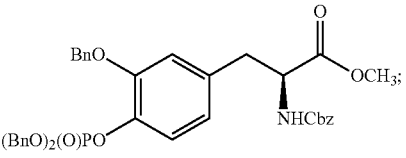  (i)

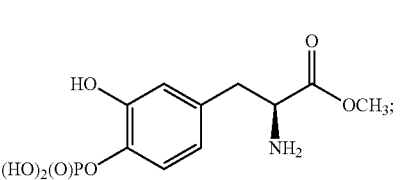  (j)

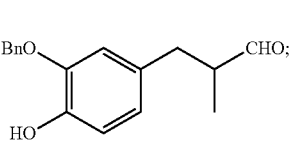  (k)

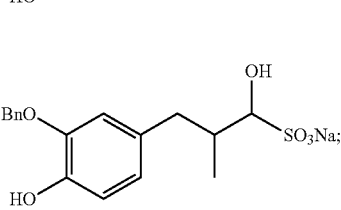  (l)

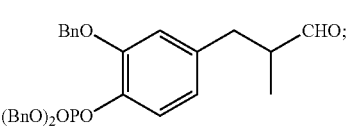  (m)

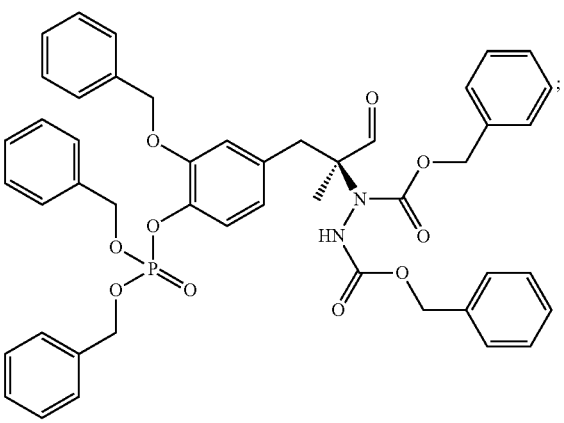  (n)

-continued

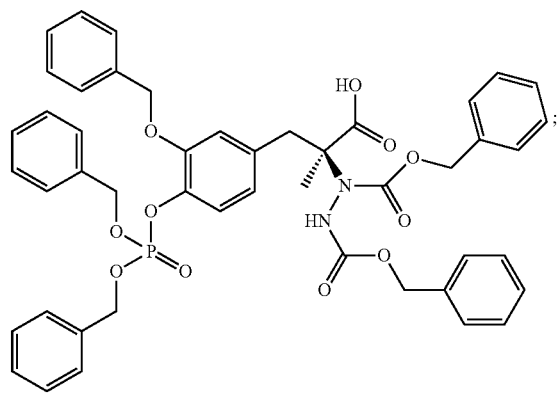 (o)

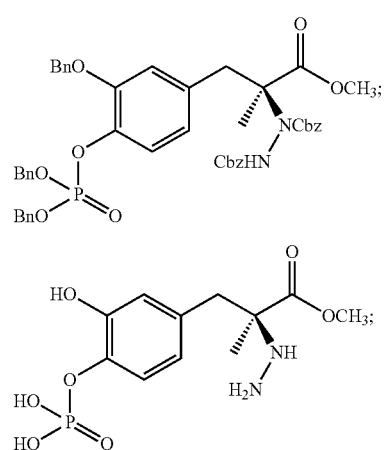 (p)

(q)

(r)

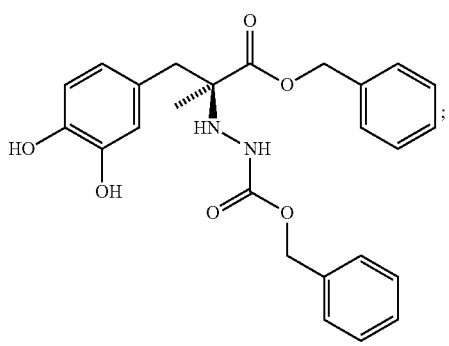 (s)

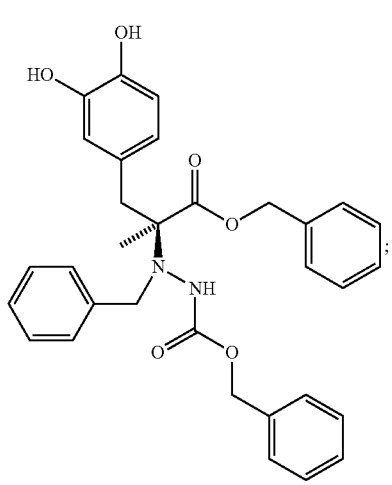

-continued

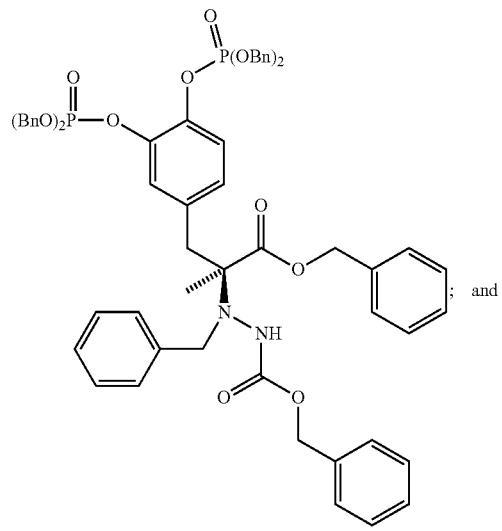 (t)

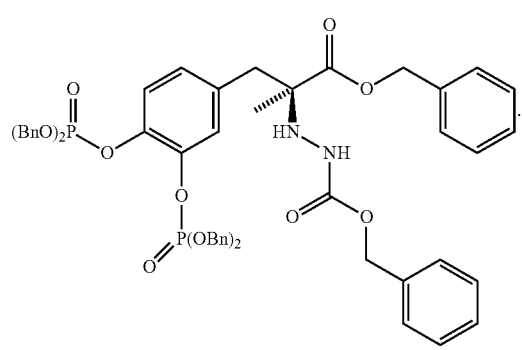 (u)

Embodiment 65

A crystalline polymorph of L-dopa 4'-monophosphate identified by powder X-ray diffraction wherein the crystalline polymorph is:

crystalline L-dopa 4'-monophosphate anhydrate (i) demonstrating at least one characteristic peak in the powder X-ray diffraction pattern at values of two theta of 10.261±0.20, 12.053±0.20, 13.759±0.20, 14.932±0.20, 16.147±0.20, 16.718±0.20, 17.34±0.20, 19.254±0.20, 20.654±0.20, 22.078±0.20, 23.599±0.20, 24.198±0.20, 25.898±0.20, 26.338±0.20, and 27.117±0.20; or crystalline L-dopa 4'-monophosphate anhydrate (ii) demonstrating at least one characteristic peak in the powder X-ray diffraction pattern at values of two theta of 8.468±0.20, 10.234±0.20, 11.821±0.20, 13.084±0.20, 13.503±0.20, 15.48±0.20, 15.848±0.20, 16.513±0.20, 18.447±0.20, 19.346±0.20, 20.239±0.20, 21.139±0.20, 24.221±0.20, 24.865±0.20, 25.647±0.20.

Embodiment 66

A crystalline L-dopa 3'-monophosphate demonstrating at least one characteristic peak in the powder X-ray diffraction pattern at values of two theta of 8.662±0.20, 11.286±0.20, 15.079±0.20, 15.678±0.20, 16.786±0.20, 17.288±0.20, 18.438±0.20, 19.682±0.20, 20.946±0.20, 22.188±0.20, 22.671±0.20, 23.088±0.20, 24.144±0.20, 24.744±0.20, and 25.383±0.20.

Embodiment 67

A crystalline L-dopa 3'4-diphosphate trihydrate demonstrating at least one characteristic peak in the powder X-ray diffraction pattern at values of two theta of 7.118±0.20, 10.342±0.20, 11.355±0.20, 12.161±0.20, 14.201±0.20, 17.36±0.20, 17.632±0.20, 19.196±0.20, 19.444±0.20, 20.83±0.20, 21.504±0.20, 22.491±0.20, 23.085±0.20, 24.487±0.20, and 25.11±0.20.

Embodiment 68

A crystalline polymorph of carbidopa 4'-monophosphate identified by powder X-ray diffraction wherein the crystalline polymorph is:

crystalline carbidopa 4'-monophosphate trihydrate demonstrating at least one characteristic peak in the powder X-ray diffraction pattern at values of two theta of 7.484±0.20, 10.05±0.20, 11.971±0.20, 13.085±0.20, 14.923±0.20, 16.095±0.20, 16.85±0.20, 17.359±0.20, 17.635±0.20, 19.269±0.20, 19.544±0.20, 21.842±0.20, 22.578±0.20, 22.921±0.20, and 23.822±0.20;

crystalline carbidopa 4'-monophosphate dihydrate demonstrating at least one characteristic peak in the powder X-ray diffraction pattern at values of two theta of 7.925±0.20, 10.28±0.20, 12.344±0.20, 15.002±0.20, 15.841±0.20, 16.158±0.20, 17.565±0.20, 18.506±0.20, 19.058±0.20, 19.473±0.20, 19.702±0.20, 20.188±0.20, 20.668±0.20, 22.37±0.20, and 24.167±0.20; or crystalline carbidopa 4'-monophosphate dehydrate demonstrating at least one characteristic peak in the powder X-ray diffraction pattern at values of two theta of 9.492±0.20, 10.528±0.20, 15.356±0.20, 15.907±0.20, 16.165±0.20, 17.933±0.20, 18.737±0.20, 19.429±0.20, 21.176±0.20, and 22.626±0.20.

Embodiment 69

A crystalline polymorph of carbidopa 3'-monophosphate identified by powder X-ray diffraction wherein the crystalline polymorph is:

crystalline carbidopa 3'-monophosphate (i) demonstrating at least one characteristic peak in the powder X-ray diffraction pattern at values of two theta of 9.171±0.20, 13.539±0.20, 14.23±0.20, 15.589±0.20, 15.979±0.20, 18.394±0.20, 18.832±0.20, 19.315±0.20, 22.143±0.20, and 22.81±0.20; or crystalline carbidopa 3'-monophosphate (ii) demonstrating at least one characteristic peak in the powder X-ray diffraction pattern at values of two theta of 4.433±0.20, 8.917±0.20, 9.654±0.20, 13.192±0.20, 15.288±0.20, 15.747±0.20, 17.886±0.20, 19.291±0.20, 20.554±0.20, and 21.797.

Embodiment 70

A crystalline carbidopa 3'4-diphosphate sodium salt demonstrating at least one characteristic peak in the powder X-ray diffraction pattern at values of two theta of 5.852±0.20, 6.861±0.20, 7.338±0.20, 11.159±0.20, 11.729±0.20, 12.953±0.20, 13.714±0.20, 14.381±0.20, 14.686±0.20, 15.479±0.20, 16.676±0.20, 17.179±0.20, 17.592±0.20, 18.861±0.20 and 20.305±0.20.

It is understood that the foregoing detailed description and accompanying examples are merely illustrative and are not to be taken as limitations upon the scope of the invention, which is defined solely by the appended claims and their equivalents.

Various changes and modifications to the disclosed embodiments will be apparent to those skilled in the art. Such changes and modifications, including without limitation those relating to the chemical structures, substituents, derivatives, intermediates, syntheses, compositions, formulations, or methods of use of the invention, may be made without departing from the spirit and scope thereof.

What is claimed is:

1. An aqueous pharmaceutical composition comprising:
   (a) a first compound corresponding in structure to Formula (I)-b:

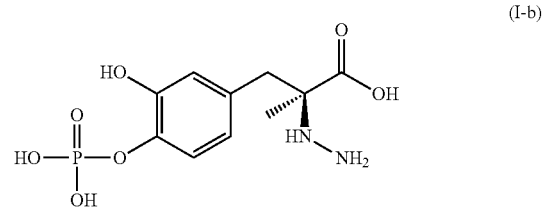 [SMILES: C[C@@](Cc1ccc(OP(=O)(O)O)c(O)c1)(NN)C(=O)O]

(I-b)

or a pharmaceutically acceptable salt thereof and,
   (b) a second compound corresponding in structure Formula (II)-b:

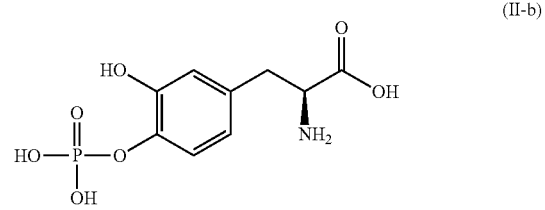 [SMILES: N[C@@H](Cc1ccc(OP(=O)(O)O)c(O)c1)C(=O)O]

(II-b)

or a pharmaceutically acceptable salt thereof;
   wherein the pharmaceutical composition is for subcutaneous administration.

2. A method of treating Parkinson's disease comprising administering to a subject in need thereof a therapeutically effective amount of the pharmaceutical composition according to claim 1.

3. The method of claim 2, further comprising administering another anti-Parkinson's agent to the subject.

4. A kit comprising the pharmaceutical composition of claim 1.

* * * * *